US008518714B2

(12) United States Patent
Soldo et al.

(10) Patent No.: US 8,518,714 B2
(45) Date of Patent: Aug. 27, 2013

(54) BINDING SURFACES FOR AFFINITY ASSAYS

(75) Inventors: Joshua C. Soldo, Burnsville, MN (US); James L. Sackrison, Minnetonka, MN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/242,699

(22) Filed: Sep. 23, 2011

(65) Prior Publication Data

US 2012/0077284 A1 Mar. 29, 2012

Related U.S. Application Data

(63) Continuation of application No. 11/979,331, filed on Nov. 1, 2007, now abandoned.

(60) Provisional application No. 60/863,820, filed on Nov. 1, 2006.

(51) Int. Cl.
*G01N 33/547* (2006.01)
*G01N 33/551* (2006.01)
*G01N 33/544* (2006.01)
*G01N 33/53* (2006.01)

(52) U.S. Cl.
USPC ............. 436/532; 436/524; 436/528; 435/7.5

(58) Field of Classification Search
None
See application file for complete search history.

(56) References Cited

U.S. PATENT DOCUMENTS

| 5,378,608 A * | 1/1995 | Marui et al. ................... 435/7.5 |
| 5,728,588 A * | 3/1998 | Caldwell et al. .............. 436/532 |
| 7,595,279 B2 * | 9/2009 | Wang et al. ...................... 506/9 |

OTHER PUBLICATIONS

Immobilization of protein to surface-grafter PEO/PPO block copolymer. Colloid & Polymer Science 1992, vol. 270, pp. 1189-1193.*

* cited by examiner

*Primary Examiner* — Shafiqul Haq
(74) *Attorney, Agent, or Firm* — Richard S. Handley; Anne M. Murphy

(57) ABSTRACT

Non-saturated or non-saturated and orientated binding surfaces for an affinity assay are provided, as are methods and compositions for their preparation. The non-saturated or non-saturated and orientated binding surfaces may further comprise paramagnetic microparticles. The methods include methods for making ligand::support coupler-based complexes by a process optionally employing a low input ratio of ligand to support coupler, by dilution, and by methods employing a dispersion and/or coating step using a block copolymer. Specific examples employing biotin-BSA and biotin-ovalbumin binding surfaces are provided, as well as strepavidin-coated microparticles and microparticles coated with capture moieties such as biotinylated immunoglobulins or fragments thereof. Other examples couple a ligand to the solid surface. Further provided are dispersed microparticles and methods for making them. Use of the methods and compositions in connection with a wide variety of analytes and capture moieties is provided, particularly for use in immunoassays.

15 Claims, 24 Drawing Sheets

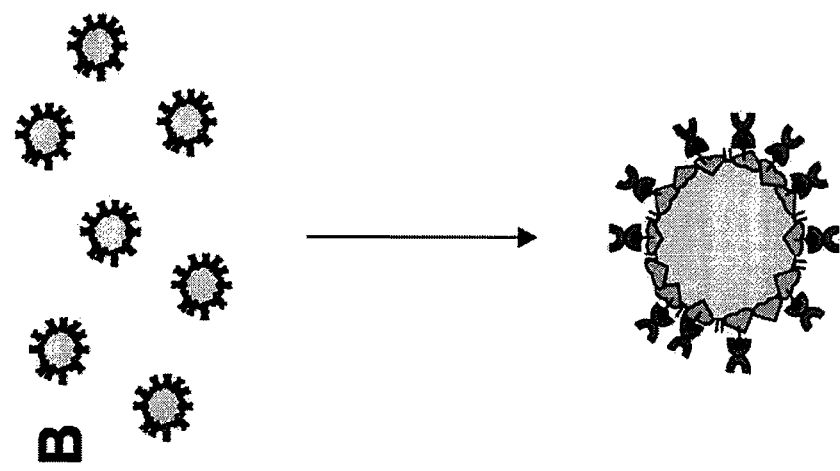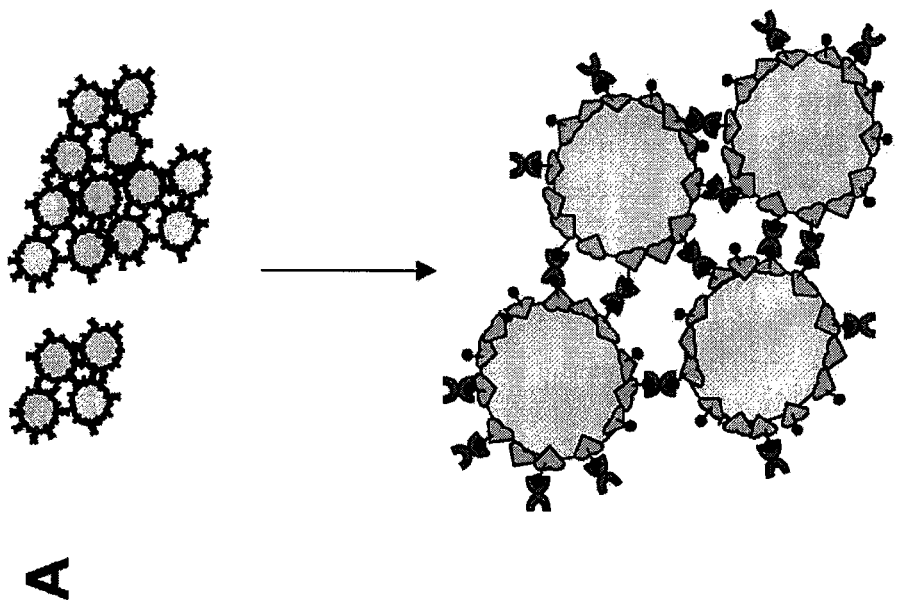
FIG. 10

VALIDATION RESULTS FOR TWELVE LOTS OF PMPs MADE WITH MANUAL AND SEMI-AUTOMATED PROCESSES TESTED AGAINST VARIOUS ANALYTE SOURCES – EXAMPLE 6

| Lot | Scale (mg) | Bio-Rad Liq. 1 | Bio-Rad Liq. 2 | Bio-Rad 1 | Bio-Rad 2 | Bio-Rad 3 | Patient 1 | Patient 2 | Patient 3 | Patient 4 | Patient 5 |
|---|---|---|---|---|---|---|---|---|---|---|---|
| 1[1] | 10,000 | 0.76 | 3.63 | 0.60 | 2.14 | 4.15 | 0.97 | 1.07 | 1.79 | 2.64 | 3.60 |
| 2[2] | 50 | 0.82 | 3.90 | 0.60 | 2.20 | 4.33 | 1.02 | 1.12 | 1.84 | 2.76 | 3.88 |
| 3[2] | 50 | 0.83 | 3.86 | 0.62 | 2.17 | 4.19 | 1.03 | 1.13 | 1.85 | 2.68 | 3.72 |
| 4[2] | 250 | 0.84 | 3.85 | 0.64 | 2.13 | 3.99 | 1.04 | 1.13 | 1.84 | 2.63 | 3.64 |
| 5[1] | 10,000 | 0.79 | 3.61 | 0.61 | 2.17 | 4.18 | 1.02 | 1.13 | 1.89 | 2.68 | 3.73 |
| 6[3] | 2,500 | 0.74 | 3.63 | 0.58 | 2.14 | 4.22 | 0.98 | 1.07 | 1.80 | 2.72 | 3.79 |
| 7[3] | 2,500 | 0.78 | 3.84 | 0.59 | 2.15 | 4.01 | 0.99 | 1.10 | 1.86 | 2.68 | 3.75 |
| 8[4] | 40,000 | 0.77 | 3.62 | 0.63 | 2.18 | 4.33 | 1.02 | 1.12 | 1.88 | 2.72 | 3.80 |
| 9[4] | 40,000 | 0.79 | 3.53 | 0.63 | 2.16 | 4.12 | 1.03 | 1.12 | 1.82 | 2.69 | 3.78 |
| 11[3] | 250 | 0.76 | 3.62 | 0.61 | 2.18 | 4.34 | 0.99 | 1.10 | 1.84 | 2.77 | 3.81 |
| 12[3] | 250 | 0.79 | 3.81 | 0.61 | 2.13 | 4.23 | 1.02 | 1.11 | 1.82 | 2.70 | 3.73 |
| VAL 959 Grand Mean (ng/mL) | | 0.79 | 3.72 | 0.61 | 2.16 | 4.19 | 1.01 | 1.11 | 1.84 | 2.70 | 3.75 |
| VAL 959 St. Dev | | 0.04 | 0.14 | 0.04 | 0.05 | 0.18 | 0.04 | 0.03 | 0.05 | 0.08 | 0.12 |
| VAL 959 %CV | | 4.97 | 3.84 | 6.03 | 2.20 | 4.19 | 3.51 | 3.05 | 2.47 | 2.82 | 3.11 |

Superscript 1: denotes a semi-automated process; Superscript 2: denotes a manual process; Superscript 3: denotes a second semi-automated process; Superscript 4: denotes a third semi-automated process.

FIG. 12

PROCESS REPRODUCIBILITY STUDIES – EXAMPLE 6

| VALIDATION LOT | SCALE (MG) | CONTROL 1 LOT C1-5190:15DA DOSE (PG/ML) | CONTROL 2 LOT C2-5190:15DA DOSE (PG/ML) | CONTROL 3 LOT C3-5190:15DA DOSE (PG/ML) | QC PATIENT 1 LOT P1-5168-143 DOSE (PG/ML) | QC PATIENT 2 LOT P2-5168-143 DOSE (PG/ML) | QC PATIENT 3 LOT P3-5168-143 DOSE (PG/ML) |
|---|---|---|---|---|---|---|---|
| 1[1] | 10,000 | 66.7 | 621.9 | 1696.0 | 29.1 | 59.9 | 421.6 |
| 4[2] | 250 | 65.2 | 612.0 | 1729.6 | 29.3 | 58.5 | 413.9 |
| 5[1] | 10,000 | 65.7 | 614.4 | 1725.2 | 29.7 | 58.3 | 420.0 |
| 6[3] | 2,500 | 68.5 | 639.9 | 1838.3 | 32.1 | 63.2 | 423.9 |
| 7[1] | 2,500 | 67.0 | 628.7 | 1847.6 | 33.1 | 61.9 | 419.6 |
| 8/Pilot 1[4] | 40,000 | 67.0 | 624.6 | 1794.6 | 33.5 | 64.4 | 432.6 |
| 9/Pilot 2[4] | 40,000 | 66.8 | 621.8 | 1791.9 | 32.9 | 65.3 | 424.8 |
| 10[2] | 50 | 65.6 | 654.2 | 1824.9 | 32.8 | 58.5 | 443.8 |
| 11 | 250 | 67.8 | 644.1 | 1789.1 | 32.1 | 62.8 | 445.7 |
| 12 | 250 | 67.2 | 622.9 | 1762.3 | 34.3 | 62.6 | 429.2 |
| VAL 959 GRAND MEAN (NG/ML) | | 66.8 | 628.5 | 1780.0 | 31.9 | 61.5 | 427.5 |
| VAL 959 STDEV | | 1.0 | 13.5 | 50.9 | 1.9 | 2.6 | 10.5 |
| VAL 959 %CV | | 1.5 | 2.1 | 2.9 | 5.8 | 4.2 | 2.4 |

[1] Superscript 1: denotes semi-automated process 2; Superscript 2: denotes a manual process; Superscript 3: denotes a semi-automated process 1; Superscript 4: denotes a semi-automated process 3.

FIG. 13

Enhanced Stability Studies – Example 7

| Incubation Time: | | 4 Days | 127 Days | | | 127 Days @ 4°C vs. 4 Day @ 4°C % | 127 Days @ 37°C vs. 4 Day @ 4°C % |
|---|---|---|---|---|---|---|---|
| Temp.: | Current FT4 Assay Specifications (For Comparison) | 4°C | 4°C | 37°C | % Recovery | | |
| Reagent Pack Lot | | 422782 | 518533 | | | | |
| Calibrator Lot: | | 420611 | 517451 | | | | |
| FT4 Parameter | | | | | | | |
| Mean Calibrator Response | Acceptable Range | | | | | | |
| S0 | 1,000,000–2,500,000 | 1,777,895 | 1,405,170 | 1,464,900 | 104.3 | n/a | n/a |
| S1 | n/a | 847,098 | 647,556 | 650,873 | 100.5 | n/a | n/a |
| S2 | n/a | 412,507 | 310,886 | 295,772 | 95.1 | n/a | n/a |
| S3 | n/a | 155,959 | 119,449 | 123,880 | 103.7 | n/a | n/a |
| S4 | n/a | 93,311 | 75,511 | 75,989 | 100.6 | n/a | n/a |
| S5 | n/a | 53,939 | 38,593 | 42,298 | 109.6 | n/a | n/a |
| Average | n/a | n/a | n/a | n/a | 102.3 | n/a | n/a |
| Ratios | Acceptable Range | | | | | | |
| S1/S0 | 40–60 | 47.6 | 46.1 | 44.4 | 96.4 | 96.7 | 93.3 |
| S2/S0 | 20–30 | 23.2 | 22.1 | 20.2 | 91.3 | 95.4 | 87.0 |
| S3/S0 | 8–11 | 8.8 | 8.5 | 8.5 | 99.5 | 96.9 | 96.4 |
| S4/S0 | 4–6.5 | 5.2 | 5.4 | 5.2 | 96.5 | 102.4 | 98.8 |
| S5/S0 | <3.5 | 3.0 | 2.7 | 2.9 | 105.1 | 90.5 | 95.2 |
| Average | n/a | n/a | n/a | n/a | 97.8 | 96.4 | 94.1 |

FIG. 14A

Enhanced Stability Studies – Example 7 – Cont'd

| INCUBATION TIME: | | 4 DAYS | | 127 DAYS | | | 127 DAYS @4°C vs. 4 DAY @ 4°C % | 127 DAYS @37°C vs. 4 DAY @ 4°C % |
|---|---|---|---|---|---|---|---|---|
| TEMP.: | CURRENT FT4 ASSAY SPECIFICATIONS (FOR COMPARISON) | 4°C | | 4°C | 37°C | % RECOVERY | | |
| REAGENT PACK LOT | | 422782 | | | 518533 | | | |
| CALIBRATOR LOT: | | 420611 | | | 517451 | | | |
| FT4 PARAMETER | | | | | | | | |
| MEAN DOSE | STATED MEAN 2SD RANGE | | | | | | | |
| Bio-Rad Lyphochek 1 Lot #40161 | 0.64 | 0.54-0.74 | 0.65 | 0.61 | 0.66 | 107.6 | 94.5 | 101.7 |
| Bio-Rad Lyphochek 2 Lot #40162 | 2.18 | 1.84-2.52 | 2.19 | 2.29 | 2.14 | 93.7 | 104.3 | 97.7 |
| Bio-Rad Lyphochek 3 Lot #40163 | 4.19 | 3.51-4.87 | 4.32 | 4.27 | 4.31 | 101.0 | 98.8 | 99.8 |
| AVERAGE | | n/a | n/a | n/a | n/a | 100.8 | 99.2 | 99.7 |
| Patient 1 | 1.02 | 0.86-1.18 | n/a | 1.08 | 1.05 | 97.4 | n/a | n/a |
| Patient 2 | 1.12 | 0.94-1.30 | n/a | 1.10 | 1.13 | 102.7 | n/a | n/a |
| Patient 3 | 1.83 | 1.53-2.13 | n/a | 1.86 | 1.89 | 101.5 | n/a | n/a |
| Patient 4 | 2.74 | 2.30-3.18 | n/a | 2.76 | 2.77 | 100.2 | n/a | n/a |
| Patient 5 | 3.80 | 3.20-4.40 | n/a | 3.92 | 3.82 | 97.5 | n/a | n/a |
| AVERAGE | | n/a | n/a | n/a | n/a | 99.9 | n/a | n/a |

FIG. 14B

SURFACE DENSITY CALCULATIONS FOR MICROPARTICLES – EXAMPLE 11

| | HABA | | | BSA | | BIOTIN | | | | | SA | | | BIOTIN-IGG | |
|---|---|---|---|---|---|---|---|---|---|---|---|---|---|---|---|
| | MIN. | MID. | MAX. | MIN. | MAX. | MIN. | MIN./MID. | MID. | MID./MAX | MAX. | MIN. | MID. | MAX. | MIN. | MAX. |
| BIOTIN/BSA (μMOL/μMOL) | 1.2 | 1.85 | 2.3 | — | — | — | — | — | — | — | — | — | — | — | — |
| BSA/PMP (μG/MG) | — | — | — | 8.7 | 14.0 | — | — | — | — | — | — | — | — | — | — |
| BSA/PMP (μMOL/MG) | — | — | — | 1.3E-04 | 2.1E-04 | — | — | — | — | — | — | — | — | — | — |
| BIOTIN/PMP (μG/MG) | — | — | — | — | — | 0.03860 | 0.05950 | 0.05950 | 0.09575 | 0.11904 | — | — | — | — | — |
| BIOTIN/PMP (μMOL/MG) | — | — | — | — | — | 1.6E-04 | 2.4E-04 | 2.4E-04 | 3.9E-04 | 4.9E-04 | — | — | — | — | — |
| SA/PMP (μG/MG) | — | — | — | — | — | — | — | — | — | — | 5.6 | 6.1 | 7.8 | — | — |
| SA/PMP (μMOL/MG) | — | — | — | — | — | — | — | — | — | — | 1.0E-04 | 1.1E-04 | 1.4E-04 | — | — |
| BIOTIN-IGG/PMP (μG/MG) | — | — | — | — | — | — | — | — | — | — | — | — | — | 3.2 | 6.1 |
| BIOTIN-IGG/PMP (μMOL/MG) | — | — | — | — | — | — | — | — | — | — | — | — | — | 2.1E-05 | 4.1E-05 |

Molecular Weights: Biotin: 244 Da; BSA: 66,000 Da; SA: 56,000 Da; IgG: 150,000 Da

FIG. 16A

SURFACE DENSITY CALCULATIONS FOR MICROPARTICLES USING A ROUGHNESS ASSUMPTION – EXAMPLE 11

| | BSA | | | BIOTIN | | | | | SA | | | BIOTIN-IgG | | |
|---|---|---|---|---|---|---|---|---|---|---|---|---|---|---|
| | MIN. | MID. | MAX. | MIN. | MIN./MID. | MID. | MID./MAX. | MAX. | MIN. | MID. | MAX. | MIN. | MID. | MAX. |
| BSA (μmol/m²) | 1.8E-02 | 1.7E-02 | 2.9E-02 | — | — | — | — | — | — | — | — | — | — | — |
| | 1.6E-02 | — | 2.5E-02 | — | — | — | — | — | — | — | — | — | — | — |
| BIOTIN (μmol/m²) | — | — | — | 2.1E-02 | 3.3E-02 | 3.2E-02 | 5.3E-02 | 6.8E-02 | — | — | — | — | — | — |
| | — | — | — | 1.9E-02 | 2.9E-02 | — | 4.7E-02 | 5.8E-02 | — | — | — | — | — | — |
| SA (μmol/m²) | — | — | — | — | — | — | — | — | 1.4E-02 | 1.4E-02 | 1.9E-02 | — | — | — |
| | — | — | — | — | — | — | — | — | 1.2E-02 | — | 1.7E-02 | — | — | — |
| BIOTIN-IgG (μmol/m²) | — | — | — | — | — | — | — | — | — | — | — | 2.9E-3 | 2.8E-3 | 5.5E-3 |
| | — | — | — | — | — | — | — | — | — | — | — | 2.5E-3 | — | 4.8E-3 |

Particle surface area ranged from a minimum of 7.4 m²/g to a maximum of 8.4 m²/g, with a midrange of 7.7 m²/g. Particle surface area calculations are based on dry solid weight.

Surface density calculations (μmol/m²) for nonparticulate and particulate supports were based on the μmol/mg calculations in Figure 16A.

FIG. 16B

| SURFACE AREA CALCULATIONS FOR MICROPARTICLES USING A SMOOTHNESS ASSUMPTION – EXAMPLE 11 |||||||||||
|---|---|---|---|---|---|---|---|---|---|---|
| PARTICLE DIAMETER (µM) | 0.90 | 1.00 | 1.10 | 0.90 | 1.00 | 1.10 | 0.90 | 1.00 | 1.10 |
| PARTICLE DENSITY (G/CM³) | 1.40 | 1.40 | 1.40 | 1.60 | 1.60 | 1.60 | 1.80 | 1.80 | 1.80 |
| PARTICLE DENSITY (MG/CM³) | 1400 | 1400 | 1400 | 1600 | 1600 | 1600 | 1800 | 1800 | 1800 |
| DIAMETER/PARTICLE (CM) | 0.00009 | 0.0001 | 0.00011 | 0.00009 | 0.0001 | 0.00011 | 0.00009 | 0.0001 | 0.00011 |
| RADIUS/PARTICLE (CM) | 0.000045 | 0.00005 | 0.000055 | 0.000045 | 0.00005 | 0.000055 | 0.000045 | 0.00005 | 0.000055 |
| VOLUME/PARTICLE (CM³) | 3.81704E-13 | 5.23599E-13 | 6.9691E-13 | 3.81704E-13 | 5.23599E-13 | 6.9691E-13 | 3.81704E-13 | 5.23599E-13 | 6.9691E-13 |
| SURFACE AREA/PARTICLE (CM²) | 2.54469E-08 | 3.14159E-08 | 3.80133E-08 | 2.54469E-08 | 3.14159E-08 | 3.80133E-08 | 2.54469E-08 | 3.14159E-08 | 3.80133E-08 |
| MG/PARTICLE | 5.34E-10 | 7.33E-10 | 9.76E-10 | 6.11E-10 | 8.38E-10 | 1.12E-09 | 6.87E-10 | 9.42E-10 | 1.25E-09 |
| PARTICLE/MG | 1.87E+09 | 1.36E+09 | 1.02E+09 | 1.64E+09 | 1.19E+09 | 8.97E+08 | 1.46E+09 | 1.06E+09 | 7.97E+08 |
| SURFACE AREA/MG (CM²) | 47.62 | 42.86 | 38.96 | 41.67 | 37.50 | 34.09 | 37.04 | 33.33 | 30.30 |
| SURFACE AREA/MG (M²) | 0.0048 | 0.0043 | 0.0039 | 0.0042 | 0.0038 | 0.0034 | 0.0037 | 0.0033 | 0.0030 |

Particle surface area calculations are based on particles having diameters from a minimum of 0.90 µm to a maximum of 1.10 µm, with a midrange of 1.00 µm, and particle densities from a minimum of 1.40 g/cm³ to a maximum of 1.80 g/cm³, with a midrange of 1.60 g/cm³.

FIG. 16C

SURFACE DENSITY CALCULATIONS FOR MICROPARTICLES USING A SMOOTHNESS ASSUMPTION – EXAMPLE 11

| | BSA | | BIOTIN | | | | SA | | | BIOTIN-IGG | |
|---|---|---|---|---|---|---|---|---|---|---|---|
| | MIN. | MAX. | MIN. | MIN./MID. | MID. | MID./MAX. | MAX. | MIN. | MID. | MAX. | MIN. | MAX. |
| BSA ($\mu mol/m^2$) | 4.4E-02 | 7.1E-02 | --- | --- | --- | --- | --- | --- | --- | --- | --- | --- |
| | 2.8E-02 | 4.5E-02 | --- | --- | --- | --- | --- | --- | --- | --- | --- | --- |
| BIOTIN ($\mu mol/m^2$) | --- | --- | 5.2E-02 | 8.0E-02 | 8.0E-02 | 1.3E-01 | 1.6E-01 | --- | --- | --- | --- | --- |
| | --- | --- | 3.3E-02 | 5.1E-02 | 5.1E-02 | 8.2E-02 | 1.0E-01 | --- | --- | --- | --- | --- |
| SA ($\mu mol/m^2$) | --- | --- | --- | --- | --- | --- | --- | 3.3E-02 | 3.6E-02 | 4.6E-02 | --- | --- |
| | --- | --- | --- | --- | --- | --- | --- | 2.1E-02 | 2.3E-02 | 2.9E-02 | --- | --- |
| BIOTIN-IGG ($\mu mol/m^2$) | --- | --- | --- | --- | --- | --- | --- | --- | --- | --- | 7.1E-03 | 1.4E-02 |
| | --- | --- | --- | --- | --- | --- | --- | --- | --- | --- | 4.4E-03 | 8.5E-03 |

Smoothed-surface particle surface areas ranged from a minimum of 0.0030 $m^2/mg$ to a maximum of 0.0048 $m^2/mg$ (see Figure 16C).

Surface density calculations ($\mu mol/m^2$) for microparticles using a smoothness assumption were based on the $\mu mol/mg$ calculations in Figure 16A, and $m^2/mg$ calculations in Figure 16C.

FIG. 16D

BINDING SURFACES FOR AFFINITY ASSAYS

CROSS-REFERENCE TO RELATED APPLICATIONS

This application is a Continuation of U.S. patent application Ser. No. 11/979,331 filed Nov. 1, 2007 which claims priority to U.S. Provisional Patent Application No. 60/863,820, filed Nov. 1, 2006.

FIELD OF INVENTION

The present invention relates to supports having binding surfaces that are non-saturated or non-saturated and orientated, including supports having binding surfaces comprising ligands for use in affinity assays. Particular aspects of the invention relate to binding surfaces comprising biotin, or biotin and a biotin-specific ligand binder such as streptavidin (SA). Binding surfaces for immunoassays are provided, including binding surfaces comprising antigens or antibodies, or fragments thereof. Further embodiments of the present invention relate to blocked solid support surfaces and dispersed microparticles. Methods for making and using such supports are provided.

BACKGROUND

Binding surfaces are used in a wide variety of applications including, for example, affinity assays. Conventional binding surfaces are typically prepared by maximizing the amount of ligand binders per unit surface area of the solid phase support surface. Although the conventional approach results in a support surface with a high density of ligand binders, simply maximizing the number of ligand binders on a support surface does not invariably improve performance of the binding surface. Some conventional binding surfaces used in affinity assays maximize binding capacity by direct coating of a ligand binder such as an antibody, or a biotin-specific ligand binder such as SA, onto a solid phase and blocking the solid phase with bovine serum albumin (BSA) or ovalbumin. Although this maximizes the antigen or biotin binding capacity of the binding surface, the respective antibodies or biotin-specific ligand binders are crowded on the binding surface without specific orientation, and traditional blocking strategies do not necessarily prevent or mitigate sloughing of antibodies or biotin-specific ligand binders from the binding surface. Further, sloughing can result in poor assay sensitivity (sub-optimal signal-to-noise ratio), accuracy, precision, stability, or manufacturability, or combinations thereof. Binding surface crowding and random orientation can decrease binding efficiency or capacity of the binding surface due to steric hindrance. Accordingly, there is a need for improved binding surfaces and compositions and methods for making improved binding surfaces that do not rely on simply maximizing the density of ligand binders on a binding surface.

SUMMARY

Non-saturated or non-saturated and orientated binding surfaces, methods for making non-saturated or non-saturated and orientated binding surfaces, and methods for making components of non-saturated or non-saturated and orientated binding surfaces are provided. Methods and compositions for non-saturated or non-saturated and orientated binding surfaces for affinity assays, such as, for example, immunoassays, are also provided.

In one aspect, the invention provides methods and compositions for preparing a non-saturated or non-saturated and orientated capture moiety for an immunoassay, wherein the capture moiety is non-saturated or non-saturated and orientated by virtue of binding to a non-saturated or non-saturated and orientated binding surface. In a specific embodiment, the capture moiety comprises an immunoglobulin or fragment thereof, wherein the capture moiety is immobilized on the non-saturated or non-saturated and orientated binding surface by association with a ligand immobilized on a support coupler, wherein the support coupler is immobilized on a solid phase support. In a specific embodiment, the immunoglobulin or fragment thereof is biotinylated, the biotinylated immunoglobulin or fragment thereof is associated with a biotin-specific ligand binder (biotin-binding moiety), and the biotin-specific ligand binder is associated with biotin attached to the support directly or through a support coupler. In a specific embodiment, the support coupler comprises a protein, and the solid phase support comprises a microparticle.

In another aspect, the invention provides a method for performing an immunoassay using a support having a non-saturated or non-saturated and orientated binding surface, wherein the method comprises employing an immunoglobulin or fragment thereof to capture an analyte, wherein the immunoglobulin or fragment thereof is non-saturated or non-saturated and orientated on the binding surface. In various embodiments, the non-saturated or non-saturated and orientated nature of the immunoglobulin or fragment thereof is determined by the non-saturated or non-saturated and orientated nature of the binding surface with which the immunoglobulin or fragment thereof is bound.

In another aspect, the invention provides a support having a non-saturated or non-saturated and orientated binding surface, comprising ligands coupled with the support, either directly or indirectly via coupling to a support coupler which is coupled to the support, wherein the ligands are present at a density of about $1.0 \times 10^{-3}$ to about $5.0 \times 10^{-1}$ micromoles of ligand per square meter of support, or about $0.5 \times 10^{-2}$ to about $2.0 \times 10^{-1}$ micromoles of ligand per square meter of support, or about $1.0 \times 10^{-2}$ to about $1.6 \times 10^{-1}$ micromoles of ligand per square meter of support, or about $1.0 \times 10^{-2}$ to about $2.0 \times 10^{-1}$ micromoles of ligand per square meter of support, or alternatively the ligands are present at a density of about $0.5 \times 10^{-4}$ to about $10 \times 10^{-4}$ micromoles of ligand per milligram (mg) of microparticles, or about $1.0 \times 10^{-4}$ to about $5.5 \times 10^{-4}$ micromoles of ligand per mg of microparticles. In various embodiments, support couplers are present on the assay support at a density of about $1.2 \times 10^{-2}$ micromoles per square meter to about $7.5 \times 10^{-2}$ micromoles per square meter of the assay support In various embodiments, the ligands are associated with ligand binders, wherein the ligand binders are present at a density of less than about $0.4 \times 10^{-2}$ to less than about $8 \times 10^{-2}$ micromoles of ligand binder per square meter of support, or at a density of about $1.0 \times 10^{-2}$ to about $5.0 \times 10^{-2}$ micromoles per square meter of the assay support.

Embodiments of the present invention are directed to having a capture moiety present on the assay support at a density of about $1.0 \times 10^{-4}$ micromoles per square meter to about $2.0 \times 10^{-2}$ micromoles per square meter of the assay support. In various embodiments, the binding surface further comprises a capture moiety, wherein the capture moiety is present at a density of less than about $2 \times 10^{-3}$ to less than about $4 \times 10^{-2}$ micromoles of capture moiety per square meter of support. In a specific embodiment, the ligand (e.g., biotin) is present at a density of about $1.9 \times 10^{-2}$ to about $1.6 \times 10^{-1}$ micromoles of ligand per square meter of support, the ligand binder (e.g., a biotin-binding moiety such as SA) is present at about $1.0\times10^{-2}$ to about $5.0\times10^{-2}$ micromoles per square meter of the assay support, or about $1.2\times10^{-2}$ to less than about $4.6\times10^{-2}$ micromoles of ligand binder per square meter of support, and the capture moiety (e.g., a biotinylated capture moiety such as biotinylated analyte-specific antibody) is present at a density of about $2.5\times10^{-3}$ to about $1.4\times10^{-2}$ micromoles of capture moiety per square meter of support. In at least one embodiment of the present invention, the support coupler is optional. In such an embodiment, the ligand could be biotin or a derivative thereof.

In a specific embodiment, the ligand comprises biotin or a derivative thereof. In another specific embodiment, the ligand binder comprises a biotin-binding moiety, or fragment thereof, such as, for example, avidin, SA, neutravidin, a fragment of SA, a fragment of avidin, a fragment of neutravidin, or mixtures thereof. In various embodiments, the capture moiety comprises one or more of an antibody, a binding fragment of an antibody, a receptor, a ligand of a receptor, a hormone, a receptor of a hormone, an enzyme, a substrate of an enzyme, a single stranded oligonucleotide, a single stranded polynucleotide, a double stranded oligonucleotide, a double stranded polynucleotide, an antigen, a peptide, or a protein. In various embodiments, the ligands are coupled with the support through support couplers, and the support couplers are in turn coupled with the support. In a specific embodiment, the support couplers comprise protein. In a specific embodiment, the protein is BSA, ovalbumin, a fragment of BSA, a fragment of ovalbumin, or mixtures thereof. In a specific embodiment, the support is a microparticle. In a specific embodiment, the binding surface has about $1\times10^{-2}$ to about $5\times10^{-1}$ micromoles of ligand per square meter of support, or alternatively, the binding surface has about $2\times10^{-2}$ to about $2\times10^{-1}$ micromoles of ligand per square meter of support. In another specific embodiment, the binding surface has about $1.9\times10^{-2}$ to about $1.6\times10^{-1}$ micromoles of ligand per square meter of support. In another specific embodiment, the binding surface has about $1.6\times10^{-2}$ to about $6.6\times10^{-2}$ micromoles of ligand per square meter of support. In another specific embodiment, the binding surface has about $1.6\times10^{-2}$ to about $3.2\times10^{-2}$ micromoles of ligand per square meter of support. In another specific embodiment, the binding surface has about $1.6\times10^{-2}$ to about $2.0\times10^{-1}$ micromoles of ligand per square meter of support.

In various embodiments, the binding surface comprises a ligand binder attached to the ligand and a capture moiety attached to the ligand binder, wherein the capture moiety is present at a density, in various embodiments, of about 75% of the density of the ligand, of about 50% of the density of the ligand, and of about 25% of the density of the ligand.

In a specific embodiment, the ligand comprises biotin, the biotin is coupled with the support through a support coupler protein selected from BSA, ovalbumin, a fragment of BSA, a fragment of ovalbumin, or mixtures thereof, the biotin is attached to a ligand binder comprising a biotin-binding moiety selected from avidin, SA, neutravidin, a fragment of SA, a fragment of avidin, a fragment of neutravidin, or mixtures thereof, and the biotin-binding moiety is attached to a biotinylated capture moiety, wherein the capture moiety is selected from the group consisting of one or more of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single stranded polynucleotide, a double stranded polynucleotide, an antigen, a peptide, or a protein.

In another aspect, the invention provides a support having a non-saturated and orientated binding surface, comprising: a plurality of support couplers disposed on the support; and ligands coupled with the support couplers; wherein the ligands are non-saturated and are orientated on the surface in a manner that provides sterically accessible ligands. In a specific embodiment, the ligands are associated with bi- or multivalent ligand binders capable of specifically associating with the ligands, and the binding surface is substantially free of unbound, free ligand.

In various embodiments, the support couplers are coupled with about $1.9\times10^{-2}$ to about $1.6\times10^{-1}$ micromoles of ligand per square meter of support.

The support couplers can be coupled with the support through covalent or non-covalent association. In various embodiments, the support couplers are covalently coupled with the support. In embodiments where the support couplers are covalently coupled with the support, any suitable binding chemistry known in the art can be used to attach the support coupler to the support. Suitable binding chemistries include, but are not limited to, attachment through one or more functional groups selected from the group consisting of carboxyl, hydroxyl, tosyl, epoxy, aldehyde, amine, amide, hydrazide, isothiocyanate, maleimide, and sulfhydryl. In a specific embodiment, the support coupler is covalently coupled with the support using tosyl chemistry for attachment.

The support couplers can comprise any suitable substance that can be coupled with a support and also with a ligand. The coupling with the support, and the coupling with the ligand, can be covalent. Suitable support couplers include, but are not limited to, macromolecules such as, for example, proteins or other polymers. In various embodiments, the support coupler comprises protein. The protein can be, for example, a monomer, a dimer, a multimer, or a fusion protein. In specific embodiments, the protein comprises at least one of an albumin such as, for example, BSA, ovalbumin, a fragment of BSA, a fragment of ovalbumin, or mixtures thereof.

In various embodiments, the ligands comprise biotin. Suitable biotin reagents for attaching biotin to a support surface or a support coupler include amine-reactive biotin labeling reagents such as, for example, sulfo-NHS-biotin, sulfo-NHS-LC-biotin, sulfo-NHS-LC-LC-biotin, sulfo-NHS-SS-biotin, NHS-PEO$_4$-biotin, NHS-biotin, NHS-LC-biotin, NHS-LC-LC-biotin, PFP-biotin, TFP-PEO-biotin, or NHS-iminobiotin trifluoroacetamide, sulfhydryl-reactive biotin labeling reagents such as, for example, maleimide-PEO$_2$-biotin, biotin-BMCC, PEO-Iodoacetyl biotin, iodoacetyl-LC-biotin, or biotin-HPDP, carboxyl-reactive biotin labeling reagents such as, for example, biotin PEO-amine or biotin PEO-LC-amine, carbohydrate-reactive biotin labeling reagents such as, for example, biocytin hydrazide, biotin hydrazide, or biotin-LC-hydrazide, or photoreactive biotin labeling reagents such as, for example, psoralen-PEO-biotin. In a specific embodiment, the ligand comprises biotin and is attached to the support or support coupler using the amine reactive biotin labeling reagent sulfo-NHS-LC-biotin.

In embodiments where the ligands comprise biotin, the binding surface on the support can further comprise a ligand binder associated with the biotin. In certain embodiments, the ligand binder comprises a biotin-binding moiety. In various embodiments, the biotin-binding moiety comprises protein, for example, at least one of a biotin-binding protein such as avidin, SA, neutravidin, a fragment of SA, a fragment of avidin, a fragment of neutravidin, or mixtures thereof. The biotin-binding moiety could also comprise a fusion protein such as, for example, avidin fused to a different binding protein.

In various embodiments, the support couplers comprise a protein and the ligand comprises biotin, and the protein is biotinylated at a low input ratio of biotin, such that the support couplers have an incorporation ratio of less than or equal to 5 moles of biotin per mole of support coupler. In a specific embodiment, the protein is BSA, ovalbumin, a fragment of BSA, a fragment of ovalbumin, or mixtures thereof.

In various embodiments, where the binding surface on the support comprises a biotin-binding moiety, the binding surface on the support further comprises a biotinylated capture moiety associated with the biotin-binding moiety. The biotinylated capture moiety can comprise a spacer, for example, wherein the spacer is between the biotin moiety and the capture moiety. The biotinylated capture moiety can comprise any suitable capture moiety according to the substance to be captured. Suitable capture moieties include at least one of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single polynucleotide, a double stranded polynucleotide, an antigen, a peptide, or a protein.

In various embodiments, the binding surface on the support further comprises a block copolymer comprising a hydrophobic head group flanked by at least two hydrophilic tails, wherein the hydrophobic head group contacts the support.

The length of the hydrophilic tails can be each independently about 2 to about 2.5 times as long as the head group. The block copolymer can comprise a structure of general formula I having a polypropylene oxide block and a polyethylene oxide block,

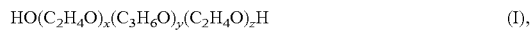

$$HO(C_2H_4O)_x(C_3H_6O)_y(C_2H_4O)_zH \qquad (I),$$

wherein x and y are selected so that the polypropylene oxide block associates with the support. In a specific embodiment, x is about 100 to about 135, y is about 40 to about 75 and z is about 100 to about 135. In other embodiments, x is about 110 to about 125, y is about 60 to about 70, and z is about 110 to about 125. In various embodiments, the block copolymer has an average molecular weight of about 12,700 daltons (Da)-17,400 Da; or an average molecular weight of about 9,000 to about 18,000 Da. In specific embodiments, the block copolymer has an average molecular weight of about 9,840 Da to about 14,600 Da. In a specific embodiment, the block copolymer has an average molecular weight of about 14,600 Da. In another specific embodiment, the block copolymer has an average molecular weight of about 12,600 Da.

In various embodiments, the support comprises an organic polymer or copolymer. In various embodiments, the organic polymer or copolymer is hydrophobic. Suitable polymers include, but are not limited to, polystyrene, poly(divinylbenzene), styrene-acylate copolymer, styrene-butadiene copolymer, styrene-divinylbenzene copolymer, poly(styrene-oxyethylene), polymethyl methacrylate, polyurethane, polyglutaraldehyde, polyethylene imine, polyvinylpyrrolidone, N,N'-methylene bis-acrylamide, polyolefeins, polyethylene, polypropylene, polyvinylchloride, polyacrylonitrile, polysulfone, poly(ether sulfone), pyrolized materials, block copolymers, and copolymers of the foregoing, silicones, or silica. In a specific embodiment, the support comprises styrene and divinylbenzene, and is coated with a polyurethane layer.

In various embodiments, using a polymer or copolymer that is hydrophobic will result in a support with a water contact angle of more than about 60 degrees. In various embodiments, using a polymer or copolymer that is hydrophobic will result in a support with a water contact angle of more than about 70 degrees.

In various embodiments the support comprises a microparticle. In a specific embodiment, the microparticle comprises a paramagnetic or superparamagnetic material such as, for example, ferromagnetic iron oxide $Fe_3O_4$ or $Fe_2O_3$. The terms "paramagnetic" and "superparamagnetic" refer to materials that experience a force in a magnetic field gradient, but do not become permanently magnetized. In a specific embodiment, the support comprises iron in the form of maghemite, or $Fe_2O_3$. In various embodiments, the mean diameter of the microparticle is in the range of 100 nm to 22,900 nm. In a specific embodiment, the mean diameter of the microparticle is in the range of about 750 nm to about 3,000 nm. In another specific embodiment, the mean diameter of the microparticle is in the range of about 950 nm to about 1,150 nm.

In another aspect, a modified support for an affinity assay is provided, comprising: a support comprising one or more materials selected from the group consisting of polystyrene, poly(divinylbenzene), styrene-acylate copolymer, styrene-butadiene copolymer, styrene-divinylbenzene copolymer, poly(styrene-oxyethylene), polymethyl methacrylate, polyurethane, polyglutaraldehyde, polyethylene imine, polyvinylpyrrolidone, N,N'-methylene bis-acrylamide, polyolefeins, polyethylene, polypropylene, polyvinylchloride, polyacrylonitrile, polysulfone, poly(ether sulfone), pyrolized materials, block copolymers, and copolymers of the foregoing, silicones, or silica; a protein covalently attached to the support, wherein the protein comprises a biotin, wherein there are less than 5 moles of biotin coupled per mole of protein; a biotin-binding moiety associated with the biotin, wherein the biotin-binding moiety is at least bivalent; a biotinylated capture moiety associated with the biotin-binding moiety, wherein the biotinylated capture moiety is selected from the group consisting of at least one of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single stranded polynucleotide, a double stranded polynucleotide, an antigen, a peptide, or a protein; a block copolymer contacting the support, wherein the block copolymer comprises a polypropylene oxide head group flanked by polyethylene oxide tails, wherein the polypropylene oxide head group contacts the support, and wherein the polyethylene oxide tails are independently about 2 to about 2.5 times as long as the polypropylene oxide head group, and wherein the average molecular weight of the block copolymer is about 9,840 Da to about 17,400 Da. The modified support can comprise a microparticle. In a specific embodiment, the microparticle comprises a paramagnetic or superparamagnetic material such as $Fe_2O_3$, and the mean diameter of the microparticle is in the range of 950 nm to 1,150 nm. In a specific embodiment, the biotinylated capture moiety comprises an immunoglobulin or fragment thereof.

In another aspect, a method for coating a support is provided, comprising: combining ligands and support couplers at an input ratio of ligands to support couplers selected so as to result in a mixture of ligand::support coupler complexes wherein the ligand::support coupler complexes are at least substantially free of free ligand; and covalently attaching the ligand::support coupler complexes to a support. In a specific embodiment, the input ratio of ligands to support couplers is less than or equal to 8 moles of ligand:1 mole of support coupler. Alternatively, the input ratio of ligands to support couplers is less than or equal to 4 moles of ligand:1 mole of support coupler.

In a specific embodiment, the ligands of the method comprise biotin, wherein the ligand comprises an amine reactive biotin labeling reagent such as sulfo-NHS-LC-biotin.

In various embodiments, the support couplers comprise a protein and the ligand comprises biotin, and the protein is biotinylated at a low input ratio of biotin, such that the support couplers have an incorporation ratio of less than 5 moles of biotin per mole of support coupler. In a specific embodiment, the protein is BSA, ovalbumin, a fragment of BSA, a fragment of ovalbumin, or mixtures thereof.

In another aspect, a method for coating microparticles is provided, comprising: exposing the microparticles to a dispersant to form a dispersion, wherein the microparticles comprise binding surfaces comprising ligands and support couplers that are coupled to yield ligand::support coupler complexes and the dispersant comprises a block copolymer having a hydrophobic head group flanked by hydrophilic tail groups; and exposing the dispersion to ligand binders that associate with the ligands of the ligand::support coupler complexes.

In a specific embodiment of the method for coating, the ligand comprises biotin, and is coupled with the support or the support coupler with an amine reactive biotin labeling reagent such as sulfo-NHS-LC-biotin. In various embodiments, the support couplers comprise protein, as described above for supports having a non-saturated or non-saturated and orientated binding surface. In a specific embodiment, the protein comprises BSA, ovalbumin, a fragment of BSA, a fragment of ovalbumin, or mixtures thereof.

In various embodiments of the method for coating, the ligand binder comprises a biotin-binding moiety. In a specific embodiment, the biotin-binding moiety is at least bivalent and comprises at least one of avidin, SA, neutravidin, a fragment of SA, a fragment of avidin, a fragment of neutravidin, or mixtures thereof.

In various embodiments, the method for coating further comprises associating a biotinylated capture moiety with the biotin-binding moiety. In a specific embodiment of the method for coating, the biotinylated capture moiety comprises at least one of an antibody, a binding fragment of an antibody, a receptor, a ligand of a receptor, a hormone, a receptor of a hormone, an enzyme, a substrate of an enzyme, a single stranded oligonucleotide, a double stranded oligonucleotide, a single stranded polynucleotide, a double stranded polynucleotide, an antigen, a peptide, or a protein. In a specific embodiment, the biotinylated capture moiety comprises a spacer.

In another aspect, a method for making a non-saturated or non-saturated and orientated binding surface on a support is provided, comprising: preparing a mixture of analyte-associating moieties with space-filling moieties, to form a diluted mixture; and, exposing the mixture to an assay support under conditions sufficient for the analyte-associating moieties and space-filling moieties to couple with the support and form a non-saturated or non-saturated and orientated binding surface that is non-saturated with respect to the number of analyte-associating moieties that are coupled with the support surface. As used herein, an analyte-associating moiety may be any molecule, such as a protein, antibody, or nucleic acid, that when bound with a support surface will associate, either directly, or indirectly through a linking molecule, with an analyte of interest; i.e., it will form part of the binding surface. As used herein, a space-filling moiety is any molecule, such as a protein, antibody, or nucleic acid, that will couple with a support surface but will not associate, either directly, or indirectly through a linking molecule, with an analyte of interest. The space-filling moiety will not form part of the binding surface but will function to occupy space on the support surface and prevent binding of excess analyte-associating moieties.

In another aspect, a method for making a non-saturated or non-saturated and orientated binding surface on a support is provided, comprising: diluting a mixture of ligand::support coupler complexes with support coupler that lacks ligands, to form a diluted mixture; and, exposing the diluted mixture to a support under conditions sufficient for the ligand::support coupler complexes to couple with the support and form a non-saturated or non-saturated and orientated binding surface In various embodiments of the method for making a non-saturated or non-saturated and orientated binding surface on a support, wherein the support comprises a microparticle, the non-saturated binding surface has about $0.5 \times 10^{-4}$ to about $10 \times 10^{-4}$ micromoles of ligand per milligram (mg) of microparticles, about $1.0 \times 10^{-4}$ to about $5.5 \times 10^{-4}$ micromoles of ligand per mg of microparticles, or about $2 \times 10^{-4}$ to about $4 \times 10^{-4}$ micromoles of ligand per mg of microparticles. In specific embodiments of the method for making a non-saturated or non-saturated and orientated binding surface on a support, wherein the support comprises a microparticle, the non-saturated or non-saturated and orientated binding surface has about $1.0 \times 10^{-4}$ to about $5.5 \times 10^{-4}$ micromoles of ligand per mg of microparticles, or about $1.6 \times 10^{-4}$ to about $4.9 \times 10^{-4}$ micromoles of ligand per mg of microparticles.

In specific embodiments of the method for making a non-saturated or non-saturated and orientated binding surface on a support, the support is rough and the non-saturated or non-saturated and orientated binding surface has about $1.0 \times 10^{-2}$ to about $2.0 \times 10^{-1}$ micromoles of ligand per square meter. Alternatively, the binding surface has about $1.9 \times 10^{-2}$ to about $6.6 \times 10^{-2}$ micromoles of ligand per square meter. In other specific embodiments of the method for making a non-saturated or non-saturated and orientated binding surface on a support, the support is smooth and the non-saturated or non-saturated and orientated binding surface has about $3.3 \times 10^{-2}$ to about $1.6 \times 10^{-1}$ micromoles of ligand per square meter. In other specific embodiments of the method for making a non-saturated or non-saturated and orientated binding surface on a support, the rough non-saturated or non-saturated and orientated binding surface has about $1.9 \times 10^{-2}$ to about $6.6 \times 10^{-2}$ micromoles of support coupler per square meter, and the smooth non-saturated or non-saturated and orientated binding surface has about $2.7 \times 10^{-2}$ to about $7.1 \times 10^{-2}$ micromoles of support coupler per square meter. The term "rough" includes a cauliflower-like, or porous, morphology. The term "smooth" refers to a substantially smooth, and substantially spherical, morphology. For microparticles with the same diameter, the "rough" support surface will have greater support surface area than the "smooth" support surface due to increased support surface area offered by the grooves, pits, or pores of the rough support surface. The actual micromoles of support coupler, ligand, ligand binder, capture moiety, etc., will fall somewhere between the calculated rough and smooth support surface areas since not all of the rough support surface area will be sterically available for ligand, or support coupler, attachment.

In various embodiments of the method for making a non-saturated or non-saturated and orientated binding surface on a support, the support coupler comprises protein, as described above for the support having a non-saturated or non-saturated and orientated binding surface. In a specific embodiment, the protein comprises BSA, ovalbumin, a fragment of BSA, a fragment of ovalbumin, or mixtures thereof.

In another aspect, a method for making a non-saturated or non-saturated and orientated binding surface on a support is provided, comprising: preparing a mixture of ligand::support coupler complexes at any input ratio of ligand to support coupler; diluting the mixture of ligand::support coupler complexes with support coupler that is uncomplexed to ligand to form a diluted mixture; and exposing the diluted mixture to a support under conditions sufficient for the ligand::support coupler complexes and the support coupler to couple with the support and form a non-saturated or non-saturated and orientated binding surface. The support comprising the ligand can then be treated in accordance with any suitable method described herein.

The support coupler can comprise one or more of a protein or non-protein polymer. In various embodiments, the ligand is complexed to the support coupler through functional groups on the support coupler. A fraction of the number of functional groups on one or more support couplers can be eliminated or neutralized before exposing the support coupler to the ligand, in this manner reducing the number of ligands that can complex with the support coupler. All or only some of the support couplers exposed to the ligand in preparing the mixture of ligand::support coupler complexes can have one or more neutralized functional groups.

In another aspect, the invention provides a binding surface for an immunoassay, wherein the binding surface comprises a plurality of ligands that are capable of binding a ligand binder that can bind a capture moiety of interest. The ligands of the binding surface are non-saturated or non-saturated and orientated on a support, and the ligands are either (a) attached directly to the support, or (b) are attached through a support coupler and the support coupler is attached to the support. In various embodiments, the binding surface is substantially free of free (i.e., unbound) ligands. In a specific embodiment, the support comprises a microparticle, on the order of about one micron to about five microns in diameter, the ligand comprises biotin, and the biotin is complexed to a support coupler that comprises protein. In specific embodiments the ligand comprises biotin, the ligand binder comprises a biotin-binding protein, the support coupler comprises BSA, ovalbumin, a fragment of BSA, a fragment of ovalbumin, or mixtures thereof, and the BSA, ovalbumin, fragment of BSA, fragment of ovalbumin, or mixtures thereof is biotinylated by low input ratio biotinylation. In a specific embodiment, the biotin-binding protein is SA, and a biotinylated antibody is present on the SA-coated binding surface, wherein the biotinylated antibody is selected so as to capture an analyte of interest in an immunoassay, for example, a competitive or a sandwich immunoassay. The binding surface on the support of the immunoassay can be made using any suitable method described herein.

In another aspect, a support having a non-saturated or non-saturated and orientated binding surface is provided, comprising: a plurality of support couplers disposed on the support; and, ligands coupled with the support couplers; wherein the support couplers are present on the support at a density of about $1.6 \times 10^{-2}$ to about $7.1 \times 10^{-2}$ micromoles per square meter of the support. In various embodiments, the support coupler comprises a protein. In a specific embodiment, the protein is BSA, ovalbumin, a fragment of BSA, a fragment of ovalbumin, or mixtures thereof. In various embodiments, the ligand comprises biotin. In a specific embodiment, the biotin is present at a density of about $1.9 \times 10^{-2}$ to about $1.6 \times 10^{-1}$ micromoles of biotin per square meter of support. In various embodiments, the binding surface comprises a ligand binder capable of specifically associating with the ligands. In various embodiments, the ligand binder is present at a density of about $1.2 \times 10^{-2}$ to about $4.6 \times 10^{-2}$ micromoles of ligand binder per square meter of the support.

In various embodiments, the ligand binder is avidin, SA, neutravidin, a fragment of SA, a fragment of avidin, a fragment of neutravidin, or mixtures thereof. In various embodiments the binding surface further comprises a capture moiety capable of specifically associating with the ligand binder. In various embodiments, the capture moiety is present at a density of about $2.5 \times 10^{-3}$ to about $1.4 \times 10^{-2}$ micromoles of capture moiety per square meter of support. In a specific embodiment, the capture moiety comprises an immunoglobulin or fragment thereof.

In another aspect, a support having a non-saturated or non-saturated and orientated binding surface is provided, comprising: a plurality of support couplers disposed on the support; and, ligands coupled with the support couplers; wherein the support couplers are present on the support at a density of about $1.3 \times 10^{-4}$ to about $2.1 \times 10^{-4}$ micromoles of support coupler per mg of the support. In various embodiments, the ligand comprises biotin. In a specific embodiment, the biotin is present at a density of about $1.6 \times 10^{-4}$ to about $4.9 \times 10^{-4}$ micromoles of biotin per mg of support. In various embodiments, the binding surface comprises a ligand binder capable of specifically associating with the ligands. In various embodiments, the ligand binder is present at a density of about $1.0 \times 10^{-4}$ to about $1.4 \times 10^{-4}$ micromoles of ligand binder per mg of the support. In various embodiments, the ligand binder is avidin, SA, neutravidin, a fragment of SA, a fragment of avidin, a fragment of neutravidin, or mixtures thereof. In various embodiments the binding surface further comprises a capture moiety capable of specifically associating with the ligand binder. In various embodiments, the capture moiety is present at a density of about $2.1 \times 10^{-5}$ to about $4.1 \times 10^{-5}$ micromoles of capture moiety per mg of support. In a specific embodiment, the capture moiety comprises a biotinylated immunoglobulin or fragment thereof.

In another aspect, a binding surface on a support is provided, wherein the binding surface specifically binds no more than about $4.0 \times 10^{-4}$ micromoles of biotin per mg of support. In a specific embodiment, the support comprises microparticles and specifically binds about $2.5 \times 10^{-5}$ to no more than about $4.0 \times 10^{-4}$ micromoles of biotin per mg of microparticles. In a specific embodiment, the support comprises microparticles and specifically binds about $7.5 \times 10^{-5}$ to about $3.5 \times 10^{-4}$ micromoles of biotin per mg of microparticles. In another specific embodiment, the support comprises microparticles and specifically binds about $1.0 \times 10^{-4}$ to about $3.0 \times 10^{-4}$ micromoles of biotin per mg of microparticles. In various embodiments, the support comprises biotin attached to the support (directly or through a support coupler) associated with a biotin-binding moiety, such as, for example, SA, and the foregoing biotin binding capacities refer to the ability of the biotin-binding moiety (e.g., SA) to bind free biotin.

In another aspect, a binding surface on a support is provided, wherein the binding surface specifically binds no more than about $1.3 \times 10^{-1}$ micromoles of biotin per square meter of support. In a specific embodiment, the support specifically binds about $3.0 \times 10^{-3}$ to no more than about $1.3 \times 10^{-1}$ micromoles of biotin per square meter of support. In a specific embodiment, the support specifically binds about $8.9 \times 10^{-3}$ to about $1.2 \times 10^{-1}$ micromoles of biotin per square meter of support. In a specific embodiment, the support specifically binds about $1.2 \times 10^{-2}$ to about $9.9 \times 10^{-2}$ micromoles of biotin per square meter of support. In various embodiments, the support comprises biotin attached to the support (directly or through a support coupler) associated with a biotin-binding moiety, such as, for example, SA, and the foregoing biotin binding capacities refer to the ability of the biotin-binding moiety (e.g., SA) to bind free biotin.

Unless otherwise stated, or implicit from the disclosure, any of the embodiments described in connection with any particular method or composition described herein can be used in conjunction with any of the other embodiments described herein.

BRIEF DESCRIPTION OF THE FIGURES

FIG. 10, in panels A and B, illustrates the increased bindable surface area associated with using a dispersion step of the invention.

FIG. 12 shows data in table format for process reproducibility (manufacturability) studies of Example 6.

FIG. 13 shows data in table format for further process reproducibility (manufacturability) studies of Example 6.

FIG. 14A shows data in table format for the enhanced stability studies of Example 7.

FIG. 14B is a continuation of the table of FIG. 14A, showing the data for enhanced stability studies of Example 7.

FIG. 16A shows data in table format for actual binding surface density calculations of Example 11, for various lots of microparticles prepared in accordance with embodiments of the invention.

FIG. 16B shows data in table format for actual binding surface density calculations for microparticles prepared in accordance with embodiments of the invention, derived from microparticle data using a roughness assumption.

FIG. 16C shows further data in table format for binding surface area calculations assuming a smooth support surface, for various lots of microparticles prepared in accordance with embodiments of the invention.

FIG. 16D shows data in table format for binding surface density calculations assuming a smooth support surface prepared in accordance with embodiments of the invention, derived from microparticle data.

DETAILED DESCRIPTION

Figure 1A:
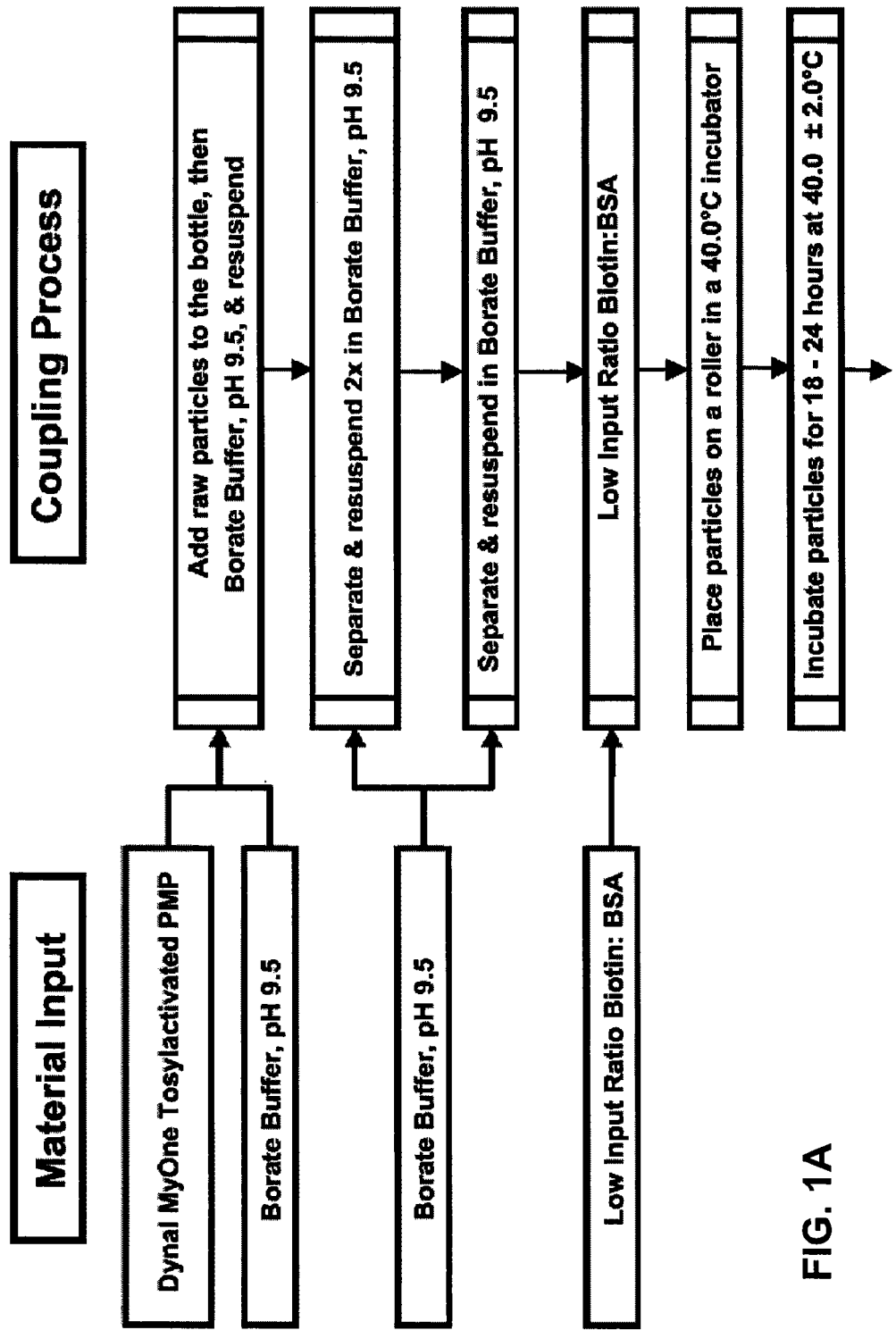
FIG. 1A illustrates a process of preparing a non-saturated and orientated SA on a paramagnetic microparticle (PMP) binding surface.

The present invention is based at least in part on the realization that designing binding surfaces: (a) by associating a less than saturating amount of ligand yields capture moiety-containing complexes that are sparsely dispersed across the binding surface of the support in an accessible spatial orientation, and optionally (b) by tandemly positioning ligands and, in turn, other component moieties of the capture moiety-containing complexes, in a linear or near-linear structural (physical) orientation, can result in binding surfaces with more desirable qualities for conducting assays, such as affinity assays (e.g., immunoassays or nucleic acid assays), than designing binding surfaces by simply crowding the support surface by increasing the density of ligands.

Conventional approaches for making binding surfaces are typically aimed at maximizing the amount of ligand per unit area of the support without regard to the accessibility and/or orientation of the ligands, frequently resulting in crowding of ligands on the support. Maximizing ligand per unit area on a binding surface can lead to degradation in performance of the binding surface due at least in part to steric effects. Performance degradation can also result from sloughing of excess ligand from the binding surface.

As used herein, coupled with, or its grammatical equivalents, means a covalent or non-covalent binding or interaction between two moieties. The term coupled with is not intended to connote an orientation or direction of the coupling.

As used herein, the term "fusion protein" encompasses recombinant proteins (such as chimeric proteins), hybrid proteins, and synthetically-derived proteins. Its usage is well known in the art.

Non-saturated or non-saturated and orientated binding surfaces in accordance with the invention include binding surfaces that are constructed by coupling less than a saturating amount of ligand on a support (for example, by attaching directly to the support or by attaching to a support coupler that is attached to the support). A binding surface that is "non-saturated" with respect to ligand is a binding surface that has a sub-maximal density of ligand per unit surface area of support, or a sub-maximal density of ligand per unit weight of support. In a specific embodiment of the present invention, the ligands of the non-saturated binding surface are spacially orientated. As used herein, the term spacially orientated, or its gramatical equivalents, refers to moieties that are spread out over distance or area. In other words, the moieties are orientated or spaced on the support surface such that they are substantially not touching the nearest neighbor.

A "sub-maximal" density of ligand per unit surface area of support refers to a binding surface that is not saturated with respect to the number of ligands that can be present on the support surface. For example, a support surface that is saturated with ligands has the maximal percentage of ligand that can be placed on a support surface under a given set of conditions, represented by 100% (e.g., a given ligand::support coupler complex, wherein the support coupler is saturated with ligand, and the complex is disposed at its highest possible density on a support under conditions that promote maximal attachment of ligand::support coupler complex to the support.

Non-saturated or non-saturated and orientated binding surfaces can be particularly desirable for binding surfaces employed in immunoassays. Most immunoassays employ a binding surface on a support. In many of these applications, the support is a microparticle or a microtiter plate, where the moiety that captures the analyte, for example, an antigen, is built up on other molecules to form capture moiety-containing complexes that bind analyte. One nonlimiting example of this is an immunoassay having an immunoglobulin immobilized on a microparticle. The immunoglobulin may be immobilized directly on the support, or the immunoglobulin may be coupled (e.g., covalently) to other molecules that are, in turn, immobilized on the support. Preparing a non-saturated binding surface is described herein for both situations. Detailed examples are provided for the situation where an immunoglobulin, or fragment thereof, is not directly attached to the support, but is instead associated with other moieties that are attached to the support.

The term "coupled" includes (a) covalent binding (e.g., through one or more carbon-carbon bonds, carbon-nitrogen bonds, carbon-oxygen bonds, etc., either directly or indirectly), and (b) non-covalent binding (either indirectly or directly).

Entities that are known to specifically interact with one another can be covalently coupled. One non-limiting example of entities that are known to specifically interact and that can be covalently coupled is an antigen and its specific antibody, which can be made to covalently attach through, for example, coupling chemistry.

Entities that do not specifically interact with one another can be covalently coupled. One non-limiting example of entities that are not known to specifically interact with one another and that can be covalently coupled is SA and BSA, which can be made to covalently attach through, for example, coupling chemistry.

Examples of non-covalent binding include, affinity, ionic, van der Waals (e.g., dipole/dipole or London forces), hydrogen bonding (e.g., between polynucleotide duplexes), and hydrophobic interactions. Where association is non-covalent, the association between the entities is preferably specific. Non-limiting examples of specific non-covalent associations include the binding interaction between biotin and a biotin-binding protein such as avidin, SA, neutravidin, a fragment of SA, a fragment of avidin, a fragment of neutravidin, or mixtures thereof; the binding of a biotinylated Fab, a biotinylated immunoglobulin or fragment thereof, a biotinylated small molecule (such as, for example, a hormone or a ligand of a receptor), a biotinylated polynucleotide, a biotinylated macromolecule (e.g., a protein or a natural or synthetic polymer) to a biotin-binding protein such as avidin, SA, neutravidin, a fragment of SA, a fragment of avidin, a fragment of neutravidin, or mixtures thereof; the binding of a substrate to its enzyme; the binding of a glycoprotein to a lectin specific for the glycoprotein; the binding of a ligand to a receptor specific for the ligand; the binding of an antibody to an antigen against which the antibody is raised; and duplex formation between a polynucleotide and a complementary or substantially complementary polynucleotide; etc.

Particular examples are provided for a microparticle having biotinylated protein (ligand::support coupler complex) attached to the microparticle, wherein the biotinylated protein is coated with SA (biotin-binding moiety), and the SA-biotinylated protein-coated microparticle is then coated with a biotinylated immunoglobulin or biotinylated fragment thereof (biotinylated capture moiety) which is used to capture an analyte in an assay, or to bind another immunoglobulin or fragment thereof which is used to capture an analyte in an assay (e.g., biotinylated Goat×Mouse IgG is used to capture a Mouse IgG×Antigen1, which is used to capture Antigen1). The non-saturated nature of the biotinylated protein on the support surface is reflected in the SA coating, which is also non-saturated by virtue of the non-saturated nature of the biotin with which it associates, which results in non-saturation of the biotinylated immunoglobulin (or biotinylated immunoglobulin fragment) that captures the analyte, or non-saturation of the biotinylated immunoglobulin (or biotinylated immunoglobulin fragment) that captures the additional immunoglobulin or fragment that captures the analyte.

In various embodiments of the present invention, the ligand can be covalently bound to the support coupler or non-covalently bound to the support coupler. In a specific embodiment, the ligand is covalently bound to the support coupler and the ligand binder is at least bivalent. In a further specific embodiment, the ligand is biotin and is covalently bound to the support coupler and the ligand binder is an at least bivalent moiety, such as streptavidin, avidin, or neutravidin, a fragment of streptavidin, a fragment of avidin, a fragment of neutravidin, or mixtures thereof. In embodiments where the ligand binder is at least bivalent, covalently coupling the ligand to the support coupler can result in a more stable binding surface, as sloughing off of excess ligand is reduced or abolished.

In other embodiments, covalently coupling of the ligand to the support coupler is optional. For example, where the ligand is an antibody fragment with a single binding site, the ligand can be non-covalently coupled with the support coupler.

Accordingly, the invention comprises methods and compositions for providing a non-saturated amount of a capture moiety for an immunoassay, wherein the capture moiety is non-saturated by virtue of binding to a non-saturated support surface. In various embodiments, the capture moiety can be used to capture further capture moieties. For example, a support coated with biotin-BSA (ligand::support coupler complex), coated with SA (ligand binder), which is coated with a biotinylated Goat×Mouse IgG can be further coated with, for example, a Mouse IgG×TSH, which can then be used to capture TSH analyte.

Density of components on a support surface can be expressed in a variety of ways. For particulate supports, such as, for example, microparticles, it is convenient to discuss density of a component of the binding surface in terms of the unit weight of the microparticle, for example, micromoles of the component (for example, ligands, such as biotin; ligand binders, such as SA; capture moieties, such as analyte-specific biotinylated IgG; etc.) per mg of microparticles. For non-particulate supports, such as, for example, microtiter plates, it is convenient to discuss density of the component in terms of surface area of the support, such as, for example, micromoles of ligand binder per square meter. The density of the component on a support surface can be expressed for a ligand (e.g., the biotin of the biotin-BSA microparticles of the Examples, in terms of biotin binding) or any other component built on the support surface (e.g., in the biotin-BSA microparticles of the Examples, in terms of SA bound with the microparticle, or analyte-specific biotinylated immunoglobulin bound with the SA).

Due to the less than saturating amount of the ligand that is coupled with (directly, or indirectly through, for example, a protein) the support, successive layers of ligand binders will be non-saturated, and the density of the ligand binders above the layer of the ligand attached to the support will comprise a successively smaller density (e.g., successively smaller micromoles per mg of microparticle, or micromoles per square meter). Thus, for the example of a biotinylated microparticle in accordance with the invention, the density of SA on the support surface will be lower than the density of the BSA support coupler, which will be lower than the density of the biotin ligand (estimated before addition of SA) on the support surface.

Accordingly, in various embodiments for a particulate support such as a microparticle of about 1.0 micron in diameter, or for a non-particulate support (for example, a microtiter plate), wherein the support coupler is significantly larger than the ligand (e.g., an albumin support coupler has a M.W. of about 66,000 Da, and a biotin ligand has a M.W. of about 244 Da), the density of the ligand binder (e.g., SA) is about 10% to about 90% less than the density of the ligand::support coupler complex (e.g., biotin-BSA), in various embodiments about 30% to about 70% less than the density of the ligand::support coupler complex, and in various embodiments about 40% to about 60% less than the density of the ligand::support coupler complex. In a specific embodiment, the ligand binder comprises a biotin-binding moiety, such as, for example, SA, and the ligand comprises biotin coupled with a support coupler, such as, for example BSA or ovalbumin or mixtures thereof, or a fragment of BSA or ovalbumin or mixtures thereof.

In various embodiments a capture moiety, attached to a ligand binder, where the ligand binder is in turn associated with a ligand, is also non-saturated. The density of the capture moiety on the microparticle or the nonparticulate support in various embodiments is about 10% to about 90% less than the density of the ligand binder, in various embodiments about 30% to about 70% less than the density of the ligand binder, and in various embodiments about 40% to about 60% less than the density of the ligand binder.

Another way of expressing the level of saturation is in comparison to the maximal amount of ligand that can be coupled with a support. In various embodiments, a support surface that is non-saturated with respect to the ligand will have less than 100% of ligand coupled. For example, the percentage of ligand on the support surface can be about 10% to about 90% of the maximal amount of ligand that can be placed on the support surface. Or the percentage of ligand on the support surface can be about 20% to about 80% of the maximal amount of ligand that can be placed on the support surface. Or the percentage of ligand on the support surface can be about 30% to about 70% of the maximal amount of ligand that can be placed on the support surface. The optimal percentage of ligand on the support surface (with the maximal number of ligands being 100%) is the percentage (or percentage range) of ligand that provides the best signal-to-noise ratio, the lowest dissociation of ligand from the binding surface, the most stability (at the temperature(s) relevant to the application), and a relatively low variance in validation studies as compared to conventional binding surfaces (e.g., less than 10%, more preferably 5% or less). As explained elsewhere in the present application, the support coupler is optional. For example, the ligand can be biotin, or a derivative thereof, that is coupled with the solid phase support surface.

Due to the less than saturating amount of ligand that is coupled with (directly, or indirectly through, for example, a protein) the support, successive layers of ligand binders and capture moieties will be non-saturated, and the density of the successive layers of ligand binder and capture moiety above the layer of the ligand coupled with the support will comprise successively smaller densities (e.g., successively smaller micromoles per mg of microparticle, or micromoles per square meter). Thus, for the example of a biotinylated microparticle in accordance with the invention, the density of the biotinylated IgG (biotinylated capture moiety) on the support surface will be lower than the density of the SA (biotin-binding moiety), the density of the SA on the support surface will be lower than the density of the BSA support coupler (biotin-BSA), which will be lower than the density of the biotin (biotin-BSA; biotin density estimated before addition of SA) on the support surface.

In a specific embodiment, the surface comprises biotin (biotin-BSA) at a density of about $1 \times 10^{-5}$ to about $5 \times 10^{-2}$ micromoles of biotin per mg of microparticles, or alternatively at a density of about $1.6 \times 10^{-4}$ to about $4.9 \times 10^{-4}$ micromoles of biotin per mg of microparticles. In other embodiments, the surface comprises BSA (biotin-BSA) at a density of about $1.6 \times 10^{-4}$ to about $4.9 \times 10^{-4}$ micromoles of BSA per mg of microparticles, comprises SA at a density of about $1.0 \times 10^{-4}$ to about $1.4 \times 10^{-4}$ micromoles of SA per mg of microparticles, or comprises biotinylated IgG at a density of about $2.1 \times 10^{-5}$ to about $4.1 \times 10^{-5}$ micromoles of biotinylated IgG per mg of microparticles. In a specific embodiment, a rough support surface comprises biotin (biotin-BSA) at a density of about $1.9 \times 10^{-2}$ to about $6.6 \times 10^{-2}$ micromoles of biotin per square meter, comprises BSA (biotin-BSA) at a density of about $1.6 \times 10^{-2}$ to about $2.9 \times 10^{-2}$ micromoles of BSA per square meter, comprises SA at a density of about $1.2 \times 10^{-2}$ to about $1.9 \times 10^{-2}$ micromoles of SA per square meter, and comprises biotinylated IgG at a density of about $2.5 \times 10^{-3}$ to about $5.5 \times 10^{-3}$ micromoles of biotinylated IgG per square meter.

A support comprising a non-saturated or non-saturated and orientated binding surface employing any ligand can be prepared in accordance with the methods and compositions herein. For example, an oligonucleotide- or polynucleotide-binding surface can be non-saturated by binding (directly or through a support coupler) an oligonucleotide or polynucleotide to a surface at two or three or four or more selected input ratios of oligonucleotide or polynucleotide to support or support coupler. A convenient input ratio to begin with is an input ratio known in the art, and then decrease the input ratio in steps (e.g., by half, by an eighth, by a sixteenth, etc.), since input ratios known in the art are generally selected to maximize the amount of ligand on a support surface. Once the oligonucleotide or polynucleotide is attached to the support surface, efficiency of binding can be measured using any suitable method known in the art (e.g., quantitation of bound fluorescence for a fluorescent oligonucleotide or polynucleotide complementary to the ligand oligonucleotide or polynucleotide). A suitable input ratio of ligand oligonucleotide or polynucleotide to support coupler or support is determined by measuring the amount of signal generated by the surface (for example, by the fluorescent bound complementary oligonucleotide or polynucleotide) for a fixed amount of binding surface (for example, grams of 1 micron microparticle coated with the oligonucleotide or polynucleotide ligand). Desirable level of saturation is obtained where the ratio of the amount of signal to the weight of the microparticle (all other variables approximately constant) is highest. This general procedure can be used for assessing the desired level of saturation on any desired binding surface. As used herein, an oligonucleotide is a nucleic acid of about 30 bases in length or less and a polynucleotide is a nucleic acid of about 30 bases in length or more.

The optimal percentage of ligand on a binding surface for a given application can be determined by one of skill in the art by using the same kind of methods described herein for biotin-based applications. For example, if an oligonucleotide or polynucleotide is employed as a ligand in place of biotin, the oligonucleotide or polynucleotide can be coupled with a support coupler (e.g., a protein or nucleoprotein), and a suitable solid phase can be coated with the oligonucleotide or polynucleotide and its support coupler. Stability, sloughing or dissociation, signal-to-noise, and validation studies can be carried out analogous to those described herein to obtain the optimal amount of ligands per unit surface area of the binding surface (e.g., 10% to 90% of maximal, 20% to 80% of maximal, 30% to 70% of maximal, etc.). One convenient approach would be to first maximize the amount of oligonucleotide or polynucleotide per unit surface area, and then employ the methods described herein (e.g., at several low molar input ratios of oligonucleotide or polynucleotide to support coupler in preparing ligand::support coupler complexes) to prepare a non-saturated and orientated surface, and compare stability, dissociation, signal-to-noise, and validation results from the various preparations.

Orientating a ligand on a binding surface includes physically orientating the ligand, ie. adjusting the placement of the ligand with respect to its surroundings. A binding surface that contains a maximal amount of ligands per support coupler generally results in many ligands that are not sterically accessible and competition among closely spaced adjacent ligands for incoming molecules of interest for binding to the ligands of the complex. As used herein, physical (structural) orientation, or its gramatical equivalents, means that a moiety is manipulated in a manner such that the majority of moieties are orientated to face in a particular direction. In an embodiment of the present invention, the moiety is orientated so that the recognition site or binding site is substantially orientated away from the support surface. In another embodiment of the invention, the physically orientated moieties are tandemly associated.

Orientating can be achieved by the methods herein for any ligand::support coupler pair. One method of orientating a ligand on a binding surface is to prepare ligand::support coupler complexes (examples of biotin-BSA complexes are provided herein) at low molar input ratios of ligand to support coupler. As described elsewhere herein, the goal of using low molar input ratios of ligands to support couplers is to make complexes with a controlled number of ligands coupled per support coupler. Achieving a controlled (i.e., sub-maximal) number of ligands per support coupler can lead to better steric accessibility of the ligands on the surface, less interaction between adjacent ligands, more uniform distance (on average) between ligands on the binding surface, and improved stability by providing a surface that is substantially free of free ligand (e.g., prevent or mitigate sloughing of ligand).

The compositions and methods of the invention include improvements to assay performance parameters comprising sensitivity (signal-to-noise ratio), accuracy, assay precision (quantitative assays), assay reproducibility (qualitative assays), and stability, and to assay manufacturing parameters such as paramagnetic microparticle (PMP) manufacturing process reproducibility (PMP manufacturability), or combinations thereof. Included in the invention are compositions and methods for: non-saturated or non-saturated and orientated biotin conjugated molecules used in affinity assays (e.g., non-saturated or non-saturated and orientated biotinylated antibody used as the solid phase capture antibody in sandwich and competitive assays); reduction in assay noise or background associated with nonspecific binding or heterophile interference; increased assay signal due to enhanced microparticle dispersion (increased available surface area and collision rates; decreased assay diffusion distance); increased assay signal due to SA non-saturation or non-saturation and orientation (steric freedom to bind large and small biotin-conjugated molecules, improving binding efficiency); increased assay signal due to non-saturation or non-saturation and orientation of biotin-conjugated molecules (steric freedom to capture or bind large or small analyte binders (biotinylated capture moieties) and/or analytes, improved analyte binder (biotinylated capture moiety) and/or analyte recognition and analyte binder (biotinylated capture moiety) specific activity); enhanced product stability (improved blocking efficiency and decreased SA sloughing from surface); and/or increased immunoassay robustness and process reproducibility due to process optimization used to prepare non-saturated or non-saturated and orientated SA on a microparticle surface. In various embodiments, signal-to-noise ratio on a non-saturated or non-saturated and orientated support surface can be enhanced by titering different levels of ligand binder (e.g., SA) to ligand (e.g., biotin), and/or titering different levels of capture moiety (e.g., biotinylated antibody) to ligand binder (e.g., SA), in order to achieve an optimal signal-to-noise ratio.

In an embodiment based on a microparticle coated with low input ratio biotinylated BSA, blocked with the block copolymer Pluronic® F108 (available from BASF), dispersed with Pluronic® F108, and coated with SA, the optimal signal-to-noise ratio and IgG binding capacity in immunoassays are obtained using biotinylated antibody inputs from 3 to 6 micrograms of biotinylated IgG per mg of microparticles. There is no significant change in signal-to-noise ratio of IgG binding capacity with IgG inputs greater than 10 micrograms of biotinylated IgG per mg of microparticles. IgG inputs less than 3 micrograms of biotinylated IgG per mg of microparticles result in a significant decrease in signal-to-noise ratio and IgG binding capacity, and approach zero as the antibody input approaches zero.

Although the discussion and examples herein, and associated figures, present embodiments of the invention employing biotin as a ligand, the invention is not limited to binding surfaces having biotin. What is described herein can be generalized to any binding surface whose ligands can be non-saturated or non-saturated and orientated using the methods and compositions described. The description that follows of binding surfaces having biotin as ligand is used to illustrate certain compositions and methods for making non-saturated or non-saturated and orientated binding surfaces.

Moreover, as explained elsewhere in this specification, the support coupler is optional. Thus, the support coupler is but one embodiment of the invention and the description of the support coupler is not intended to be limiting of the present invention.

Binding surfaces comprising non-saturated and orientated ligands are provided. The binding surfaces can be used to build a surface of capture moieties suitable for capturing any molecule of interest. The non-saturated nature and orientation of the ligands on the surface allows placement of further components, such as capture moieties, whose disposition on the binding surface reflects the non-saturated nature and orientation of the underlying ligands.

Ligand::support coupler complexes are provided that, in various embodiments, are made employing a low molar input ratio of ligand to support coupler such that there are a sub-maximal number of ligands disposed on the support coupler in accordance with the methods described herein, and such that sloughing is reduced. These complexes can be used to create a non-saturated and orientated binding surface of the invention. Embodiments that use a low input ratio of ligand to support coupler in making the ligand::support coupler complex can be particularly useful where bi- or multivalent ligand binders are employed (such as, for example, where biotin is a ligand and a bi- or multivalent biotin-binding protein such as SA is the ligand binder).

Dispersion agents and methods for making microparticles comprising binding surfaces are provided, as well as methods for making microparticles with binding surfaces, for example, employing block copolymers such as Pluronic® block copolymers in dispersing microparticles coated with biotin (ligand) before adding biotin-binding moieties such as SA (ligand binder). Specific Pluronic® block copolymers that may be used here, and their number average molecular weights, include F108 (about 12,700-17,400 Da, average of about 14,600 Da) and F127 (about 9,840-14,600 Da, average of about 12,600 Da). Block length of each Pluronic® described herein is approximate, according to the manufacturer, since exact block length will vary with batches. Unless otherwise specified or apparent from the context, molecular weights of block copolymers are expressed as number average molecular weights.

Methods are presented for making stable biotinylated molecules (e.g., biotin-BSA and biotin-ovalbumin) for use in coating surfaces used to capture molecules that have two or more biotin-binding domains (e.g., avidin, SA, and neutravidin). These are, in turn, useful for binding biotinylated capture moieties that can capture other molecules of interest in binding assays (e.g., for biotinylated antibodies, the molecules of interest are antigens; for biotinylated small molecules, the molecules of interest can be enzymes, antibodies, or binding proteins that bind the small molecules; etc.). Particular examples are provided that employ low input ratio biotinylated BSA prepared by using a low molar input ratio of biotin when biotinylating BSA, for use in coating a support to capture SA. The SA can then be complexed to a suitable biotinylated capture moiety.

Methods are presented for coating biotinylated molecules onto a support to capture, orientate, and associate less than a saturating amount of a molecule having two or more biotin-binding domains (e.g. avidin, SA, or neutravidin). Particular examples are provided that illustrate a low molar input ratio biotin-BSA coating on a PMP surface used to capture, orientate, and associate less than a saturating amount of SA.

Methods are presented that use block copolymers as blocking agents for supports coated with biotinylated and/or non-biotinylated molecules. Particular examples are provided that illustrate using the tri-block copolymer Pluronic® F108 as a blocking agent for PMPs coated with low input ratio biotin-BSA.

Methods are presented for using block copolymers as dispersion agents for microparticles coated with biotinylated and/or non-biotinylated molecules. Particular examples are provided that illustrate the use of Pluronic® F108 as a dispersion agent for PMPs coated with low input ratio biotin-BSA.

Methods are presented for using block copolymers as dispersion agents for microparticles coated with biotinylated molecules, during the coating of molecules containing two or more biotin-binding domains (e.g., avidin, SA, and neutravidin). Particular examples are provided that illustrate using Pluronic® F108 as a dispersion agent during the coating of SA on the surface of PMPs coated with low input ratio biotin-BSA (e.g., adding Pluronic® F108 to make a monodispersion of low input ratio biotin-BSA microparticles before adding SA).

Methods are presented for coating, orientating, and associating less than a saturating amount of a molecule comprising two or more biotin-binding sites (e.g., avidin, SA, or neutravidin) to a biotinylated surface. Particular examples are provided that illustrate coating, orientating, and associating less than a saturating amount of SA on the surface of PMPs coated with low input ratio biotin-BSA.

Methods are presented for associating less than a saturating amount of, and optionally orientating, biotin-conjugated molecules onto a surface. Particular examples are provided that illustrate coating, orientating, and associating less than a saturating amount of biotin-containing conjugates (e.g., biotinylated antibodies, Fab fragments, small molecules, large molecules, carrier molecules, etc.) on the surface of PMPs specifically coated with SA (i.e., non-saturated and orientated) for use in affinity assays such as, for example, immunoassays.

Affinity assays include assays that determine the presence or absence of an analyte in a sample, and/or quantitate the amount of analyte in a sample, directly or indirectly, based on a specific or relatively specific interaction between the analyte and a molecule that preferentially binds the analyte. Affinity assays include assays that rely in at least some respect on a specific or relatively specific binding affinity of one entity for another. Affinity assays include, but are not limited to, assays that rely on a binding interaction between a receptor and a ligand, an enzyme and its substrate, a polynucleotide and its complement or substantial complement, a small molecule and a binding protein that binds the small molecule with specificity, etc. Immunoassays include assays that rely on the interaction between, for example, an antigen and an antibody that recognizes the antigen. Immunoassays also include, for example, assays that employ an antibody or fragment thereof to bind an antigen of interest in a sample. Affinity assays also include, for example, competitive assays and sandwich assays. Such assays include those which rely on an interaction of a surface-bound antigen to detect an antibody of interest in a sample, and those which rely on an interaction of a surface-bound antibody or fragment thereof to detect an antigen of interest in a sample. As used herein, antigens are not limited to polypeptides or proteins, but can also include small molecules (such as, for example, haptens) and antibodies (for example, antibodies can be used as antigens to generate other antibodies that recognize them). In general, antigen as used herein includes any analyte of interest in a sample immunoassayed with an antibody or fragment thereof using the compositions or methods of the invention.

Figure 1B:
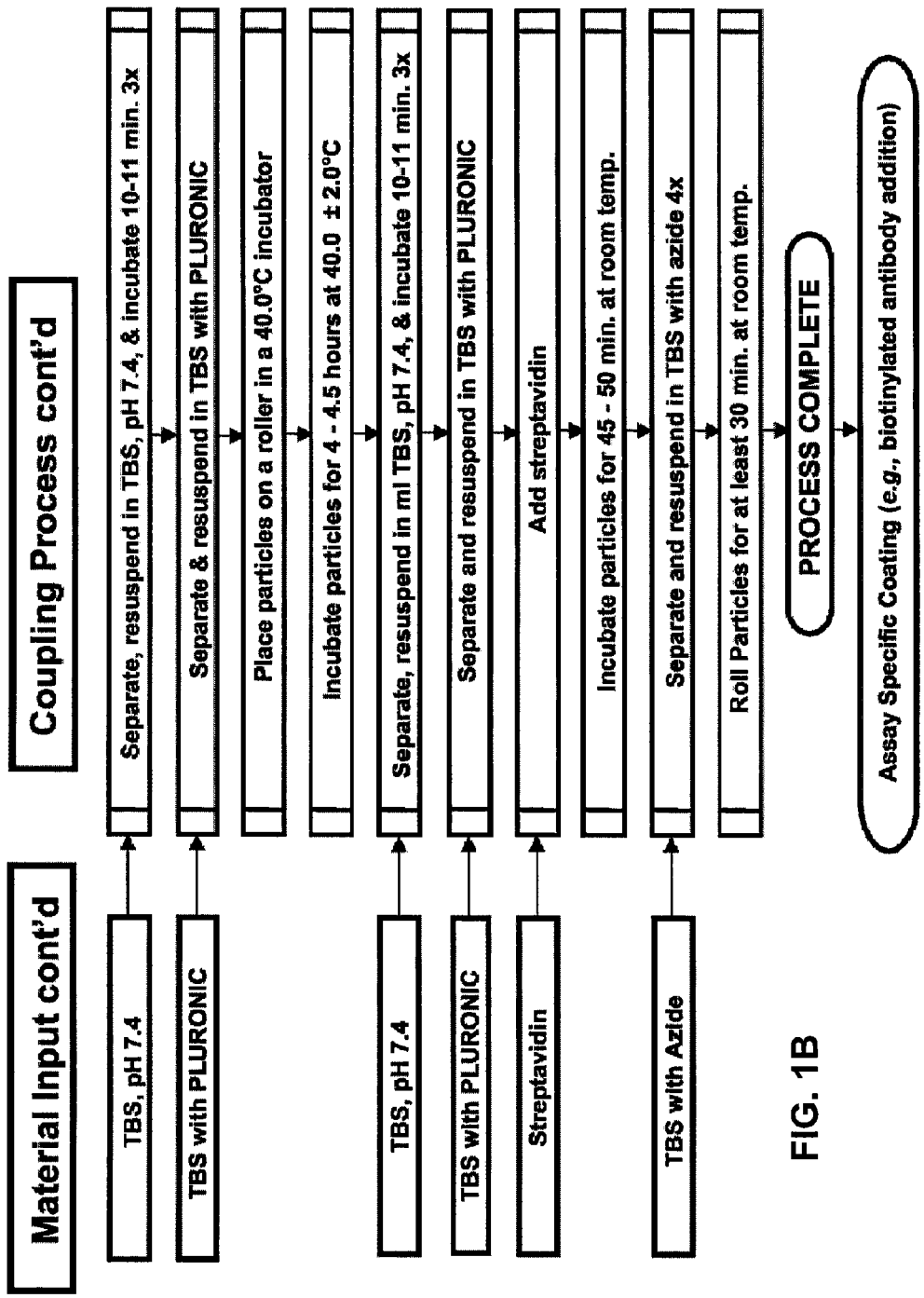
FIG. 1B is a continuation of the process illustration of FIG. 1A.
Figure 2:
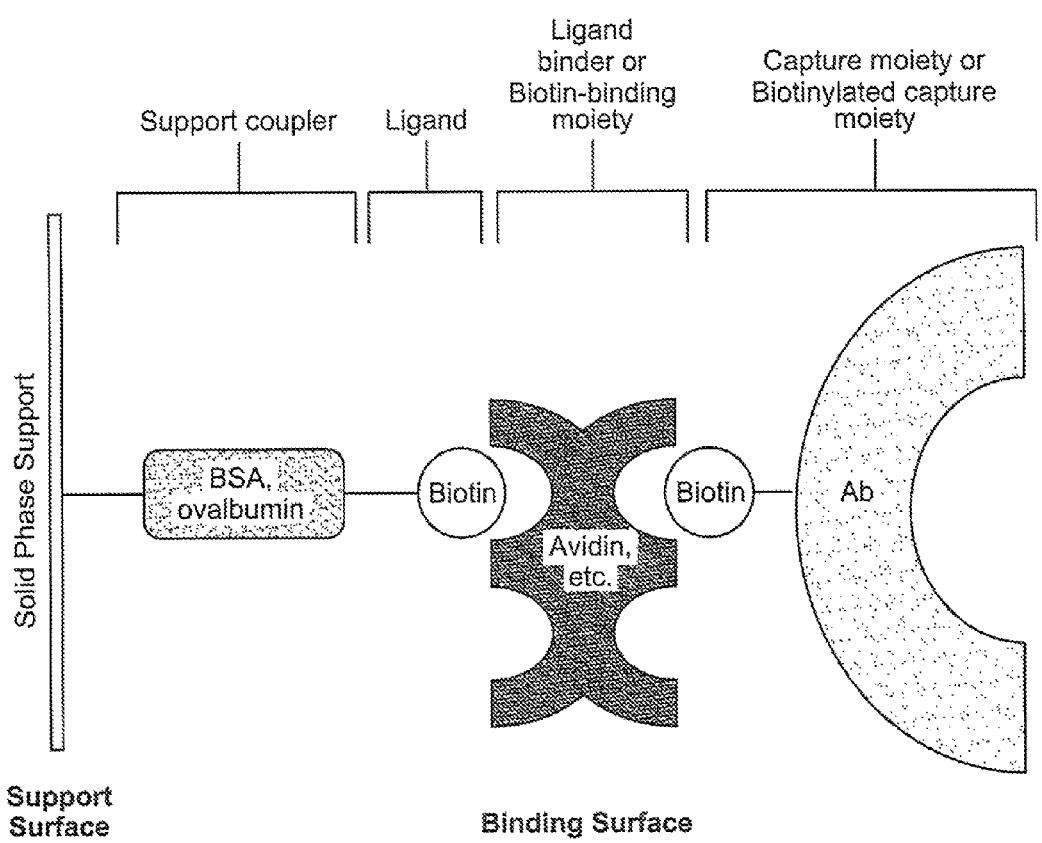
FIG. 2 illustrates an embodiment of the invention comprising a solid support surface; BSA or ovalbumin covalently attached to the support surface; biotin covalently attached to the BSA or ovalbumin; streptavidin, neutravidin or avidin associated with the biotin; and a biotinylated antibody associated with the streptavidin, neutravidin, or avidin.

An application of certain embodiments of the compositions and methods described herein is presented in FIGS. 1A and 1B for the particular case of orientating and associating less than a saturating amount of SA on a PMP surface. A more detailed explanation of various steps in this process is provided elsewhere herein.

A general description of a process of making a non-saturated and orientated surface is provided for the case of a surface comprising biotinylated BSA, capable of binding SA, which, in turn, is capable of binding a biotinylated capture moiety such as, for example, an immunoglobulin or fragment thereof. Much of the discussion and examples provided discuss a biotin/SA system, although the invention is not limited to biotinylated surfaces.

It should be kept in mind that because the discussion and examples employ biotin, and biotin is typically employed to bind a bi- or multivalent biotin-binding moiety (such as, for example, SA), the fact of employing a multivalent biotin-binding moiety presents certain issues that may not be encountered with many binding surfaces that do not employ a multivalent ligand binder. One of these issues is that when using a biotinylated microparticle coated with SA, sloughing of noncovalently bound biotin can interfere with the performance of the binding surface (e.g., free biotin can dissociate and complex with the SA). In such a case, this phenomenon can be reduced by conducting a low input ratio biotinylation of the BSA, rather than biotinylating BSA with an arbitrarily large excess of biotin, because low input ratio biotinylation can reduce the amount of noncovalently bound biotin that associates with the BSA.

Also, when coating a support with a multivalent moiety such as SA on a microparticle, aggregation can occur during coating with SA. This is because each molecule of SA binds more than one molecule of biotin. SA is a tetrameric protein with a molecular weight of approximately 56,000 Da, and it is a specific example of a biological molecule that has two or more biotin-binding domains. The avidin-biotin interaction is the strongest known non-covalent interaction between protein and ligand, and each of the four subunits of SA can bind biotin with a binding constant $K_a=10^{15}$ $M^{-1}$. The tertiary structure of SA results in its four biotin-binding domains being located on opposite sides of the molecule. If one of the SA biotin-binding domains binds to a biotinylated surface, at least two of the three unoccupied biotin-binding domains will still be sterically available to bind biotinylated capture moieties. Avidin and neutravidin are other examples of tetrameric proteins that have four biotin-binding domains; they differ from SA in their pI, solubility, and nonspecific binding properties.

When the biotinylated surface is exposed to SA, free SA will bind with the biotin of the surface, but SA bound with the surface can then bind biotin bound with another microparticle. In this way, large microparticle aggregates can form. This can be addressed by creating a monodispersion of microparticles at the SA addition step.

Briefly, the process for making a biotin-BSA surface on a microparticle begins with low input ratio biotinylation of BSA. Low input ratio biotinylated BSA is then coupled with PMPs by covalent attachment of the primary amines of the BSA of biotin-BSA to the surface functional groups of the PMPs. The resulting biotinylated PMPs are suspended in a suitable Pluronic® for a time (blocking step), rinsed, and then isolated. Next, the biotinylated PMPs are suspended in a suitable Pluronic® (an enhanced dispersion step), and SA is added. The microparticles are incubated at room temperature for a time, rinsed, and then isolated. Once isolated, suitable biotinylated molecules (such as biotinylated capture moieties) can be added for any particular assay application.

The aforementioned blocking step using a suitable Pluronic® minimizes non-specific, artifactual binding events involving the otherwise unoccupied binding sites of the non-saturated binding surface of the invention (FIGS. 5 and 7) while allowing the specific associations required to generate the ligand-based complexes of the invention. Such blocking promotes spatial (steric) accessibility of the ligand-based complexes of the invention as their moieties associate and facilitates a linear structural orientation of each ligand-based complex of the invention as it is formed, thereby increasing the likelihood that each resulting capture moiety-containing complex of the invention functions to optimize assay performance parameters which include, as an example that is not intended to be limiting, signal-to-noise ratio. Moreover, and as is true for immunoassays generally, a blocking step also minimizes nonspecific binding that may be described as artifactual binding events in an immunoassay involving its components and/or support surfaces that yield undesirable byproducts which can adversely affect assay performance parameters including, as a non-limiting example, signal-to-noise ratio. The adverse effects of such artifactual binding events on signal-to-noise ratio can take the form of reduced signal, increased noise, or both. Lastly, since specific associations with both the support surface and the binding surface are optimized, whereas non-specific associations with these surfaces are minimized, sloughing of ligand-based components of the invention from the support and binding surfaces of microparticles or microplates is concomitantly minimized. For such reasons, the blocking step with a suitable Pluronic® results in performance and manufacturing improvements that favorably affect assay sensitivity (signal-to-noise ratio), assay accuracy, assay precision (quantitative assays), assay reproducibility (qualitative assays), assay stability, or PMP manufacturing process reproducibility (PMP manufacturability), or combinations thereof.

The aforementioned enhanced dispersion step using a suitable Pluronic® prior to SA addition, during the process of making a biotin-BSA surface on a microparticle, mitigates microparticle aggregation and concomitantly increases the surface area that is exposed on a microparticle (FIGS. 6 and 10), thereby rendering the least number of ligand-based complexes on a microparticle surface unavailable for binding. Such Pluronic®-mediated inhibition of aggregation is useful for applications that include, but are not intended to be limited to, enhancing PMP manufacturability (PMP process reproducibility) and improving the performance of assays and kits in which such PMP are used. PMP manufacturability is enhanced when the level of microparticle aggregation from lot to lot of PMP is controllable before, during, and after a PMP manufacturing process. After the PMP manufacturing process, the performance of assays using such PMP may be optimized by means that include, but are not intended to be limited to, exposing microparticles to a solution containing Pluronic® prior to the addition of sample during an immunoassay and/or exposing microparticles to a solution containing Pluronic® prior to the addition of substrate during an immunoassay. For such reasons, the enhanced dispersion step with a suitable Pluronic® results in performance and manufacturing improvements that favorably affect assay sensitivity (signal-to-noise ratio), assay accuracy, assay precision (quantitative assays), assay reproducibility (qualitative assays), assay stability, or PMP manufacturing process reproducibility (PMP manufacturability), or combinations thereof.

The process is illustrated in FIGS. 1A and 1B for certain embodiments that employ uniform size (<5% CV) 1.0 µm MyOne™ tosylactivated (no further surface activation required) Dynal® PMP (Invitrogen Corporation), low input ratio (4 biotin reagent:1 BSA) biotinylated BSA, Pluronic® F108 tri-block copolymer (synthetic, non-biological; BASF), SA21 SA-PLUS™ (frozen, never lyophilized; ProZyme®), magnets to separate and wash the microparticles (buffer exchange). A microparticle process involves concentration of 25 mg PMP/mL, overhead mixing and sonication to resuspend and disperse the microparticles for process resuspensions, overhead mixing for process incubations, elevated temperature (38-42° C.) and room temperature process incubations, tosyl chemistry to covalently couple the biotinylated BSA to the microparticle surface tosyl groups via BSA primary amino groups, Pluronic® F108 tri-block copolymer for microparticle surface blocking (removing passively absorbed protein, minimizing non-specific binding of proteins to the microparticle surface), Pluronic® F108 tri-block copolymer for PMP monodispersion, and secondary coupling (affinity) of the SA to the biotin-BSA PMP intermediate in the presence of the Pluronic® F108 tri-block copolymer (mitigates microparticle aggregation during the SA coupling process).

A convenient way to view the principle behind low input ratio biotinylation in making non-saturated or non-saturated and orientated surfaces is to view the biotinylation process through the lens of a Poisson distribution. The principles underlying the illustration that follows are applicable to all ligand and support coupler pairs (not just biotin and BSA). The ligand::support coupler complex prepared using a low input ratio of ligand to support coupler is believed to result in a more favorable orientation of ligand molecule when the ligand support coupler is coated on a support. This more favorable orientation of ligand molecules contributes to the steric accessibility of the coating on the support. For illustration of the principle only, and not by way of limitation to any particular support coupler or ligand, the phenomenon is illustrated using biotinylated BSA herein. The illustration below applies to any ligand and support coupler wherein the support coupler is capable of associating with more than one ligand. For ligands and support couplers other than biotin and BSA, an input ratio of ligand to support coupler can be determined as was done for BSA and biotin in Example 1 (see Table 1) by selecting an input ratio that provides a desirable stability, determining an average substitution ($\lambda$), and viewing the orientation effect in a suitable distribution, for example, a Poisson distribution.

In the case of biotinylation of BSA, there are a large number of possible sites in the amino acid sequence of BSA that can be biotinylated using the primary amine-reactive biotinylation reagent sulfo-NHS-LC-biotin. Lysine, an amino acid that contains a free primary amine, occurs 59 times in the amino acid sequence of BSA. However, only about 30 to 35 lysine primary amines in BSA are available to react with amine-reactive biotinylation reagents. For example, N-terminal amines may be buried, or blocked, within the tertiary structure of BSA. Only primary amines located on the surface of the molecule (e.g., top, bottom, sides, grooves, pockets, etc.) are available for biotinylation. It has been empirically determined (see Example 1) that biotinylating BSA at a molar input ratio of 4 moles of sulfo-NHS-LC-biotin per mole of BSA results in an average of about 1.63 biotin molecules per BSA molecule (see Table 1).

Figure 3:
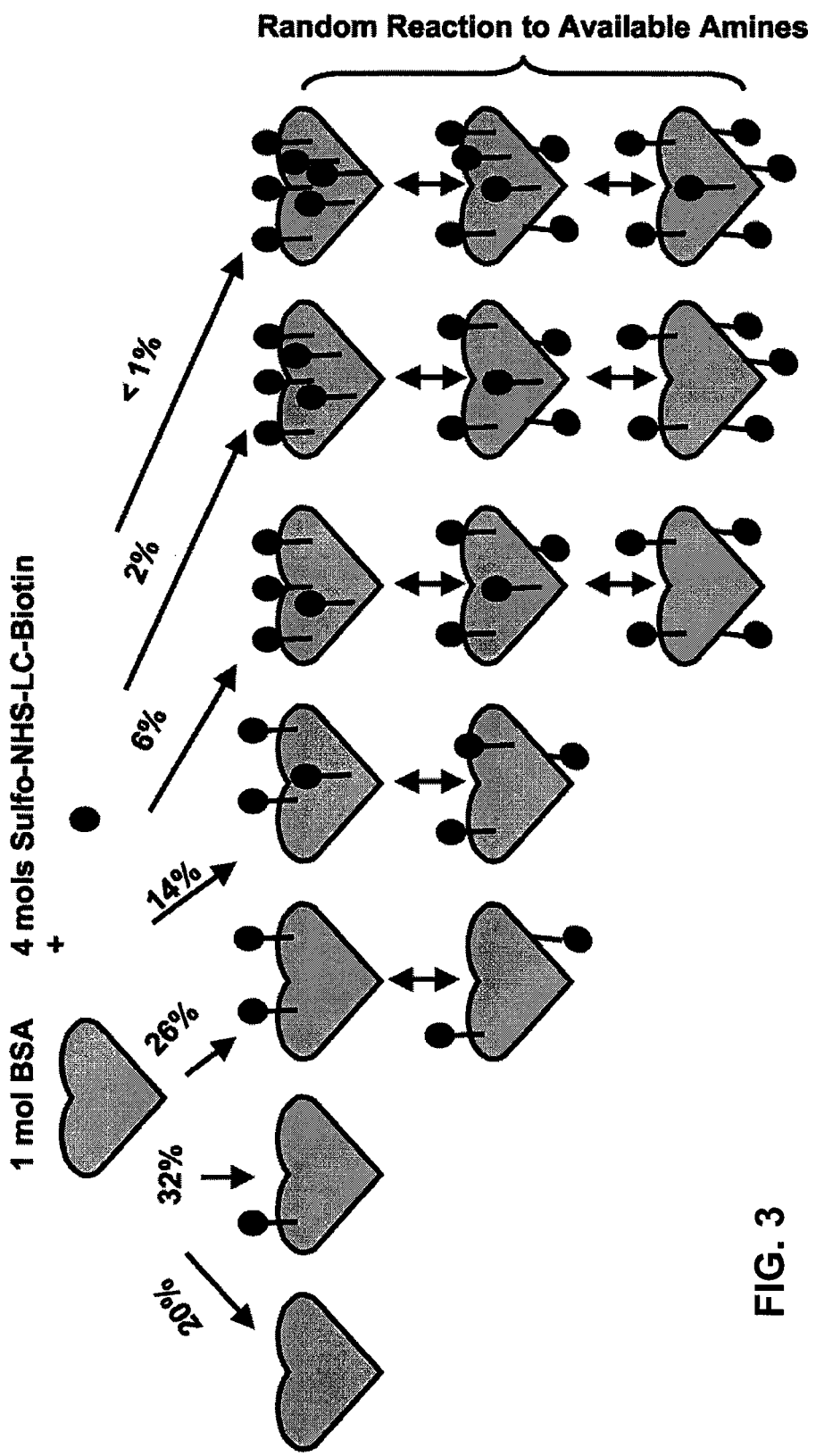
FIG. 3 illustrates some possible biotin molecule orientations on a BSA molecule in a low input ratio biotinylation method.

For BSA biotinylation, assuming a random reaction of sulfo-NHS-LC-biotin with the BSA molecules (4 moles sulfo-NHS-LC-biotin to 1 mole BSA), and an average substitution ($\lambda$) of 1.63 biotins per BSA molecule, the distribution of biotinylated BSA molecules can be approximated using a Poisson distribution (see FIG. 3: 20% of BSA have 0 biotins; 32% of BSA have 1 biotin; 26% of BSA have 2 biotins; 14% of BSA have 3 biotins; 6% of BSA have 4 biotins; 2% of BSA have 5 biotins; and <1% of BSA have 6 biotins. As illustrated in FIG. 3, the Poisson distribution reveals that at least 50% of the biotin-BSA complexes have less than or equal to three biotins per support coupler (i.e., BSA) at the selected molar input ratio of biotin:BSA. The distribution also reveals that at the selected molar input ratio, 0 to six biotins are conjugated per BSA molecule.

Low input ratio biotinylated BSA can be covalently coupled with a support, because BSA has about 30 to 35 primary amines available for primary amine chemistry and a Poisson distribution predicts that from 0 to six primary amines of BSA are conjugated to biotin following low input ratio biotinylation. Therefore, about 24 to 35 primary amines are still available to covalently couple each BSA molecule to a support via primary amine chemistry (e.g., tosyl, epoxy, carbodiimide, etc.). Multiple available primary amines may improve BSA coupling efficiency to a functional group of a support, and may improve stability via multiple attachment points (i.e., more than one support-to-BSA covalent bond per BSA molecule).

According to the biotinylation reagent manufacturer's instructions (Pierce Chemical Co., *Avidin-Biotin Chemistry: A Handbook*, M. Savage et al., 2nd Ed., 1992, page 34), a protein biotinylated with 2.5 moles of biotin per mole of protein can also result in a Gaussian (bell-shaped) distribution among the protein pool. While some proteins in the pool may have no biotin incorporated, most would have 2-3 moles of biotin incorporated, and a very small fraction of the pool may have 5 moles of biotin incorporated. Since biotin can be conjugated with any of the available primary amines, it is very possible to produce different biotin-BSA conjugates with biotin conjugated to different available amines on each BSA molecule.

Figure 4:
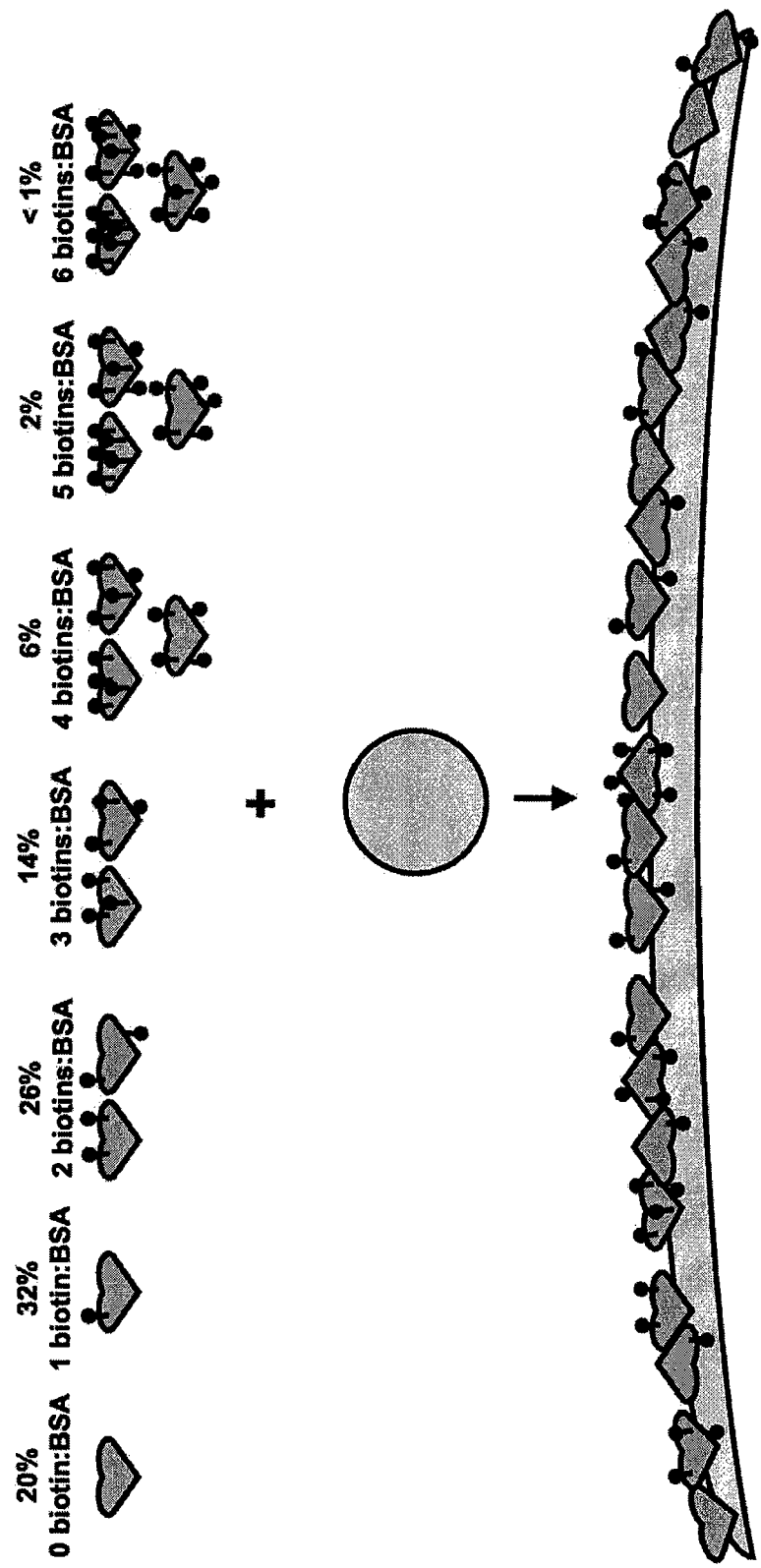
FIG. 4 illustrates coating a solid phase with low input ratio biotinylated BSA to make a non-saturated binding surface.

An illustration of how low input ratio biotinylated BSA can be used is shown in FIG. 4, which shows coupling of low input ratio biotin-BSA to a 1.0 micron tosylactivated microparticle solid phase with surface functional groups (i.e., carboxylic acid, tosylactivated, epoxy, etc.) used to covalently bind the biotin-BSA primary amino or sulfhydryl functional groups. The resulting support is non-saturated and orientated with respect to the biotin on its surface.

Since the biotin-BSA conjugate (ligand::support coupler complex) can have different numbers of biotin per BSA molecule, and the orientation of the BSA molecule and location of surface biotins are random, the biotin-BSA conjugate will couple with the support surface such that those biotins that extend into solution are sterically available as a binding surface, and those biotins that face the support surface are sterically unavailable as a binding surface.

Most commercially available microparticles are polystyrene-based, and protein absorption to the microparticle surface occurs passively (e.g., by hydrophobic and/or ionic interaction) and nonspecifically. Although a tosyl-activated microparticle is shown, the support can be activated with any suitable functional group (e.g., carboxylic acid, epoxy, etc.) that can covalently bind the biotin-BSA functional groups (e.g., the primary amino or sulfhydryl groups of BSA). If each epsilon amine on the surfaces of the BSA molecules has an identical pK, the distribution of biotin on the BSA surface should be Gaussian (Pierce Chemical Co., *Avidin-Biotin Chemistry: A Handbook*, M. Savage et al., 2nd Ed., 1992, page 34). FIG. 4 illustrates a non-saturated surface made by covalently associating biotin-BSA having an average substitution ($\lambda$) of 1.63 biotins per BSA molecule to a 1.0 micron support. As can be seen from the illustration, non-saturation here is achieved at least in part by coating the support with low input ratio biotinylated BSA.

Another method for achieving a non-saturated binding surface on a support comprises preparing ligand::support coupler complexes at a selected molar input ratio of ligand to support coupler, preparing a diluted preparation of the resultant ligand::support coupler complexes, and coating the support using the diluted preparation of ligand::support coupler complexes in the process of associating the ligand::support coupler complexes with the support. For biotinylated surfaces, which bind an at least bivalent biotin-binding moiety, the selected molar input ratio is preferably a low molar input ratio of biotin to support coupler to reduce performance degradation due to sloughing. In this method, the low input ratio is not responsible for the non-saturated character of the resulting support, because the non-saturated nature of ligands coupled with the support is achieved through limiting the concentration of ligand::support coupler complexes per unit area on the support rather than by limiting the amount of ligands per support coupler. Thus, for example, using this method BSA can be conjugated with biotin at molar input ratios in excess of 4 moles of biotin per mole of BSA, although biotinylation is preferably carried out at a low input ratio of biotin in order to reduce the amount of noncovalently bound biotin at the binding surface.

Although in many circumstances it would be undesirable and/or wasteful to biotinylate BSA (or couple any ligand with any support coupler) at high molar input ratios of ligand to support coupler (e.g., at a molar input ratio of about 20 or more moles of biotinylation reagent per mole of BSA), with this method, ligand::support coupler complexes (e.g., biotin-BSA) prepared at such high input ratios can also be used to make a non-saturated binding surface. Thus, without regard to limiting the average substitution ($\lambda$) of ligands per support coupler (e.g., biotins per BSA), limiting the saturation of ligands on a support can be achieved by limiting the concentration of ligand::support coupler complexes in the reaction that couples the ligand::support coupler complexes to the support. The extent of saturation can be further controlled by, for example, controlling the rate of the reaction by, for example, controlling the temperature of the reaction (e.g., cooling for endothermic couplings, or heating for exothermic couplings), selecting a slower or less reactive coupling chemistry, limiting reaction time, etc.

As noted above, most commercially available microparticles are polystyrene-based. Passive protein absorption to such surfaces through, for example, hydrophobic and/or ionic interaction, is known. Using blocking agents such as, for example, an at least one Pluronic®, is discussed herein to ameliorate nonspecific binding. Such agents, as disclosed in detail elsewhere herein, are also useful in creating monodisperse or substantially monodisperse preparations of microparticles comprising binding surfaces.

Figure 5:
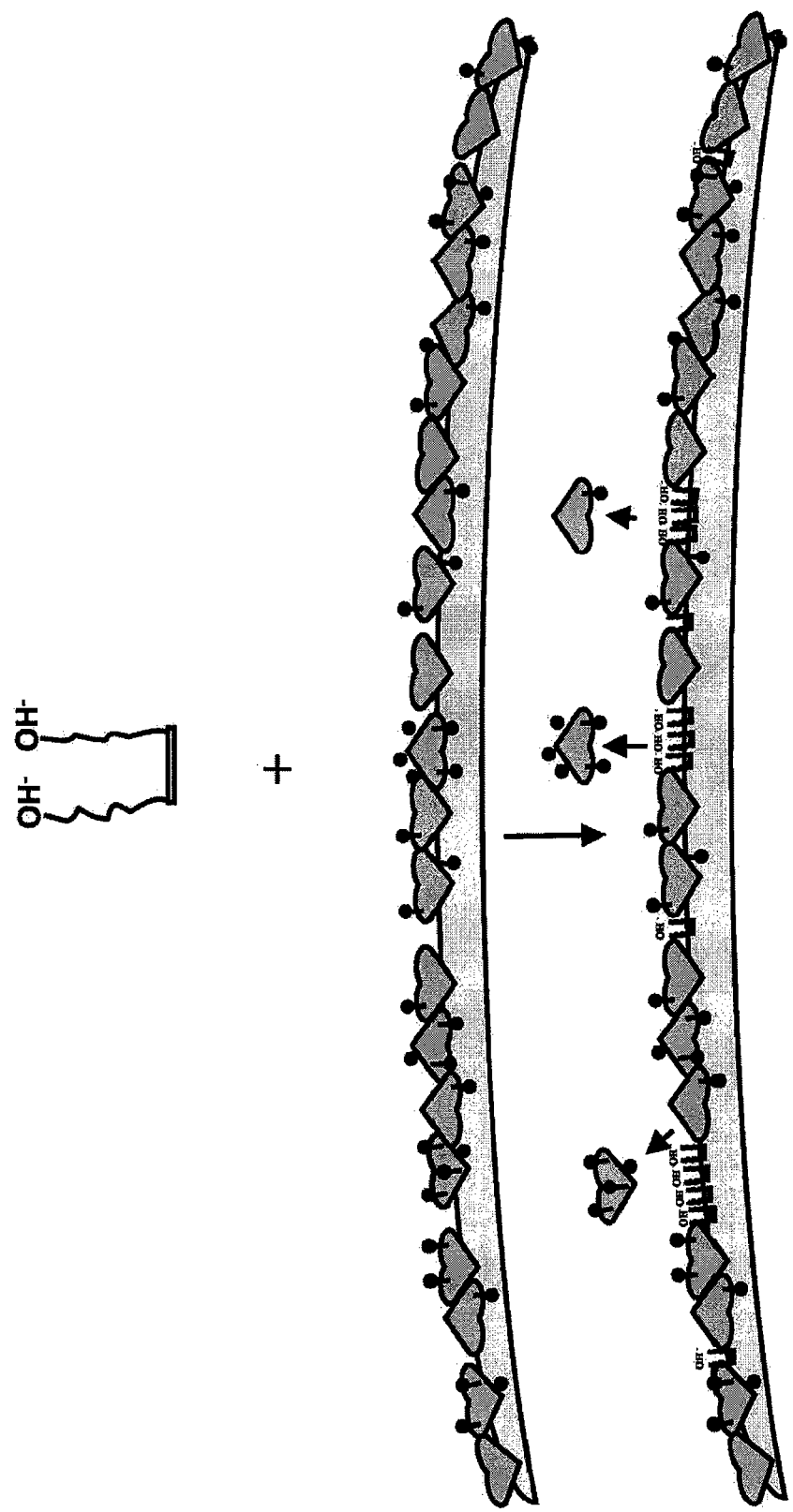
FIG. 5 illustrates using block copolymers as blocking agents for solid phase support surfaces.

The use of block copolymers as blocking agents for solid phases, and for the particular case of using a Pluronic® block copolymer as a blocking agent for microparticles coated with low input ratio biotinylated BSA, is illustrated in FIG. 5. The illustration is for Pluronic® F108 (M.W.≈13,518 Da; hydrophilic lipophilic balance (HLB)=27), which blocks the exposed hydrophobic polymer surface of the solid phase and displaces, removes, or strips passively absorbed protein without removing covalently attached protein. The surface then remains hydrophilic due to the presence of surface hydroxyls in the Pluronic® tails.

Any suitable block copolymer can be used that has the ability to associate with the support surface and also extend a relatively hydrophilic tail into the surrounding medium. Tri-block copolymers (such as, for example, Pluronic® F108 from BASF) have a single hydrophobic polypropylene (PPO) head group from about 17 to about 69 monomer units in length, and two hydrophilic polyethylene (PEO) tails from 1 to about 129 monomer units in length each. The hydrophilic lipophilic balance (HLB) of tri-block copolymers is directly related to the length or size of the PPO head group and PEO tails, and the HLB value can be from 1 (non-soluble in water) to 29 (highly soluble in water). If the PPO head group is at least 56 monomer units in length, the tri-block copolymer's head group can not only act as a hydrophobic probe and bind strongly to a hydrophobic surface, but it can compete with and displace another molecule from the same hydrophobic surface. If both PEO tails are at least 105 monomer units in length, they will extend into solution away from the solid phase surface. The hydroxyl groups at the end of each PEO tail provide a hydrophilic microenvironment since the tails are long enough and free to move from side-to-side in solution, and the hydroxyl tails act as a steric barrier to prevent passive protein absorption or re-absorption to the solid phase support surface.

Based on the theoretical available surface area, assuming a smooth surface of a 0.82 to 1.03 micron spherical micropar-ticle with a density of 1.5 g/cm$^3$ (38.83 to 48.77 cm$^2$ per mg microparticle), and the theoretical interfacial surface area of a Pluronic® F127 molecule (15.1 to 20.0 nm$^2$), the theoretical monolayer of Pluronic® F127 on the microparticle surface is calculated to be from about $4.05 \times 10^{-4}$ to about $5.43 \times 10^{-4}$ nmol Pluronic® F127 per mg microparticle. Fluorometric analysis of 5-(4,6-dichlorotriazinyl) aminofluorescein (5-DTAF) labeled Pluronic® F127 indicated that about $3.68 \times 10^{-4}$ to about $8.37 \times 10^{-4}$ nmol Pluronic® F127 binds per microgram of a 0.82 to 1.03 micron spherical microparticle.

Hemacytometer analysis was used to determine the minimum concentration of Pluronic® F108, Pluronic® F127, and Tetronic® 908 required to completely disrupt all polystyrene-based PMP aggregates and result in microparticle monodispersion. Concentration optimization studies indicated that Pluronic® F108 created a microparticle monodispersion of only monomers and dimers at concentrations from about 5 mM (0.007% w/v) to about 500 mM (0.67% w/v). Pluronic® F127 resulted in microparticle monomers, dimers and trimers from about 6.67 mM (0.009% w/v) to about 33.33 mM (0.043% w/v), and monomers, dimers and large aggregates from about 50 mM (0.064% w/v) to about 667 mM (0.850% w/v). However, Tetronic® 908 yielded aggregates at most concentrations tested. Pluronic® F108 worked as a biotin-BSA PMP blocking agent at concentrations from about 0.4% w/v to about 0.6% w/v. In other embodiments of the present invention, Pluronic® F108 is added at a concentration of about 0.1% w/v to about 1.0% w/v, or about 0.5% w/v to about 0.75% w/v.

Figure 6:
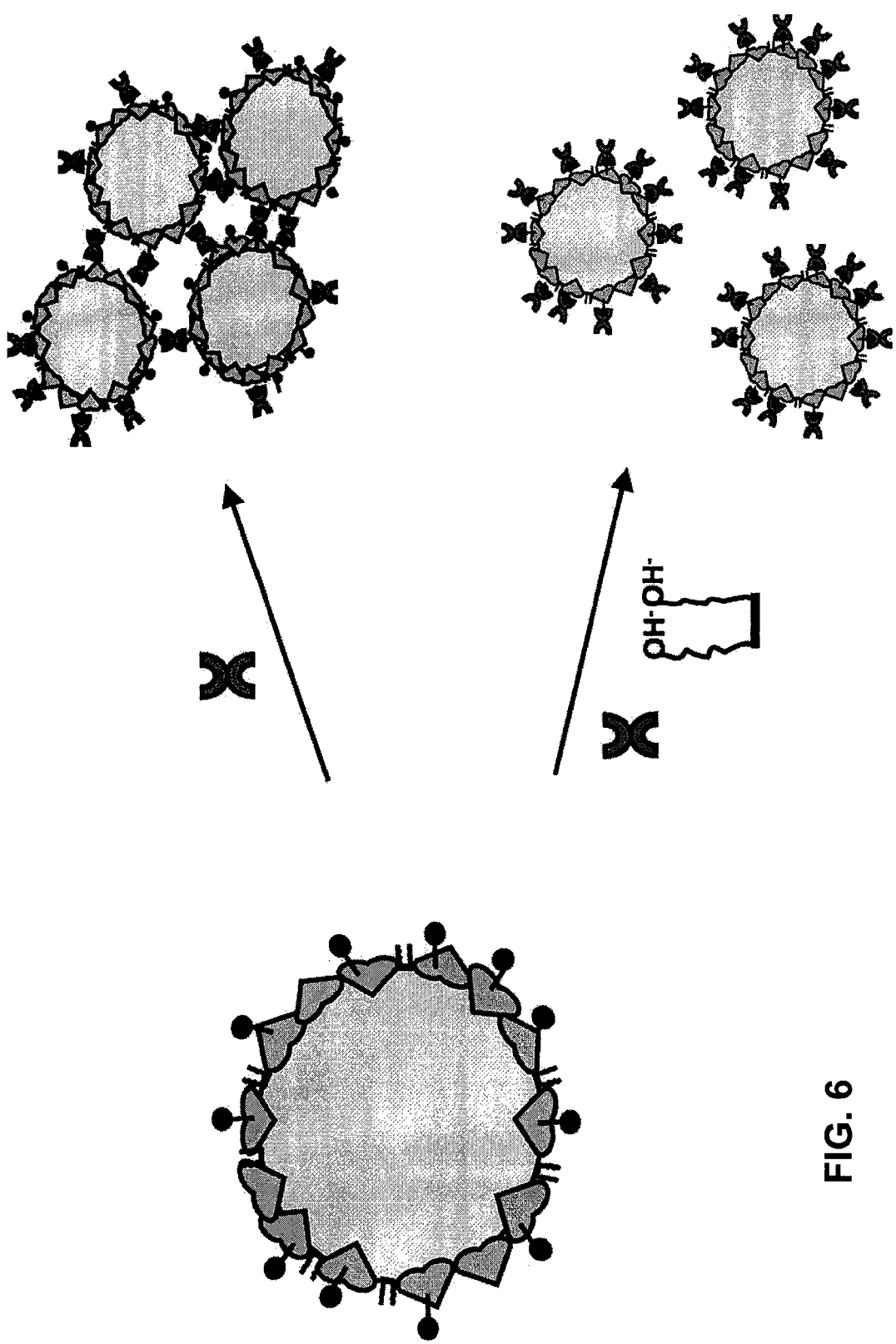
FIG. 6 illustrates using block copolymers as dispersion agents for binding surfaces comprising biotin.

The use of block copolymers as dispersion agents for microparticles coated with biotinylated molecules before adding biotin-binding molecules having two or more biotin-binding domains is illustrated in FIG. 6 for a specific embodiment using Pluronic® F108 as dispersion agent prior to adding SA to a biotin coated microparticle. In the illustration shown, the Pluronic® F108 is used to both promote monodispersion and to block nonspecific binding to the surface. Addition of an at least bivalent biotin-binding molecule is shown in the presence or absence of Pluronic® F108. In the absence of Pluronic® F108, the microparticles can aggregate during the addition of the biotin-binding molecule. In the presence of Pluronic® F108, the microparticles are monodisperse during and after the addition of the biotin-binding molecule.

A dispersion step is preferred under certain circumstances for optimal results because, for example, biotinylated microparticles displaying biotin-BSA that are combined with biotin-binding moieties having two or more biotin-binding domains (e.g., avidin, SA, or neutravidin) display a propensity to aggregate or clump due to crosslinking of the biotinylated microparticles via the two or more biotin-binding domains of each biotin-binding moiety.

Biotinylated microparticles, for example, coated with synthetic or biological ligand binders (biotin-binding moieties) comprising two or more biotin-binding domains per biotin-binding moiety have a propensity to aggregate or clump due to binding of an unoccupied, accessible binding domain of a biotin-binding moiety on one biotinlylated microparticle with an unbound, accessible biotin (ligand) on another biotinylated microparticle. Microparticle aggregation can be mitigated by slowly titrating (i.e. drop-by-drop addition) the biotinylated microparticles into a continuously mixed solution containing a very high concentration or molar excess of biotin-binding moieties (e.g., avidin, SA, neutravidin, a fragment of SA, a fragment of avidin or a fragment of neutravidin). This approach can mitigate microparticle aggregation by saturating the microparticle surface biotins with the biotin-binding molecules before crosslinking can occur. However, the titration approach is not very cost effective or robust, since there are multiple parameters to control, and it can be quite expensive due to the cost of certain biotin-binding moieties, but it can result in microparticle monodispersion after the coating with the chosen biotin-binding moiety.

Using a block copolymer such as a Pluronic® can be a better alternative to the aforementioned slow titration approach. Pluronic® F108 (a tri-block copolymer manufactured by BASF) has a single hydrophobic polypropylene (PPO) head group of about 56 monomer units in length, and two hydrophilic polyethylene (PEO) tails of about 129 monomer units in length. The PPO head groups of Pluronic® F108 act as hydrophobic probes and bind strongly to hydrophobic patches or sites on proteins or solid phase support surfaces such as microparticle support surfaces. As a result, Pluronic® F108 can be used to disrupt microparticle aggregation due to surface protein interactions (i.e., hydrophobic or ionic protein interactions). The PEO tails provide hydrophilic microenvironments and can act as steric barriers to prevent protein re-association due to hydrophobic or ionic interaction. As a result, once microparticles are treated with Pluronic® F108 they are very hydrophilic and are monodisperse in solution.

One embodiment of the present invention provides for improved affinity assays involving microparticles. In this embodiment, a population of dispersed microparticles, such as a monodisperse population of microparticles, is prepared using a block copolymer such as Pluronic® F108 or F127. The dispersed microparticles are then incorporated into a conventional affinity assay. Because the microparticles are dispersed, the affinity assay will have increased sensitivity (signal-to-noise ratio), increased assay accuracy, increased assay precision (quantitative assays), and increased assay reproducibility (qualitative assays).

Figure 7:
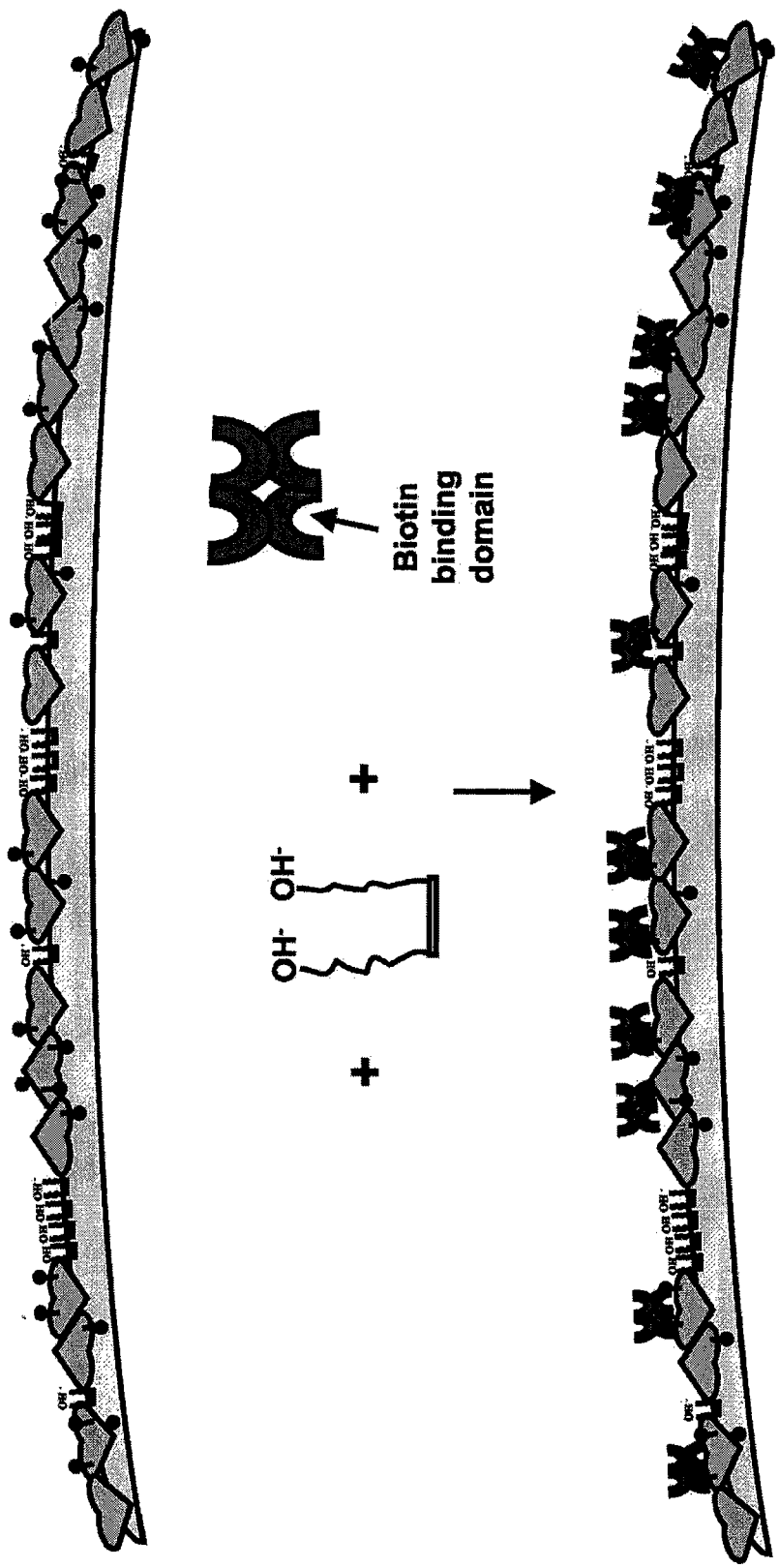
FIG. 7 illustrates coating a biotinylated binding surface, blocked with a block copolymer, with SA.

An illustration using a block copolymer in a dispersion step for the specific case of Pluronic® F108 and a SA-coated microparticle is shown in FIG. 6 and FIG. 7.

FIG. 7 shows microparticles coated with low input ratio biotinylated BSA and blocked with Pluronic® F108 that are dispersed or resuspended in 0.4% to 0.6% (w/v %) Pluronic® F108. Once the biotinylated microparticles are monodisperse, SA is added to coat the biotinylated microparticles. Since SA (M.W. about 56 kDa) is slightly smaller than BSA (M.W. about 66 kDa), it is likely that only one SA molecule can sterically bind with one biotin-BSA molecule (even if the BSA has multiple accessible biotins). In addition, not every BSA molecule has an available biotin (see the discussion of the Poisson distribution, above). Therefore, the total number of SA molecules captured on the binding surface will be less than the total number of BSA molecules coupled with the support surface, and SA will be non-saturated (there will be less than a maximal amount of SA molecules per unit surface area) on the binding surface (see Example 11).

After a support surface is coated with biotinylated synthetic or biological molecules (ligand::support coupler complexes) it can be used to capture or to capture and orientate a less than saturating amount of a synthetic or biological ligand binder (biotin-binding moiety) containing two or more biotin-binding domains. Assuming the biotin-binding domains are located on opposite, or approximately opposite, ends or sides of each biotin-binding moiety, at least one of its biotin-binding domains will bind with a solid phase biotin, whereas its remaining biotin-binding domain that is opposite, or approximately opposite, will be available to bind with a biotinylated capture moiety (e.g., biotinylated antibody or antigen).

As discussed above, biotinylated microparticles can be coated with a synthetic or biological ligand binder (biotin-binding moiety) containing two or more biotin-binding domains without microparticle aggregation by dispersing the biotinylated microparticles in about 0.4% to about 0.6% Pluronic® F108 (tri-block copolymer) prior to the addition of the biotin-binding moiety or by slowly titrating (e.g., drop-by-drop) the biotinylated microparticles into a continuously mixed solution containing a very high concentration or molar excess of biotin-binding moieties.

In practice, Pluronic® F108 dispersed microparticles coated with low input ratio biotinylated BSA at concentrations from about 0.1% to about 1.0% (w/v %), or alternatively from about 0.4% to about 0.6% (w/v %). Once biotinylated, microparticles were treated and dispersed in about 0.4% to about 0.6% (w/v %) Pluronic® F108 solution, low levels or amounts of SA could be added to the biotinylated microparticles without the formation of microparticle aggregates or clumps. This process resulted in microparticle monodispersion after the coating of the specific biotin-binding moiety (e.g. SA). The process is much more cost effective than the microparticle titration method described above, and is a very robust and reproducible method to coat biotinylated microparticles with synthetic or biological ligand binders (biotin-binding moieties) containing two or more biotin-binding domains.

Thus, in at least one embodiment, block copolymer can be employed at concentrations from about 0.1% w/v to about 1.0% w/v, or from about 0.4% to about 0.6% (w/v %) to both reduce nonspecific binding and to help promote a monodispersion of microparticles.

One goal of creating a non-saturated and orientated binding surface is to provide a foundation, or base, for building up components for an affinity assay. Since the underlying ligand::support coupler complex constructed in accordance with the invention is non-saturated and orientated, any components built upon this ligand::support coupler complex will reflect its non-saturated nature and orientation. An example of such a structure is shown in FIG. 8.

Figure 8:
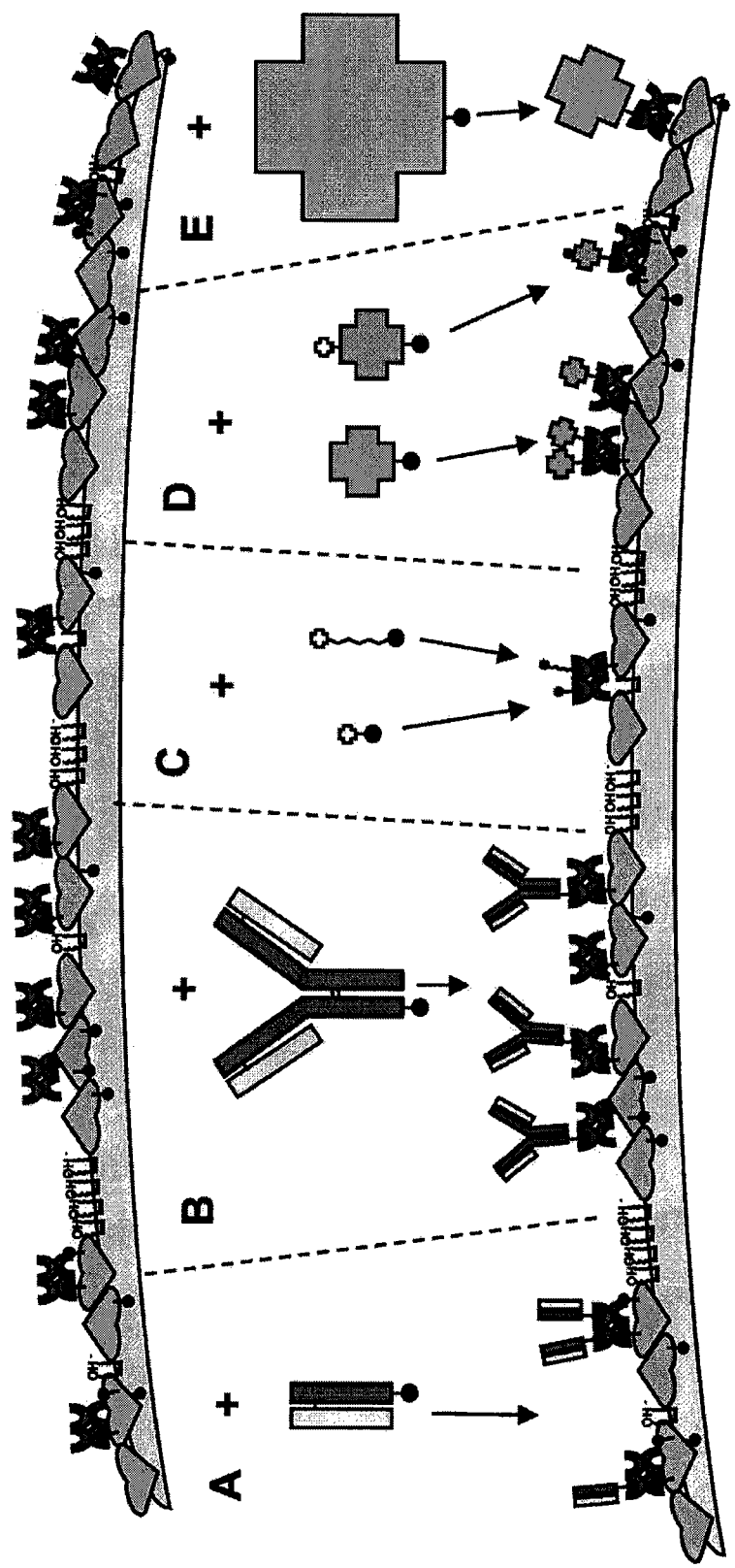
FIG. 8 illustrates applying various biotinylated capture moieties to a SA-coated binding surface on a solid phase support surface made in accordance with the invention.

FIG. 8 shows the coating of biotinylated capture moieties onto a biotin-specific microparticle binding surface that was prepared by (1) coating the surface with low input ratio biotinylated BSA; (2) blocking the surface with the tri-block copolymer Pluronic® F108, (3); dispersing the microparticles in Pluronic® F108 prior to the addition of the synthetic or biological biotin-binding moiety (e.g., SA) containing two or more biotin-binding domains; and (4) adding SA to the surface. The resulting SA-coated microparticle can be used to orientate and capture a non-saturating amount of any biotinylated capture moiety of interest.

FIG. 8 illustrates how the SA-coated microparticle is used to orientate and capture a non-saturating amount of certain biotinylated capture moieties of interest, including (A) Fab fragments of antibodies (the absence of the Ig Fc region can decrease or mitigate nonspecific binding issues); (B) immunoglobulins (polyclonal and/or monoclonal antibodies); and (C. D, and E) small, medium, and/or large molecules, respectively, whether they be synthetic or biological. Any of the biotinylated capture moieties of interest can comprise a spacer, for example, between the molecule and the biotin moiety.

Spacers may be particularly useful in the case of biotinylated molecules that are relatively small. Since biotin-binding domains in the SA molecule are buried 9 Angstroms below the surface, biotinylated small molecules (e.g., those having a molecular weight of less than about 1,000 Da) may not be detectable by larger immunoassay tracers (detectable binders) due to steric hindrance. A greater binding capacity and higher detection sensitivity can be realized by using biotin derivatives that have spacer arms attached to them, or by conjugating the small molecule to a larger biotinylated molecule (i.e., a carrier molecule).

To the extent that they are useful, guidelines for distinguishing small molecules from medium or large molecules can be expressed in the following manner: small molecules are generally considered to be of molecular weight less than about 5,000 Da; medium molecules are generally considered to be of molecular weight from about 5,000 or more to about 150,000 Da; large molecules are generally considered to be those above about 150,000 Da in molecular weight.

Figure 9A:
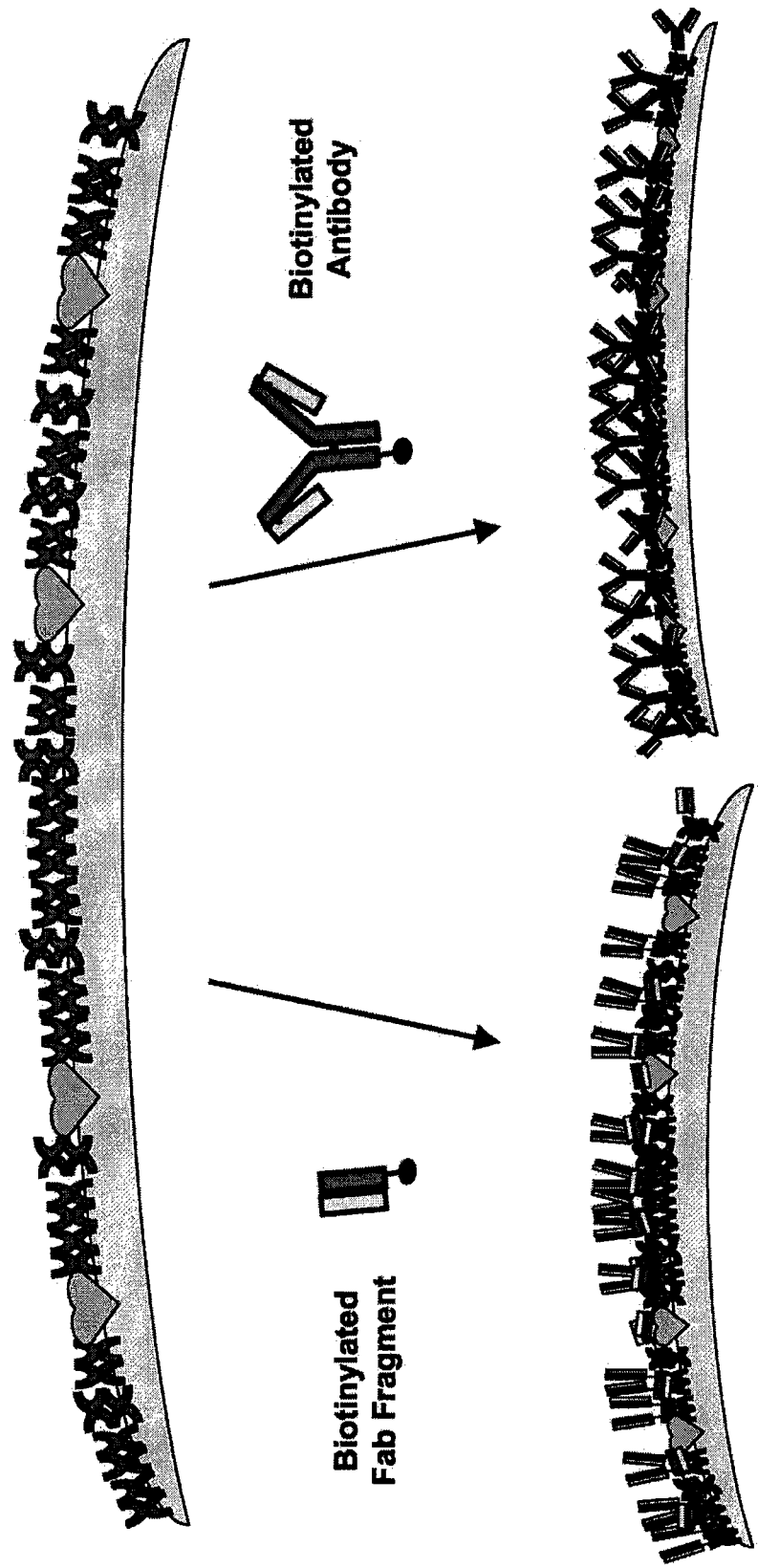
FIG. 9A illustrates a conventional or standard SA-coated microparticle binding surface coated with a biotinylated antibody or Fab fragment.
Figure 9B:
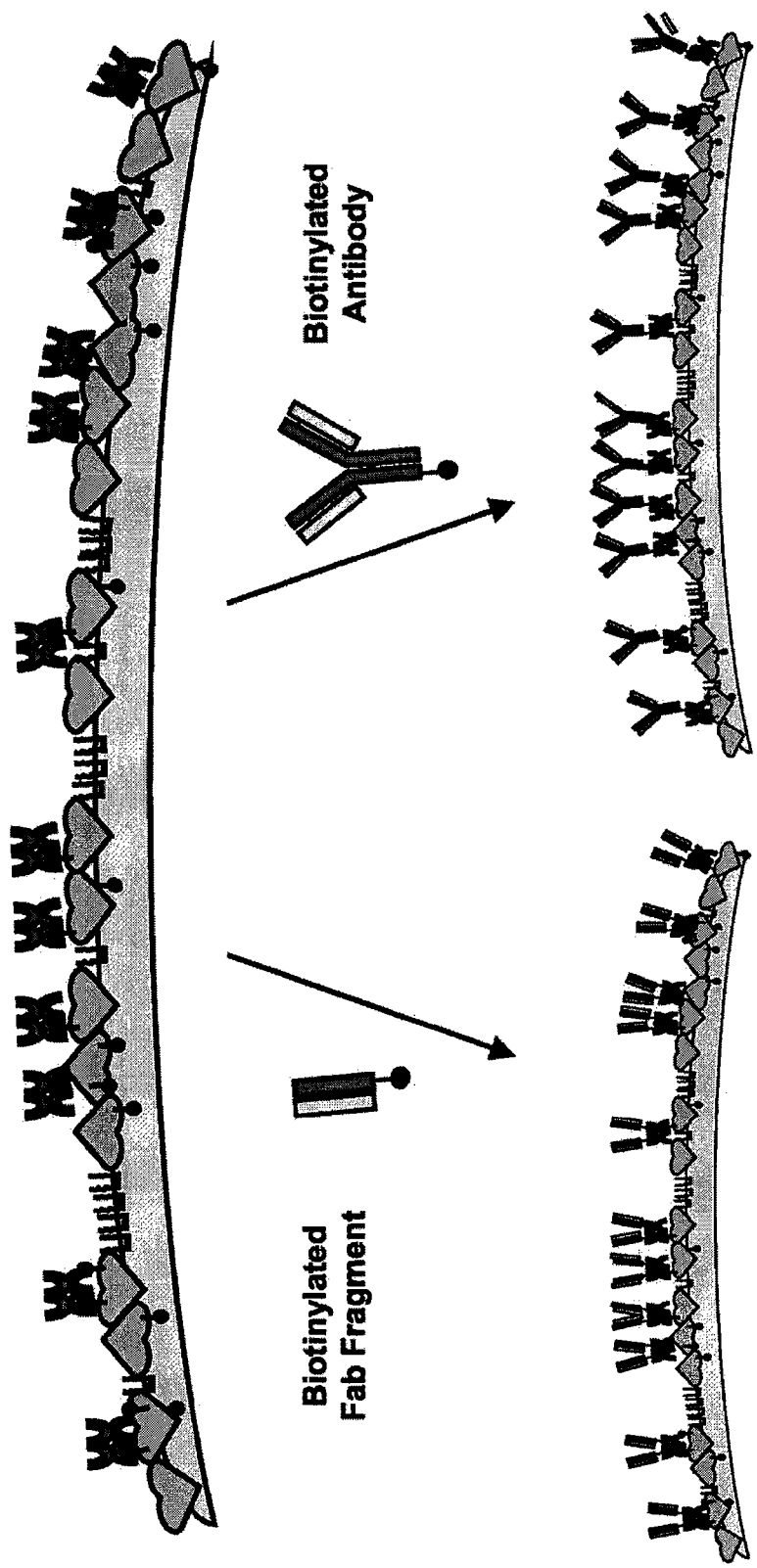
FIG. 9B illustrates a non-saturated and orientated SA-coated microparticle coated with a biotinylated antibody or Fab fragment.

Certain aspects of the invention in making microparticles with binding surfaces in accordance with the invention are illustrated in FIGS. 9A and 9B.

FIGS. 9A and 9B illustrate the orientation and coating of a less than saturating amount of biotinylated antibodies, or biotinylated Fab fragments, onto biotin-binding microparticles (e.g., SA-coated microparticles) prepared in accordance with the invention.

SA-coated PMPs prepared in accordance with the invention can improve immunoassay sensitivity (increase signal-to-noise ratio), since the biotin-binding solid phase can be used to orientate and capture less than a saturating amount of a biotinylated capture moiety such as, for example, analyte-specific biotinylated antibodies or Fab fragments. Assay sensitivity is improved because a decrease in the total number of SA molecules per support surface area of each SA-coated microparticle results in a decreased biotinylated capture antibody binding capacity, but improved biotinylated capture antibody binding performance due to improved steric freedom. That is, the purpose of providing a lower than maximal amount of SA molecules on a surface is to improve the steric freedom of each SA molecule to bind large biotinylated capture moieties (e.g., biotinylated antibodies), and to improve the binding efficiency of each SA molecule.

FIG. 9A illustrates a conventional or standard SA-coated microparticle surface, where SA is directly coated onto the microparticle surface by primary amine or other coupling chemistry, and the surface is blocked using BSA. On such a conventional or standard surface, the SA molecule is not specifically non-saturated or orientated on the surface; that is, attachment is random. Adding a biotinylated antibody or Fab fragment results in a binding surface that is not predominantly non-saturated or orientated since the SA on the surface is randomly orientated. Antibody or Fab crowding can create steric barriers (low accessibility) and decrease antigen capture efficiency, particularly if the antigen is a large molecule.

FIG. 9B illustrates a SA-coated microparticle binding surface made in accordance with the invention. On this binding surface, SA molecules are non-saturated (a decrease in total SA molecules per unit binding surface area of a microparticle) and orientated on the surface. The microparticle support surface is covalently coated with low input ratio biotinylated BSA, and blocked with Pluronic® F108. The biotinylated microparticles are then dispersed in Pluronic® F108 prior to SA addition. SA attachment is specific and not random.

The biotinylated antibody or biotinylated Fab fragment attachment to the SA microparticle binding surface made in accordance with the invention is non-saturated and orientated because the SA molecule is also non-saturated and orientated on the binding surface. The orientation and less-than-saturated nature of the biotinylated antibody or biotinylated Fab fragment promotes antigen (analyte) capture efficiency (signal is increased), particularly if the antigen is a large molecule. In addition, the surface of the microparticle is hydrophilic due to the Pluronic® F108 blocker, and nonspecific binding to the surface is minimized or eliminated (noise is decreased).

Another feature of the invention is illustrated in FIG. 10, which shows the increased available surface area associated with a microparticle monodispersion.

FIG. 10, panel A illustrates that microparticles aggregate or agglutinate due to microparticle-to-microparticle surface interactions. This aggregation will decrease both (1) the total available microparticle surface area, since any area inside the aggregate is not sterically available (accessible), and (2) the binding capacity and efficiency of the biotin-binding moiety (e.g., SA) on the binding surface, resulting in decreased assay signal.

FIG. 10, panel B illustrates that microparticles in accordance with the invention have increased binding surface area, which results in improved binding capacity and improved binding efficiency of the biotin-binding moiety (e.g., SA) on the binding surface, resulting in increased assay signal. Monodisperse microparticles have more total available surface area than aggregated microparticles or microparticle clumps, and they will provide improved assay kinetics due to increased collision rates and decreased assay diffusion distance.

Microparticles in accordance with the invention are designed such that the low input ratio biotinylated BSA binding surface is blocked with a block copolymer such as the tri-block copolymer Pluronic® F108, and the biotinylated microparticles are dispersed in Pluronic® F108 prior to the addition of the SA molecules as discussed above. Of course, Pluronic® F108 is only exemplary of this embodiment. It is understood that any block copolymer of this invention can be used in this fashion.

Microparticles in accordance with the invention were made using biotin as a ligand, and either BSA or ovalbumin as a support coupler. SA-coated microparticles were also made, as well as microparticles with specific capture moieties. The results of these studies are discussed below and in the Examples.

Figure 11:
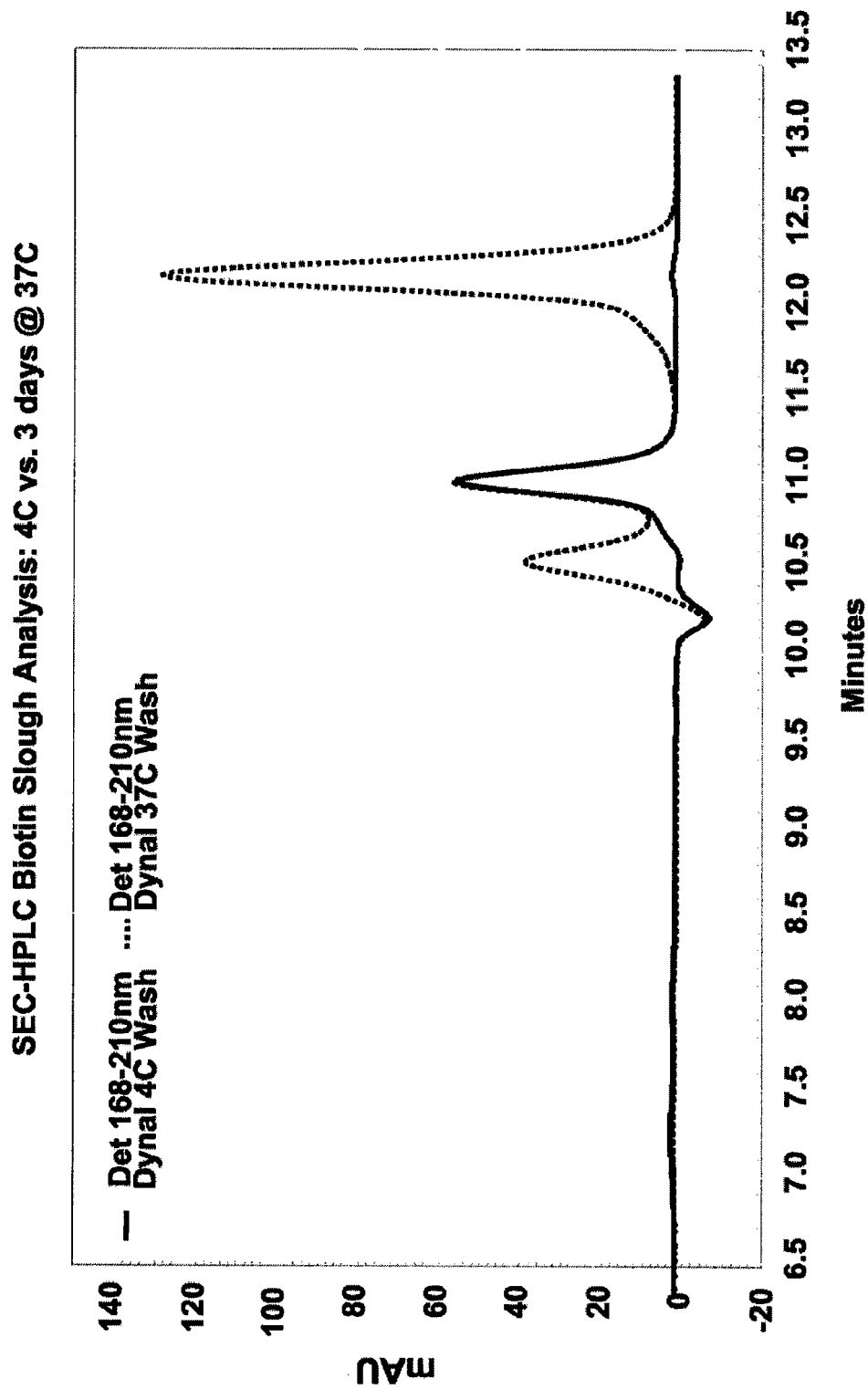
FIG. 11 illustrates biotin sloughing analysis from a biotin-BSA solid support coated with SA after 3 days at 4° C. or 37° C.

The effect of varying molar input ratios of biotin in biotinylation reactions was studied, and is presented in Example 1. Biotinylation of BSA at various molar input ratios of biotin to BSA ranging from 3.4:1 to 30:1 was conducted, extent of biotinylation determined, and stability at 4° C. and 37° C. for three days was determined (see Table 1). Decreases in stability reflect at least in part the sloughing or dissociation of biotin or biotin reagent from biotin-BSA conjugates (see FIG. 11). The results indicated that biotin-BSA prepared at high molar input ratios of biotin (e.g., 8:1, 15:1, and 30:1) display poor stability, but as the molar input ratio of biotin reagent to BSA decreases from 30:1 to 4:1, stability improves from 4% to 100%. Thus, selecting a relatively low input ratio of ligand to support coupler, and associating the ligand::support coupler complex to a solid phase, results in a more stable binding surface than conventionally prepared binding surfaces having biotin as a ligand.

Making a non-saturated binding surface by coating a support surface with a ligand::support coupler complex prepared at any input ratio (and particularly with ligand::support coupler complexes prepared at a high input ratio of ligand to support coupler) can be facilitated by adding a suitable dispersant to the ligand::support coupler complex after its preparation, but before it is coated onto the support surface. Suitable dispersants for this method are discussed herein. An illustration is provided herein for using a suitable dispersion agent with biotin-BSA prepared at a low input ratio of biotin to BSA to prepare a non-saturated surface, although the method employing a dispersion agent is not limited to biotinylated coatings.

A method for making a non-saturated binding surface using a suitable dispersion agent to prevent aggregation of solid phase supports such as, for example, microparticles, is provided. The method is based at least in part on the observation that a relatively disperse (for example, an approximately monodisperse) preparation of microparticles is desirable.

The method can be employed where aggregation of microparticles can occur, for example, where the ligand is biotin and the biotin is coated with SA. The dispersion method is particularly useful where the ligand binder is at least bivalent, that is, where a single, at least bivalent, biotin-binding moiety such as SA can cross-link a biotin of a biotin-BSA molecule on one microparticle with a biotin of a biotin-BSA molecule on another microparticle. An illustration of the dispersion method is provided herein for an embodiment where the ligand::support coupler complex is biotin-BSA, and the ligand binder (biotin-binding moiety) is SA, below and in Example 2. However, as previously explained, the method is not limited to biotin/SA binding surfaces.

Dispersion agents such as, for example, block copolymers can be used in a method for making a non-saturated binding surface. In the illustration provided herein, block copolymers are used as dispersion agents for microparticles coated with synthetic or biological ligand::support coupler complexes prior to the addition of synthetic or biological biotin-binding moieties (ligand binders) comprising two or more biotin-binding domains. In the illustration provided herein, the block copolymer Pluronic® F108 is employed; however, the method is not limited to the particular block copolymer of the illustration.

Generally, FIG. 7 illustrates coating a biotinylated surface, synthetic or biological, with synthetic or biological biotin-binding moieties (ligand binders) containing two or more biotin-binding domains. More specifically, FIG. 7 illustrates coating SA onto a low input ratio biotinylated BSA microparticle binding surface blocked with Pluronic® F108 and dispersed in Pluronic® F108 prior to SA addition.

The methods and compositions provided herein can be used in preparing a non-saturated coating for a solid phase support surface, wherein the coating comprises a ligand::support coupler complex coupled with a support surface, a ligand binder (biotin-binding moiety) associated with the ligand of the ligand::support coupler complex, and a capture moiety (e.g., a biotinylated capture moiety) associated with the ligand binder. The capture moiety can be selected so as to facilitate capture of any molecule of interest, such as an analyte. An illustration is provided below and in FIG. 8 for a biotin/SA system, but the invention is not limited to a biotin/SA system.

Non-saturated binding surfaces can be designed by orientating and associating less than a saturating amount of synthetic or biological ligand binders (biotin-binding moieties) containing two or more biotin-binding domains on a support surface. The surfaces can be illustrated by an example that orientates and provides a less than saturating amount of SA on the surface of microparticles, for example, PMPs. FIG. 8 illustrates a non-saturated and orientated binding surface made by coating biotinylated capture moieties onto a biotin-binding microparticle binding surface that was prepared by (1) coating the surface with low input ratio biotinylated BSA; (2) blocking the surface with the tri-block copolymer Pluronic® F108; (3) dispersing the microparticles in Pluronic® F108 (prior to adding synthetic or biological biotin-binding moieties containing two or more biotin-binding domains); and (4) adding SA as biotin-binding moiety. As shown in FIG. 8, the SA-coated microparticles can be used to orientate and/or capture a less-than-saturating amount of biotinylated capture moieties, for example: (A) Fab fragments of antibodies (the absence of the Ig Fc region can decrease or mitigate nonspecific binding issues); (B) immunoglobulins (polyclonal and/or monoclonal antibodies); and (C. D, and E) small, medium, and/or large molecules, respectively, whether they be synthetic or biological.

FIG. 8 illustrates biotinylated capture moieties on a non-saturated binding surface employing a biotin/SA system. Low input ratio biotinylated BSA covalently attached to the surface of a microparticle is blocked with the tri-block copolymer Pluronic® F108, the microparticles are dispersed in Pluronic® F108 prior to adding SA, SA is added, and then a desired biotinylated capture moiety is exposed to the non-saturated SA-coated surface. The examples of biotinylated capture moieties shown include (from left to right in FIG. 8: biotinylated Fab fragment (M.W. of about 30,000 Da), biotinylated antibody (IgG, M.W. of about 150,000 Da); biotinylated small molecule, or biotinylated small molecule with a spacer arm (e.g., M.W. less than about 5,000 Da); biotinylated medium molecule, or biotinylated medium molecule as a carrier for a small molecule (e.g., M.W. about 5,000 Da to about 150,000 Da); and biotinylated large molecule (e.g., M.W. more than about 150,000 Da). As can be seen from FIG. 8, the orientated and non-saturated nature of the biotin-BSA at the surface of the solid phase support is reflected in a non-saturated SA-coated surface, and in a non-saturated capture moiety coating as well. Hydrophobic head groups of Pluronic® F108 are shown associated with the support surface, and hydrophilic tail groups of Pluronic® F108 are shown extending away from the support surface.

Non-saturated binding surfaces in accordance with the invention typically have lower binding capacity than commercially available binding surfaces. An example is provided employing a biotin/SA system (see Table 2, Example 2). A support coated with fewer SA molecules per unit surface area will inherently have a decreased capacity to bind biotin, since the surface will have fewer biotin-binding sites. The purpose of providing a lower than maximal amount of SA molecules on a surface is to improve the steric freedom of each SA molecule to bind large biotinylated capture moieties (e.g., biotinylated antibodies), and to improve the binding efficiency of each SA molecule.

Example 2 illustrates that having an orientated and less than saturating amount of a molecule on a binding surface decreased binding capacity, but increases assay signal, resulting in a better and more efficient binding surface for an affinity assay. Microparticles in accordance with the invention display decreased binding capacity in comparison to analogous, commercially available, conventional or standard products (see, for example, Table 2), but enhanced assay performance (see, for example, Table 3 and Table 4). Increased signal-to-noise ratios due to lower background and increased signal response reflect enhanced assay performance. Overall, the results support that the invention allows for production of SA-coated microparticles with lower binding capacity than commercially available SA-coated microparticles, but enhanced assay performance due to stretavidin orientation and steric acessibility on the microparticle surface, and novel binding surface blocking.

Example 3 illustrates that microparticles made in accordance with the dispersion step of the invention result in a monodisperse population of microparticles substantially free of aggregates or clumps.

Example 4 illustrates that microparticles according to the invention, in a specific embodiment of a SA-coated microparticle, in contrast to conventional or standard microparticles, display more favorable signal-to-noise ratio characteristics due to the non-saturated nature and orientation of the SA, enhanced surface blocking, and improved binding efficiency.

Example 5 illustrates reduction in nonspecific binding employing microparticles in accordance with the invention. Nonspecific binding in microparticles according to the invention is reduced even in assays where analytes have a preference for associating with a coating on the solid phase, such as the preference of thyroid hormones such as T3 (triiodothyronine) and T4 (thyroxine) for BSA.

Example 6 establishes through validation studies that the inventive process for coating a support is reproducible and reliable, a desirable feature for diagnostic affinity assays.

Example 7 shows that microparticles according to the invention display enhanced stability in multiple validation lots, for the particular embodiment of SA-coated microparticles. Example 8 establishes that sloughing of ligand in the inventive microparticles is not a problem, and Example 9 shows binding surfaces according to the invention made with ovalbumin instead of BSA.

Although much of the discussion and many of the Examples describe making non-saturated surfaces by coating a support surface with a support coupler having a ligand complexed to it, wherein the support coupler comprises a protein, non-saturated or non-saturated and orientated binding surfaces can be achieved using the invention in a variety of ways. For example, the support coupler can be a non-protein such as, for example, a polymer. The polymer can be functionalized to react and complex with the ligand, or polymer/ligand pairs can be selected such that functional groups naturally present on the polymer will bind with a functionality of the ligand under a specific set of conditions. The number of reactive, or functional, groups on the polymer can be controlled by inactivating some of the reactive groups, thereby allowing less ligand to be attached per polymer molecule.

Polymer/ligand complexes can also be diluted with polymer lacking ligand, and the diluted mixture can be used to coat a support surface to make a non-saturated or non-saturated and orientated binding surface. One kind of polymer, or a mixture of polymers, can be used.

Accordingly, in various embodiments the invention comprises a support comprising a binding surface for an affinity assay, comprising ligands attached to polymers, wherein the ligands are non-saturated or non-saturated and orientated on the surface. The support comprising the ligand can then be treated in accordance with any suitable method described herein. In various embodiments, the surface comprises a mixture of polymers without any ligand attached, and polymers with ligand attached. In various embodiments, the support is a microparticle, the binding surface is blocked with a block copolymer, the assay is an immunoassay, and the ligand binds an at least bivalent ligand binder that itself can bind with a capture moiety, such as a modified or unmodified immunoglobulin or fragment thereof.

In certain embodiments, a ligand can be coupled directly on a support surface without the use of a support coupler. In these embodiments, a support surface having functional groups capable of reacting with a ligand is exposed to the ligand under conditions sufficient for the ligand to attach to the support. In various embodiments the attachment is a covalent bond between an activated ligand and the support surface, which can also be activated. Non-saturation of the ligand can be achieved by controlling the number of ligands that attach to the support surface. In various embodiments the support surface comprises a plurality of functional groups capable of reacting with the ligand under a given set of conditions. The support surface can be treated in a manner to reduce the number of functional groups that are capable of reacting with the ligand, either by manipulating reaction conditions or adding an agent that reduces the number of functional groups on the support surface. The support surface comprising the ligand can then be treated in accordance with any suitable method described herein.

Accordingly, the present invention also provides a support surface coated with a ligand, wherein the ligand is non-saturated on the surface of the support surface. In various embodiments, the binding surface is blocked with a block copolymer, the assay is an immunoassay, and the ligand binds an at least bivalent ligand binder that itself can bind with a capture moiety, such as a modified or unmodified immunoglobulin or fragment thereof. In various embodiments, the density of ligand on the support surface is within the ranges described herein for embodiments describing ligand attached to support couplers. Any suitable ligand can be used to attach directly to a support surface, such as, for example, immunoglobulins or fragments thereof, oligonucleotides, and lectins. As in other embodiments, the ligand can comprise a linker, and the linker can be attached to the support surface.

The present invention provides for orientating and associating a less than saturating amount of ligand such as SA on the surface of a microparticle (for example, a PMP). Commercially available biotin-binding surfaces (for example, Dynal® DYNABEADS™ MyOne Streptavidin T1, and DYNABEADS M-280 Streptavidin) are designed to have maximum biotin binding capacity. Commercially available biotin-binding surfaces are typically produced by direct coating of SA or other biotin-binding molecules on a microparticle surface. In contrast, the present invention provides for coating microparticles with low input ratio biotinylated BSA, blocking the biotin-BSA microparticles with Pluronic® F108, dispersing the blocked biotin-BSA microparticles in Pluronic® F108, and finally coating the biotin-BSA microparticles with SA.

Microparticles in accordance with the invention exhibit more favorable signal-to-noise ratio characteristics due to non-saturation and orientation, enhanced surface blocking, and improved binding efficiency. This is demonstrated for low input ratio biotinylated BSA microparticles coated with SA, as shown in the Examples.

The methods and compositions of the invention can be used in conjunction with any suitable assay known in the art, for example any suitable affinity assay or immunoassay known in the art where a non-saturated or non-saturated and orientated surface can be advantageously used, including, but not limited to, protein-protein affinity assays, protein-ligand affinity assays, nucleic acid affinity assays, indirect fluorescent antibody assays (IFAS), enzyme-linked immunosorbant assays (ELISAs), radioimmunoassays (RIAs), and enzyme immunoassays (EIAs), direct or indirect assays, competitive assays, sandwich assays, etc. Suitable assay formats include, but are not limited to, assays and formats employed in the Examples herein.

The methods and compositions of the invention can be used in connection with any support, for example a suitable solid support, known in the art. Examples of such solid phase supports are discussed, but the invention is not limited to the supports explicitly discussed. For example, solid phase supports are not limited to particulate supports, to microparticles, to polystyrene microparticles, to microtiter plates, to coated tubes, etc. Other solid phase supports can also be used with the invention, including but not limited to any supports known in the art that are used in connection with affinity assays. For example, solid phase supports that comprise mylar-backed nitrocellulose, and/or nylon can be used. Solid phase supports that comprise filters or membranes, for example, can be used. Solid phase supports that comprise microtubules, nanoparticles, or nanotubes, for example, carbon nanotubes, can be used. Solid phase supports can comprise microparticles of any size and solid phase supports that have a large planar surface area can be used.

The methods and compositions of the invention can be used in connection with any assay where an improved signal-to-noise ratio is desired. For example, a binding surface in accordance with the invention that is non-saturated and treated with a suitable block copolymer such as, for example, a Pluronic®, can be prepared on a planar or substantially planar solid phase support for use in a lateral flow assay and/or diffusion assay. One example of a lateral flow assay is where a sample is placed on a binding surface (immobilized or not) and one or more analytical reagents in a liquid phase are passed over the sample (in a diffusion assay, by diffusion over the surface), and the analyte is detected and/or quantitated by a suitable signal when contacted with a reagent in the liquid phase. Another example of a lateral flow assay is where one or more analytical reagents are placed on a binding surface (immobilized or not), and a sample in a liquid phase is passed over the one or more analytical reagents (in a diffusion assay, by diffusion over the surface), and an analyte in the sample is detected and/or quantitated by a suitable signal when contacted with one of more analytical reagents on the binding surface. Another example of a lateral flow assay is a dipstick comprising a non-saturated binding surface in accordance with the invention. Lateral flow and/or diffusion assays are not limited to liquid moving across one binding surface of a planar support; such assays include liquid moving through a membrane or filter, wherein the membrane or filter comprises a non-saturated binding surface. Accordingly, in various embodiments, a binding surface for a lateral flow assay and/or for a diffusion assay is provided, as well as methods and compositions for making a binding surface for a lateral flow assay and/or a diffusion assay, in accordance with any of the embodiments described herein.

In another aspect, use of any of the methods and compositions herein in an immunoassay is provided. In various embodiments, use of a support having a non-saturated binding surface comprising a plurality of support couplers disposed on the support and ligands coupled with the support couplers, wherein the ligands are non-saturated and are orientated on the surface in a manner that provides sterically accessible ligands, in an immunoassay is provided. In a specific embodiment, a microparticle having a binding surface comprising biotinylated protein (ligand::support coupler complex), an at least bivalent biotin-binding moiety selected from avidin, SA, neutravidin, a fragment of SA, a fragment of avidin, a fragment of neutravidin, or mixtures thereof associated with the biotin moiety of the biotinylated protein, and a biotinylated immunoglobulin or fragment thereof (biotinylated capture moiety) associated with the at least bivalent biotin-binding moiety (ligand binder) is used in an immunoassay for an analyte of interest, for example an antigen, in a sample. In another embodiment, the at least bivalent biotin-binding moiety that is associated with the biotin moiety of the biotinylated protein is associated with a biotinylated antigen or fragment thereof (biotinylated capture moiety) and the microparticle is used in an immunoassay for an analyte of interest, for example an antibody, in the sample. Characteristics of the compositions, and methods of making the compositions, used in the immunoassay include any of the characteristics (including, for example, specific embodiments that recite density of the components of the surface) described herein.

The methods, compositions, and kits of the invention can be applied for use with any suitable immunoassay system. Examples of suitable immunoassay systems include, but are not limited to, the Access® Immunoassay System, the Access® 2 Immunoassay System, the Synchron LXi® 725 Clinical System, the UniCel® Dxl 800 Access® Immunoassay System, the IMMAGE® Immunochemistry System (all from Beckman Coulter, Inc.), and the Triage® system (Biosite, Inc.). One suitable immunoassay array system is the A$^2$® Microassay system (Beckman Coulter, Inc.).

Itemized below is a nonlimiting list of substances that may function as one, or alternatively as the other, member of a binding pair consisting of analyte binder (capture moiety) and analyte, depending on the application for which an affinity assay is to be designed. Such substances can be used, for example, as capture moieties (analyte binders) or can be used to generate capture moieties (e.g., by employing them as haptens/antigens to generate specific antibodies) that can be used with the invention. Affinity assays, including immunoassays, can be designed in accordance with the invention to detect the presence and/or level of such substances where they are analytes in a sample. In a specific embodiment, the analyte-binding capture moieties of the invention can be used to detect these substances as analytes in a sample in the following manner: the capture moieties can be biotinylated and associated with a SA-coated solid phase support surface in accordance with the invention (e.g., with a low-input ratio biotinylated BSA coating, with SA thereon) and used to capture such substances. Alternatively, the substances listed below can be biotinylated and associated with a SA-coated solid phase support surface in accordance with the invention, and used to capture molecules that interact with them (such as, for example, antibodies or fragments thereof specific for the listed substances, binding proteins, or enzymes).

A nonlimiting list of substances that may function as one, or alternatively as the other, member of a binding pair consisting of analyte binder (capture moiety) and analyte includes: inducible nitric oxide synthase (iNOS), CA19-9, IL-1α, IL-1β, IL-2, IL-3, IL-4, IL-t, IL-5, IL-7, IL-10, IL-12, IL-13, sIL-2R, sIL-4R, sIL-6R, SIV core antigen, IL-1RA, TNF-α, IFN-gamma, GM-CSF; isoforms of PSA (prostate-specific antigen) such as PSA, pPSA, BPSA, in PSA, non-$α_1$-antichymotrypsin-complexed PSA, $α_1$-antichymotrypsin-complexed PSA, prostate kallikreins such as hK2, hK4, and hK15, ek-rhK2, Ala-rhK2, TWT-rhK2, Xa-rhK2, HWT-rhK2, and other kallikreins; HIV-1 p24; ferritin, L ferritin, troponin I, BNP, leptin, digoxin, myoglobin, B-type natriuretic peptide or brain natriuretic peptide (BNP), atrial natriuretic peptide (ANP); human growth hormone, bone alkaline phosphatase, human follicle stimulating hormone, human leutinizing hormone, prolactin; human chorionic gonadotrophin (e.g., CGα, CGβ); thyroglobulin; anti-thyroglobulin; IgE, IgG, IgG1, IgG2, IgG3, IgG4, *B. anthracis* protective antigen, *B. anthracis* lethal factor, *B. anthracis* spore antigen, *F. tularensis* LPS, *S. aureas* enterotoxin B, *Y. pestis* capsular F1 antigen, insulin, alpha fetoprotein (e.g., AFP 300), carcinoembryonic antigen (CEA), CA 15.3 antigen, CA 19.9 antigen, CA 125 antigen, HAV Ab, HAV Igm, HBc Ab, HBc Igm, HIV1/2, HBsAg, HBsAb, HCV Ab, anti-p53, histamine; neopterin; s-VCAM-1, serotonin, sFas, sFas ligand, sGM-CSFR, s1CAM-1, thymidine kinase, IgE, EPO, intrinsic factor Ab, haptoglobulin, anti-cardiolipin, anti-ds-DNA, anti-Ro, Ro, anti-La, anti-SM, SM, anti-nRNP, antihistone, anti-Scl-70, Scl-70, anti-nuclear antibodies, anti-centromere antibodies, SS-A, SS-B, Sm, U1-RNP, Jo-1, CK, CK-MB, CRP, ischemia modified albumin, HDL, LDL, oxLDL, VLDL, troponin T, troponin I, microalbumin, amylase, ALP, ALT, AST, GGT, IgA, IgG, prealbumin, anti-streptolysin, chlamydia, CMV IgG, toxo IgG, toxo IgM, apolipoprotein A, apolipoprotein B, C3, C4, properdin factor B, albumin, $\alpha_1$-acid glycoprotein, $\alpha_1$-antitrypsin, $\alpha_1$-microglobulin, $\alpha_2$-macroglobulin, anti-streptolysin O, antithrombin-III, apolipoprotein A1, apolipoprotein B, $\beta_2$-microglobulin, ceruloplasmin, complement C3, complement C4, C-reactive protein, DNase B, ferritin, free kappa light chain, free lambda light chain, haptoglobin, immunoglobulin A, immunoglobulin A (CSF), immunoglobulin E, immunoglobulin G, immunoglobulin G (CSF), immunoglobulin G (urine), immunoglobulin G subclasses, immunoglobulin M, immunoglobulin M (CSF), kappa light chain, lambda light chain, lipoprotein (a), microalbumin, prealbumin, properdin factor B, rheumatoid factor, ferritin, transferrin, transferrin (urine), rubella IgG, thyroglobulin antibody, *toxoplasma* IgM, *toxoplasma* IgG, IGF-I, IGF-binding protein (IGFBP)-3, hepsin, pim-1 kinase, E-cadherein, EZH2, and a-methylacyl-CoA racemase, TGF-beta, IL6SR, GAD, IA-2, CD-64, neutrophils CD-64, CD-20, CD-33, CD-52, isoforms of cytochrome P450, s-VCAM-1, sFas, sICAM, hepatitis B surface antigen, thromboplastin, HIV p24, HIV gp41/120, HCV C22, HCV C33, hemoglobin A1c, and GAD65, $IA_2$.

Suitable substances that may function as one, or alternatively as the other, member of a binding pair consisting of analyte binder (capture moiety) and analyte, depending on the application for which an affinity assay is to be designed, and that can be used with the present invention also include moieties, such as for example antibodies or fragments thereof, specific for any of the WHO International Biological Reference Preparations held and, characterized, and/or distributed by the WHO International Laboratories for Biological Standards (available at http:/www.who.int/bloodproducts/re_materials, updated as of Jun. 30, 2005, which lists substances that are well known in the art; the list is herein incorporated by reference).

A partial list of such suitable international reference standards, identified by WHO code in parentheses following the substance, includes: human recombinant thromboplastin (rTF/95), rabbit thromboplastin (RBT/90), thyroid-stimulating antibody (90/672), recombinant human tissue plasminogen activator (98/714), high molecular weight urokinase (87/594), prostate specific antigen (96/668), prostate specific antigen 90:10 (96/700); human plasma protein C (86/622), human plasma protein S (93/590), rheumatoid arthritis serum (W1066), serum amyloid A protein (92/680), streptokinase (00/464), human thrombin (01/580), bovine combined thromboplastin (OBT/79), anti-D positive control intravenous immunoglobulin (02/228), islet cell antibodies (97/550), lipoprotein a (IFCC SRM 2B), human parvovirus B19 DNA (99/800), human plasmin (97/536), human plasminogen-activator inhibitor 1 (92/654), platelet factor 4 (83/505), prekallikrein activator (82/530), human brain CJD control and human brain sporadic CJD preparation 1 and human brain sporadic CJD preparation 2 and human brain variant CJD (none; each cited in WHO TRS ECBS Report No. 926, 53$^{rd}$ Report, brain homogenate), human serum complement components C1q, C4, C5, factor B, and whole functional complement CH50 (W1032), human serum immunoglobulin E (75/502), human serum immunoglobulins G, A, and M (67/86), human serum proteins albumin, alpha-1-antitrypsin, alpha-2-macroglobulin, ceruloplasmin, complement C3, transferrin (W1031), anti-D negative control intravenous immunoglobulin (02/226), hepatitis A RNA (00/560), hepatitis B surface antigen subtype adw2 genotype A (03/262 and 00/588), hepatitis B viral DNA (97/746), hepatitis C viral RNA (96/798), HIV-1 p24 antigen (90/636), HIV-1 RNA (97/656), HIV-1 RNA genotypes (set of 10 I01/466), human fibrinogen concentrate (98/614), human plasma fibrinogen (98/612), raised A2 hemoglobin (89/666), raised F hemoglobin (85/616), hemoglobincyanide (98/708), low molecular weight heparin (85/600 and 90/686), unfractionated heparin (97/578), blood coagulation factor VIII and von Willebrand factor (02/150), human blood coagulation factor VIII concentrate (99/678), human blood coagulation factor XIII plasma (02/206), human blood coagulation factors II, VII, IX, X (99/826), human blood coagulation factors II and X concentrate (98/590), human carcinoembryonic antigen (73/601), human C-reactive protein (85/506), recombinant human ferritin (94/572), apolipoprotein B (SP3-07), beta-2-microglobulin (B2M), human beta-thromboglobulin (83/501), human blood coagulation factor IX concentrate (96/854), human blood coagulation factor IXa concentrate (97/562), human blood coagulation factor V Leiden, human gDNA samples FV wild type, FVL homozygote, FVL heterozygote (03/254, 03/260, 03/248), human blood coagulation factor VII concentrate (97/592), human blood coagulation factor VIIa concentrate (89/688), human anti-syphilitic serum (HS), human anti-tetanus immunoglobulin (TE-3), human antithrombin concentrate (96/520), human plasma antithrombin (93/768), human anti-thyroglobulin serum (65/93), anti-toxoplasma serum (TOXM), human anti-toxoplasma serum (IgG) (01/600), human anti-varicella zoster immunoglobulin (W1044), apolipoprotein A-1 (SP1-01), human anti-interferon beta serum (G038-501-572), human anti-measles serum (66/202), anti-nuclear ribonucleoprotein serum (W1063), anti-nuclear-factor (homogeneous) serum (66/233), anti-parvovirus B19 (IgG) serum (91/602), anti-poliovirus serum Types 1,2,3 (66/202), human anti-rabies immunoglobulin (RAI), human anti-rubella immunoglobulin (RUBI-1-94), anti-smooth muscle serum (W1062), human anti-double-stranded DNA serum (Wo/80), human anti-E complete blood-typing serum (W1005), human anti-echinococcus serum (ECHS), human anti-hepatitis A immunoglobulin (97/646), human anti-hepatitis B immunoglobulin (W1042), human anti-hepatitis E serum (95/584), anti-human platelet antigen-1a (93/710), anti-human platelet antigen-5b (99/666), human anti-interferon alpha serum (B037-501-572), human alphafetoprotein (AFP), ancrod (74/581), human anti-A blood typing serum (W1001), human anti-B blood typing serum (W1002), human anti-C complete blood typing serum (W1004), anti-D (anti-Rh0) complete blood-typing reagent (99/836), human anti-D (anti-Rh0) incomplete blood-typing serum (W1006), and human anti-D immunoglobulin (01/572).

Other examples of suitable substances that may function as one, or alternatively as the other, member of a binding pair consisting of analyte binder (capture moiety) and analyte, depending on the application for which an affinity assay is to be designed include compounds that can be used as haptens to generate antibodies capable of recognizing the compounds, and include but are not limited to, any salts, esters, or ethers, of the following: hormones, including but not limited to progesterone, estrogen, and testosterone, progestins, corticosteroids, and dehydroepiandrosterone, and any non-protein/non-polypeptide antigens that are listed as international reference standards by the WHO. A partial list of such suitable international reference standards, identified by WHO code in parentheses following the substance, includes vitamin B12 (WHO 81.563), folate (WHO 95/528), homocystein, transcobalamins, T4/T3, and other substances disclosed in the WHO catalog of International Biological Reference Preparations (available at the WHO website, for example at page http://www.who.int/bloodproducts/ref_materials/, updated Jun. 30, 2005), which is incorporated herein by reference. The methods and compositions described herein can comprise one or more of the aforementioned WHO reference standards or a mixture containing a reference standard.

In at least one embodiment, the present invention provides a binding surface with two or more different capture moieties.

Other examples of substances that may function as one, or alternatively as the other, member of a binding pair consisting of analyte binder (capture moiety) and analyte, depending on the application for which an affinity assay is to be designed include drugs of abuse. Drugs of abuse include, for example, the following list of drugs and their metabolites (e.g., metabolites present in blood, in urine, and other biological materials), as well any salts, esters, or ethers, thereof: heroin, morphine, hydromorphone, codeine, oxycodone, hydrocodone, fentanyl, demerol, methadone, darvon, stadol, talwin, paregoric, buprenex; stimulants such as, for example, amphetamines, methamphetamine; methylamphetamine, ethylamphetamine, methylphenidate, ephedrine, pseudoephedrine, ephedra, ma huang, methylenedioxyamphetamine (MDS), phentermine, phenylpropanolamine; amiphenazole, bemigride, benzphetamine, bromatan, chlorphentermine, cropropamide, crothetamide, diethylpropion, dimethylamphetamine, doxapram, ethamivan, fencamfamine, meclofenoxate, methylphenidate, nikethamide, pemoline, pentetrazol, phendimetrazine, phenmetrazine, phentermine, phenylpropanolamine, picrotoxine, pipradol, prolintane, strychnine, synephrine, phencyclidine and analogs such as angel dust, PCP, ketamine; depressants such as, for example, barbiturates, gluthethimide, methaqualone, and meprobamate, methohexital, thiamyl, thiopental, amobarbital, pentobarbital, secobarbital, butalbital, butabarbital, talbutal, and aprobarbital, phenobarbital, mephobarbital; benzodiazapenes such as, for example, estazolam, flurazepam, temazepam, triazolam, midazolam, alprazolam, chlordiazepoxide, clorazepate, diazepam, halazepam, lorazepam, oxazepam, prazepam, quazepam, clonazepam, flunitrazepam; GBH drugs such as gamma hydroxyl butyric acid and gamma butyrolactone; glutethimide, methaqualone, meprobamate, carisoprodol, zolpidem, zaleplon; cannabinoid drugs such as tetrahydracannabinol and analogs; cocaine, 3-4 methylenedioxymethamphetamine (MDMA); hallucinogens such as, for example, mescaline and LSD.

Other examples of substances that may function as one, or alternatively as the other, member of a binding pair consisting of analyte binder (capture moiety) and analyte, depending on the application for which an affinity assay is to be designed include steroids and other drugs associated with performance enhancement, including those commonly encountered in illicit markets, or employed as ergogenic aids, such as, for example, the following compounds and any salts, esters, or ethers thereof: testosterone (including its esters with moieties such as, for example, enanthate, cypionate, and propionate), dihydrotestosterone (DHT), tetrahydrogestrinone, nandrolone, nortestosterone, methenolone, stanozolol, methandrostenolone, methandienone, androstenedione (e.g., 5a-androstan-3,17-dione), androstenediol such as 1-androstenediol (3β,17β-dihydroxy-5α-androst-1-ene;), 4-androstenediol (3b,17b-dihydroxy-androst-4-ene), 5-androstenediol (3b,17b-dihydroxy-androst-5-ene), androstendiones, such as 1-androstenedione ([5a]-androst-1-en-3,17-dione), 4-androstenedione (androst-4-en-3,17-dione), 5-androstenedione (androst-5-en-3,17-dione), norandrostenedione, 19-norandrostenediol, 19-norandrostenedione, norandrostenediol, dehydroepiandrosterone (DHEA), boldenone, fluoxymesterone, methandriol, methyltestosterone, oxandrolone, oxymetholone, trenbolone, clostebol, dehydrochloromethyltestosterone, dromostanolone, epitrenbolone, gestrinone, mesterolone, methanedienone, methenolone, norethandrolone, oxandrolone, oxymetholone, tetrahydrogestrinone (THG), trenbolone, clenbutorol, and steroids included in the Anabolic Steroid Control Act of 2004 (incorporated herein by reference), including 3b,17b-dihydroxy-5a-androstane; 3a,17b-dihydroxy-5a-androstane; androstanedione, bolasterone (7a,17a-dimethyl-17b-hydroxyandrost-4-en-3-one), boldenone (17b-hydroxyandrost-1,4,-diene-3-one), calusterone (7b,17a-dimethyl-17b-hydroxyandrost-4-en-3-one), clostebol (4-chloro-17b-hydroxyandrost-4-en-3-one), dehydrochlormethyltestosterone (4-chloro-17b-hydroxy-17a-methyl-androst-1,4-dien-3-one), 4-dihydrotestosterone (17b-hydroxy-androstan-3-one), drostanolone (17b-hydroxy-2a-methyl-5a-androstan-3-one), ethylestrenol (17a-ethyl-17b-hydroxyestr-4-ene), fluoxymesterone (9-fluoro-17a-methyl-11b,17b-dihydroxyandrost-4-en-3-one), formebolone (2-formyl-17a-methyl-11a,17b-dihydroxyandrost-1,4-dien-3-one), furazabol (17a-methyl-17b-hydroxyandrostano[2,3-c]-furazan), 18a-homo-17b-hydroxyestr-4-en-3-one (13b-ethyl-17b-hydroxygon-4-en-3-one), 4-hydroxytestosterone (4,17b-dihydroxy-androst-4-en-3-one), 4-hydroxy-19-nortestosterone (4,17b-dihydroxy-estr-4-en-3-one), estanolone (17a-methyl-17b-hydroxy-5a-androstan-3-one), mesterolone (1a-methyl-17b-hydroxy-[5a]-androstan-3-one), methandienone (17a-methyl-17b-hydroxyandrost-1,4-dien-3-one), methandriol (17a-methyl-3b,17b-dihydroxyandrost-5-ene), methenolone (1-methyl-17b-hydroxy-5a-androst-1-en-3-one), ethyltestosterone (17a-methyl-17b-hydroxyandrost-4-en-3-one), mibolerone (7a,17a-dimethyl-17b-hydroxyestr-4-en-3-one), nandrolone (17b-hydroxyestr-4-en-3-one), norandrostenediol, 19-nor-4-androstenediol (3b, 17b-dihydroxyestr-4-ene), 19-nor-4-androstenediol (3a, 17b-dihydroxyestr-4-ene), 19-nor-5-androstenediol (3b, 17b-dihydroxyestr-5-ene), 19-nor-5-androstenediol (3a, 17b-dihydroxyestr-5-ene), norandrostenedione, 19-nor-4-androstenedione (estr-4-en-3,17-dione), 19-nor-5-androstenedione (estr-5-en-3,17-dione), norbolethone (18a-homo-17b-hydroxypregna-4-en-3-one), norclostebol (4-chloro-17b-hydroxyestr-4-en-3-one), norethandrolone (17a-ethyl-17b-hydroxyestr-4-en-3-one), oxandrolone (17a-methyl-17b-hydroxy-2-oxa-[5a]-androstan-3-one), oxymesterone (17a-methyl-4,17b-dihydroxyandrost-4-en-3-one), oxymetholone (17a-methyl-2-hydroxymethylene-17b-hydroxy-[5a]-androstan-3-one), stanozolol (17a-methyl-17b-hydroxy-[5a]-androst-2-eno[3, 2-c]-pyrazole), stenbolone (17b-hydroxy-2-methyl-[5a]-androst-1-en-3-one), testolactone (13-hydroxy-3-oxo-13,17-secoandrosta-1,4-dien-17-oic acid lactone), 1-testosterone (17b-hydroxy-5a-androst-1-en-3-one), testosterone (17b-hydroxyandrost-4-en-3-one), tetrahydrogestrinone (13b,17a-diethyl-17b-hydroxygon-4,9,11-trien-3-one), trenbolone (17b-hydroxyestr-4,9,11-trien-3-one).

Other examples of substances that may function as one, or alternatively as the other, member of a binding pair consisting of analyte binder (capture moiety) and analyte, depending on the application for which an affinity assay is to be designed include antibiotics and other drugs administered to animals (including human beings) and whose detection is useful in clinical practice, and whose detection in a biological preparation can be achieved using, for example, an immunoassay. Examples of such drugs include antibiotics such as those listed in the WHO International Biological Reference preparations (available at http://www.who.int/bloodproducts/ref_ materials/Ant-Sept05.pdf, updated as of 21 Sep. 2005, incorporated herein by reference). Examples include gentamicin (92/670), streptomycin (76/539), tobramycin (82/510), and vancomycin (50/020).

In at least one embodiment, the present invention provides a binding surface with at least two or more different capture moieties.

Any of the features of the various embodiments described herein can be used in conjunction with features described in connection with any other embodiments disclosed. For example, features disclosed in connection with the compositions of the invention can be employed in any methods described herein, etc. Features described in connection with the various or specific embodiments are not to be construed as not suitable in connection with other embodiments disclosed herein unless such exclusivity is explicitly stated or implicit from the context.

Certain embodiments of the invention are illustrated in the accompanying Figures and Examples, which are provided to illustrate certain embodiments of the invention, and are not meant to impose limitations on the invention.

EXAMPLES

Example 1

Low Input Ratio Biotinylation of Bovine Serum Albumin

BSA was biotinylated with sulfo-NHS-LC-biotin (sulfosuccinimidyl-6-[biotinamido]hexanoate; Pierce Biotechnology Inc./Thermo Scientific) at various molar input ratios of biotin to BSA (see Table 1). Briefly, sulfo-NHS-LC-biotin (556.59 g/mol) was dissolved in DMF (dimethylformamide) at a concentration of 30 milligrams per milliliter (mg/mL), and lyophilized BSA (bovine serum albumin, protease free; Celliance Corporation, a Serologicals Company; 66,000 g/mol) was dissolved in 0.05 M borate buffer pH 8.2 at a concentration of 15 to 20 mg/mL. The sulfo-NHS-LC-biotin solution was added to the BSA solution such that the final molar input ratio of sulfo-NHS-LC-biotin to BSA was from 3.4 to 30 (mol sulfo-NHS-LC-biotin:mol BSA). The reaction was incubated for 2 hours at 4° C., and then immediately dialyzed (i.e., diafiltration or dialysis) with 0.05M borate buffer pH 8.2 to remove excess sulfo-NHS-LC-biotin (i.e., biotin reagent, and hydrolyzed biotin reagent, free biotin). This general procedure was used throughout in preparing low-input ratio biotinylated BSA.

Degree of biotinylation can be estimated using any method known in the art for quantitating biotin. One suitable method is the HABA colorimetric assay, which employs 4'-hydroxyazobenzene-2-carboxylic acid (HABA), which is selective for biotin. The moles of biotin bound per mole of BSA were estimated by HABA analysis. Results are shown in Table 1.

Stability analysis of 17 independent biotinylation lots of biotinylated BSA was completed by coating 25 mg/mL tosylactivated PMPs (Dynal® DYNABEADS MyOne Tosylactivated, 1.0 micron diameter, Invitrogen Corporation) with biotin-BSA for 18-24 hours at 37-42° C. in 0.1 M borate buffer pH 9.0-9.5 (0.030-0.050 milligrams biotin-BSA per mg PMP), washing the microparticles three times with TBS (0.02M Tris, 0.15 M sodium chloride) pH 7.4, blocking the biotin-BSA coated microparticle surface with 0.4%-0.6% (w/v) tri-block copolymer Pluronic® F108 (Pluronic® F-108 NF Frill; BASF) in TBS pH 7.4 for 4-4.5 hours at 37-42° C., washing the microparticles three times with TBS pH 7.4, dispersing the biotin-BSA microparticles in 0.4%-0.6% (w/v) Pluronic® F108 in TBS pH 7.4, coating the biotin-BSA microparticles with SA (frozen, never lyophilized, SA21 SAplus, Prozyme, Inc.) in TBS pH 7.4 for 30-50 minutes at room temperature (0.025-0.050 milligrams SA per mg biotin-BSA PMP), washing the microparticles three times with TBS pH 7.4 with sodium azide (0.1% w/v), washing the microparticles three times with Access® Free T4 assay-specific microparticle buffer, diluting the microparticles from 25 mg/mL to 0.35 mg/mL with Access® Free T4 assay-specific microparticle buffer, incubating the biotin-BSA-coated, SA-coated microparticles at 4° C. or 37° C. for 3 days, and testing the ability of the biotin-BSA-coated, SA-coated microparticles to bind biotinylated Free T4-specific antibody in the Access® Free T4 Assay (Beckman Coulter, Inc.). Stability was determined by calculating the average of the individual Free T4 calibrator RLU (relative light units, signal, or response) recoveries. The Access® Free T4 assay uses six different calibrators (S0, S1, S2, S3, S4, and S5) with antigen levels from 0 ng/mL to 6 ng/mL (see Table 4). Recovery was calculated by dividing the 37° C. calibrator RLU response by the 4° C. calibrator RLU response, and multiplying the result by 100%. Stability was calculated by averaging the recovery for all six calibrators. Results are shown in Table 1.

Stability was indicative of the change in SA binding capacity after incubating the solid phase at 4° C. or 37° C. for 3 days. A decrease in stability is due to sloughing or dissociation of passively bound biotin or biotin reagent from biotin-BSA conjugates (see FIG. 11; broken line: 37° C.; solid line: 4° C.), and the subsequent capture of the free biotin or biotin reagent by SA over time. Results indicated that biotin-BSA prepared at high molar input ratios (i.e., 8:1, 15:1, 30:1) displays very poor stability. As the molar input ratio of biotin reagent to BSA is decreased from 30:1 to 4:1, stability improved from 4% to 100%.

TABLE 1

STABILITY ANALYSIS OF BIOTIN-BSA SOLID PHASE COATED
WITH SA FOR 17 INDEPENDENT BIOTINYLATION LOTS

| BIOTINYLATION LOT | *PMP LOT | MOLAR INPUT RATIO (MOLS BIOTIN PER MOL BSA) | HABA (MOLS BIOTIN PER MOL BSA) | STABILITY (%) |
|---|---|---|---|---|
| C-0402-SP-129 | 5135:5 | 30:1 | 5:1 | 4.1 |
| C-0406-SP-137A | RP4162 | 4:1 | 1.6 | 93.9 |
| C-0406-SP-138 | RP4163 | 8:1 | 3.8 | 69.1 |
| C-0406-SP-139A | RP4164 | 15:1 | 8.9 | 24.8 |
| C-0406-SP-137B | RP4167 | 4:1 | 1.4 | 100.8 |
| C-0406-SP-139B | RP4168 | 15:1 | 9.2 | 16.0 |
| C-0406-SP-142 | RP4217 | 4:1 | 1.8 | 96.4 |
| C-0406-SP-144 | RP4219 | 4:1 | 1.6 | 102.2 |

TABLE 1-continued

STABILITY ANALYSIS OF BIOTIN-BSA SOLID PHASE COATED
WITH SA FOR 17 INDEPENDENT BIOTINYLATION LOTS

| BIOTINYLATION LOT | *PMP LOT | MOLAR INPUT RATIO (MOLS BIOTIN PER MOL BSA) | HABA (MOLS BIOTIN PER MOL BSA) | STABILITY (%) |
|---|---|---|---|---|
| C-0406-SP-146 | RP4221 | 4:1 | 1.9 | 100.0 |
| C-0410-SP-155A | RP4443 | 4:1 | 1.5 | 100.1 |
| C-0410-SP-155B | RP4444 | 4:1 | 1.3 | 98.4 |
| C-0410-SP-156 | RP4445 | 4:1 | 1.7 | 108.3 |
| C-0501-SP-157 | RP4658 | 4.6:1 | 2.3 | 101.7 |
| 519499 | RP4659 | 3.4:1 | 1.2 | 114.4 |
| 519500 | P4660 | 4:1 | 1.8 | 109.2 |
| 515033 | P4661 | 4:1 | 1.8 | 102.1 |
| 515-34 | P4696 | 4:1 | 2.0 | 107.1 |

*PMP = paramagnetic microparticle

BSA was biotinylated at a molar input ratio of 30 mols sulfo-NHS-LC-biotin per mol BSA. The 30:1 biotinylated BSA was attached to Dynal® MyOne Tosylactivated PMPs by coating 25 mg/mL tosylactivated PMPs with biotin-BSA for 18-24 hours at 37-42° C. in 0.1 M borate buffer pH 9.0-9.5 (0.030-0.050 milligrams biotin-BSA per mg PMP), washing the microparticles three times with TBS pH 7.4, blocking the biotin-BSA coated microparticle surface with 0.4% to 0.6% (w/v) Pluronic® F108 in TBS pH 7.4 for 4-4.5 hours at 37-42° C., washing the microparticles three times with TBS pH 7.4, dispersing the biotin-BSA microparticles in 0.4%-0.6% (w/v) Pluronic® F108 in TBS pH 7.4, coating the biotin-BSA microparticles with SA in TBS pH 7.4 for 30-50 minutes at room temperature (0.025-0.050 milligrams SA per mg PMP), and washing the microparticles three times with TBS pH 7.4. The 25 mg/mL biotin-BSA-coated, SA-coated PMP were placed at 4° C. or 37° C. for three days, and placed on a magnet for 10 minutes to separate the PMP (remove the microparticles from the 4° C. or 37° C. buffers). The 4° C. and 37° C. microparticle-free supernatant fluids were collected, and the supernatant fluids were analyzed using size-exclusion high performance liquid chromatography (SEC-HPLC; Beckman Coulter System Gold HPLC System, 32 KARAT™ 5.0 software, Phenomenex 300×7.80 mm BioSep-SEC-S 3000 column, PBS pH 7.2 mobile phase, 1.0 mL/min flow rate, 0.050 mL sample volume, 17 minute run time, 200 to 400 nm photodiode array detection).

SEC-HPLC analysis at 210 nm of the 37° C. supernatant fluid revealed a significantly higher level of low molecular weight analytes at both 10.8 minutes retention time (RT) and 12.4 minute RT compared to the 4° C. supernatant fluid. These peaks were believed to be biotin and/or biotin reagent that had passively absorbed to the BSA molecules during the biotinylation process at a 30:1 (biotin reagent:BSA) input ratio, and were not removed by dialysis or desalting. The results also indicate that there is no detectable (below the limit of detection of the method) BSA or SA in the supernatant fluid (RT of 7.8 to 8.2 min.), and the biotin-BSA conjugate and/or SA is not sloughing from the solid phase.

The SEC-HPLC results support the stability results (see Table 1), in that the 30 biotin reagent:1 BSA sample had the most significant decrease in 37° C. stability (95.9% decrease in stability, or 4.1% stability) compared to 4° C., and also exhibited the presence of a significant amount of low molecular weight analyte(s) in the 37° C. supernatant fluid compared to the 4° C. supernatant fluid. A decrease in stability is due to sloughing or dissociation of passively bound biotin or biotin reagent from biotin-BSA conjugates, and the subsequent capture of the free biotin or biotin reagent by SA over time.

The biotin-BSA coating process was optimized by biotinylating BSA using 4 mols of sulfo-NHS-LC-biotin per mol of BSA, offering 30, 40, 50, or 60 micrograms of biotin-BSA per mg of microparticles (Dynal® DYNABEADS MyOne Tosylactivated, 1.0 micron diameter, Invitrogen Corporation), incubating the biotin-BSA with the microparticles for 2, 4, or 18 hours at 37° C. or 40° C. in 0.1M Borate pH 9.5, washing the microparticles three times with TBS pH 7.4, blocking the microparticles with TBS containing 0.4% (w/v) Pluronic® F108 pH 7.4 for 4 hours at 37° C., washing the microparticles three times with TBS pH 7.4, dispersing the biotin-BSA microparticles in TBS containing 0.4% (w/v) Pluronic® F108, coupling SA by adding 35 micrograms SA per mg microparticles and incubating for 30 minutes at room temperature, and washing the biotin-BSA-coated, SA-coated microparticles three times with TBS pH 7.4.

Results of assay performance testing (Access® Free T4 and Access® AccuTnI assays; Beckman Coulter, Inc.), and biotinylated IgG binding capacity testing, indicated that the biotin-BSA coating process is robust when 30 to 50 mg biotin-BSA are added per mg microparticles, at a microparticle concentration of 25 mg/mL, in 0.1 M Borate buffer pH 9.5, and incubated for 18 to 24 hours at 37° C. to 42° C. Briefly, the $^{125}$I-labelled biotinylated IgG method is used to assess binding capacity by labeling biotinylated IgG and non-biotinylated IgG with $^{125}$I using a standard iodination procedure (antibody and biotinylated antibody each are incubated with Na$^{125}$I and chloramine T trihydrate at room temperature, each reaction is stopped with sodium-meta-bisulfite, and the $^{125}$I labeled non-biotinylated antibody and $^{125}$I labeled biotinylated antibody are each purified using SEPHADEX G-50 columns preconditioned with 0.5% BSA/PBS/0.1% sodium azide), the total CPM (counts per minute)/mg of biotinylated and of non-biotinylated $^{125}$I-IgG are calculated using a gamma counter, the SA-coated microparticles are offered a molar excess of either $^{125}$I-biotin-IgG (active absorption via biotin-binding domains) or $^{125}$I-IgG (passive absorption or non-specific binding), the microparticles are washed 5 times with wash buffer, the washed microparticles are placed in a gamma counter to determine total CPM, and the amount of biotin-IgG specifically captured is determined by subtracting the CPM of the $^{125}$I-IgG coated SA microparticles (non-specific binding control) from the CPM of the $^{125}$I-biotin-IgG SA microparticles.

Example 2

Non-Saturation Decreases Binding Capacity but Increases Assay Signal

A non-saturated and orientated binding surface using a biotin/SA system was prepared with biotin-BSA prepared at a low molar input ratio of biotin to BSA (4:1) using PMPs. Briefly, a batch of microparticles having a non-saturated and orientated binding surface was prepared by coating Dynal® AKT-100 tosylactivated PMPs with low input ratio biotinylated BSA, blocking the biotin-BSA microparticles with Pluronic® F108, dispersing the blocked biotin-BSA microparticles in Pluronic® F108, and finally coating the biotin-BSA microparticles with SA. See Table 2, "BCI Sample." For comparison, a commercially available biotin-binding microparticle (Dynal® DYNABEADS MyOne Streptavidin T1, Invitrogen Corporation) was tested. See Table 2, "Dynal® Control." The non-saturated surface and the commercially available biotin-binding surface were each prepared using the same raw microparticle (Dynal® MyOne tosylactivated 1.0 micron PMP from Invitrogen Corporation)

The non-saturated and commercially available biotin-binding (i.e., SA-coated) surfaces were tested for their biotin binding capacity using a $^{14}$C-biotin binding capacity test (Invitrogen Corporation). Results are shown in Table 2. Calibrator level is presented in nanogram per mL. The biotin binding capacity of the commercially available microparticles was 1,400 pmol biotin/mg, whereas the biotin binding capacity of the microparticles having a non-saturated binding surface prepared in accordance with the invention was only 214 pmol biotin/mg. Thus, the commercially available biotin-binding microparticles displayed a binding capacity for biotin over six-fold higher than the same diameter microparticles prepared according to the invention.

The microparticles were also tested for their capacity to bind biotinylated IgG. The commercially available microparticles displayed a biotinylated IgG binding capacity of 20.0 micrograms of biotinylated IgG per mg of microparticles, whereas the microparticles in accordance with the invention displayed a binding capacity of 6.7 micrograms of biotinylated IgG per mg of microparticles. Thus, the commercially available biotin-binding microparticles displayed a biotinylated IgG binding capacity about three-fold higher than the microparticles according to the invention. However, the biotin binding capacity of the commercially available microparticle was over six-fold higher than the microparticles according to the invention.

TABLE 2

COMPARISON OF THE BINDING CAPACITIES OF NON-SATURATED AND COMMERCIALLY AVAILABLE BIOTIN-BINDING MICROPARTICLES

| MICROPARTICLE PREPARATION* | BIOTIN BINDING CAPACITY (PMOL BIOTIN/MG) | BIOTINYLATED IGG BINDING CAPACITY (µG IGG/MG MICROPARTICLES) |
|---|---|---|
| Commercially Available Biotin-binding (Invitrogen Corp.) | 1400 | 20.0 |
| Non-saturated | 214 | 6.7 |

*Both the commercially available and non-saturated microparticles were prepared using the same lot of Dynal ® AKT-100 tosylactivated PMPs The functional performance of commercially available biotin-binding microparticles was compared with the performance of non-saturated microparticles prepared in accordance with the invention in an assay for a protein, troponin I. Briefly, commercially available one micron diameter biotin-binding microparticles (Dynal® DYNABEADS MyOne Streptavidin T1, Invitrogen Corporation) coated with recombinant SA, and non-saturated one micron diameter microparticles coated with SA in accordance with the invention, were used to assay for troponin I using the Access® AccuTnI Assay (Beckman Coulter, Inc.), a sandwich assay, by treating the SA-coated microparticles with biotinylated anti-troponin I and measuring assay response to troponin I calibrator (Beckman Coulter, Inc.). Results are shown in Table 3.

TABLE 3

COMPARISON OF INVENTIVE COATING PROCESS TO COMMERCIAL DYNAL ® METHOD USING TOSYLACTIVATED MICROPARTICLES IN THE ACCESS ® ACCUTNI ASSAY

| PARAMETER | DYNAL ® METHOD (RLUS) | BCI METHOD (RLUS) |
|---|---|---|
| CALIBRATOR RESPONSE (NG/ML) | | |
| S0 = 0 | 13,023 | 8,116 |
| S1 = 0.3 | 49,030 | 54,986 |
| S2 = 1.2 | 149,472 | 194,922 |
| S3 = 5 | 587,250 | 779,833 |
| S4 = 25 | 2,870,740 | 3,829,280 |
| S5 = 100 | 9,611,635 | 12,422,050 |
| % CV CALIBRATOR RESPONSE | | |
| S0 = 0 | 1.9 | 4.3 |
| % CV CALIBRATOR DOSE (NG/ML) | | |
| S1 = 0.3 | 1.0 | 1.8 |
| S2 = 1.2 | 1.8 | 0.7 |
| S3 = 5 | 3.6 | 0.4 |
| S4 = 25 | 3.2 | 1.0 |
| S5 = 100 | 4.6 | 1.7 |
| RATIOS | | |
| S1/S0 | 3.8 | 6.8 |
| S5/S0 | 738 | 1531 |

Table 3 illustrates that, over a range of calibrator levels (S1 to S5), non-saturated microparticles in accordance with the invention display higher RLU readings than commercially available microparticles, and lower background RLU readings (S0) than commercially available microparticles. This result is surprising and unexpected because the non-saturated microparticles in accordance with the invention display a lower biotin binding capacity than commercially available biotin-binding microparticles (see Table 2). Calibrator response was higher for the non-saturated microparticles over nearly the entire range. Assay precision, measured as % CV Calibrator Response of the S0 (CV=coefficient of variation), was over two-fold greater for the non-saturated microparticles. However, the non-saturated microparticles had significantly lower S0 RLU response compared to the commercially available microparticles (8,116 vs. 13,023), and a small difference in RLUs between repetitions can result in greater % CV as the RLU signal decreases. Assay imprecision expressed as % CV Calibrator Dose, was, on average, significantly lower for the non-saturated microparticles. Regarding dynamic range, ratios of S1/S0 and S5/S0 were about two-fold higher for the non-saturated microparticles. Thus, although microparticles in accordance with the invention bind less biotin (and, accordingly, less biotinylated IgG), they unexpectedly perform better in a functional affinity assay, and have decreased noise or non-specific binding, compared to commercially available microparticles.

The performance of commercially available 2.8 micron diameter SA-coated microparticles (Dynal® DYNABEADS M-280 Streptavidin, biotin-binding capacity of 650 to 900 picomoles of biotin per mg, Invitrogen Corporation) was compared with the performance of 1.0 micron SA-coated microparticles prepared in accordance with the invention (biotin-binding capacity of about 214 picomoles of biotin per mg; see Table 2) in the Access® Free T4 assay (Beckman Coulter, Inc.). Free T4 was assayed using the Access® Free T4 assay, a competitive assay, by treating SA-coated microparticles (commercially available SA-coated 2.8 micron diameter PMPs for "Dynal® Method"; 1.0 micron diameter SA-coated PMPs prepared in accordance with the invention for "BCI Method") with biotinylated anti-T4 in accordance with the invention and by measuring assay response to a T4 calibrator (Beckman Coulter, Inc.). Assays were performed on an Access® 2 Immunoassay System (Beckman Coulter, Inc.), and results in RLUs obtained on this system are shown in Table 4.

TABLE 4

COMPARISON OF INVENTIVE COATING PROCESS ON 1.0 MICRON PMPS WITH A COMMERCIAL METHOD USING TOSYLACTIVATED 2.8 MICRON PMPS IN A FREE T4 ASSAY

| PARAMETER | DYNAL ® METHOD (RLUS) | BCI METHOD (RLUS) |
|---|---|---|
| CALIBRATOR RESPONSE (NG/ML) | | |
| S0 = 0 | 1,409,355 | 1,486,955 |
| S1 = 0.5 | 616,624 | 672,265 |
| S2 = 0.96 | 302,663 | 331,858 |
| S3 = 1.97 | 113,027 | 119,425 |
| S4 = 2.96 | 68,655 | 70,185 |
| S5 = 6.08 | 34,120 | 34,385 |
| % CV CALIBRATORS | | |
| S1 = 0.5 | 1.7 | 1.4 |
| S2 = 0.96 | 1.1 | 2.1 |
| S3 = 1.97 | 1.8 | 2.0 |
| S4 = 2.96 | 2.7 | 0.0 |
| S5 = 6.08 | 1.0 | 3.8 |
| RATIOS | | |
| S1/S0 | 43.8 | 45.2 |
| S2/S0 | 21.5 | 22.3 |
| S3/S0 | 8.0 | 8.0 |
| S4/S0 | 4.9 | 4.7 |
| S5/S0 | 2.4 | 2.3 |

As shown in Table 4, the 1.0 micron SA-coated microparticles prepared in accordance with the invention gave about the same signal for the analyte (Free T4) as the commercially available 2.8 micron diameter SA-coated microparticles. This result is surprising and unexpected because the non-saturated microparticles in accordance with the invention display a lower biotin binding capacity than the commercially available antibiotin microparticles (Dynal® DYNABEADS M-280 Streptavidin, biotin-binding capacity of 650 to 900 picomoles of biotin per mg, Invitrogen Corporation). Preparing microparticles in accordance with the invention, as illustrated in the tables above (see Tables 2, 3, and 4), results in non-saturation of the binding surface, so that the number of ligands (biotins) is reduced. Microparticles in accordance with the invention bind less (214 picomoles per mg for microparticles in accordance with the invention, compared to 650 to 900 picomoles per mg for commercially available DYNABEADS M-280 microparticles, and greater than 1,000 picomoles per mg for DYNABEADS MyOne SA T1 microparticles), but they function better (see Table 3 and Table 4). The 1.0 micron microparticles in accordance with the invention bind slightly less than a 2.8 micron microparticle, but the inventive microparticles generate more signal.

Overall, the results establish that non-saturated microparticles in accordance with the invention, although they have lower binding capacity than commercially available microparticles, yield assay signals that are as good as, or better than, commercially available microparticles. This is true even for inventive binding surfaces with significantly lower binding capacities than commercially available microparticles.

Example 3

Making a Non-Saturated Surface Employing a Dispersion Step

Biotin-BSA prepared using a low molar input ratio of biotinylating reagent to BSA (4:1) was used in a dispersion method for making a non-saturated binding surface. Briefly, the biotin-BSA (prepared as described above) was covalently attached to Dynal® microparticles as described above to yield a surface that was non-saturated with respect to the number of biotins per unit support surface area. The coated microparticles were then employed in a dispersion step before adding SA.

Initial studies used a hemacytometer (microscope analysis) to assess the aggregation state of biotin-BSA coated microparticles, prepared as described above, (1) prior to the addition of SA, (2) after the drop-by-drop addition of a 10 mg/mL solution of biotin-BSA coated microparticles to a continuously mixing solution of SA (0, 125, 250, 375, 500, 750, or 1000 micrograms SA per mL), and (3) after the addition of different amounts of an 18 mg/mL SA solution (25, 50, 75, 100, 150 or 200 micrograms SA per mg micrparticles) to a continuously mixing solution of 10 mg/mL biotin-BSA coated microparticles. Hemacytometer results were reported as monomers (single microparticles), dimers (two-microparticle aggregates), trimers (three-microparticle aggregates), small aggregate (4- to 10-microparticle aggregates), and large aggregate (>10-microparticle aggregates). Aggregates are defined as the association of two or more biotin-BSA microparticles via SA cross-linking (i.e., SA is multivalent with four subunits, and each subunit has one biotin-binding domain). Hemacytometer results indicated that the biotin-BSA microparticles were monodisperse (only monomers and dimers) prior to the addition of SA, mostly aggregated (large aggregates) when biotin-BSA microparticles were titrated (drop-by-drop) into SA solutions up to 750 micrograms SA per milliliter, monodisperse (trimers, dimers, and monomers) when biotin-BSA microparticles were titrated (drop-by-drop) into a SA solutions of 1000 micrograms SA per milliliter, and highly aggregated (large aggregates) when SA was added to biotin-BSA microparticles at all concentrations tested. As used herein, the term substantially monodisperse means a population of microparticles that substantially exist only as monomers and dimers.

The biotin-BSA-coated, SA-coated microparticles prepared by the drop-by-drop addition of biotin-BSA coated microparticles to a mixing solution of SA, or by the addition of a SA solution to a mixing solution of biotin-BSA microparticles, could be driven to a temporary monodisperse state (mostly trimers, with dimers and monomers) by subjecting the SA-coated microparticles to sonication energy (2×300 Watts for 60 seconds) with mixing, but the microparticles did not remain monodisperse over time, and became highly aggregated again. Sonication energy did not result in permanently monodisperse biotin-BSA-coated, SA-coated microparticles, and could not mitigate the propensity of the biotin-BSA microparticles to aggregate due to SA crosslinking.

Hemacytometer studies were completed to determine the amount of Pluronic® F108 (17 dilution levels from 0 µM to 1000 µM Pluronic® F108 in water) required for hydrophobic microparticle monodispersion (1.03 micron polystyrene PMP, Cat. No. M1-070/40, EMD Biosciences, Inc.). Results of these studies indicated that M1-070/40 microparticles were substantially monodisperse (ie. only monomers and dimers) at Pluronic® F108 concentrations from 27.04 mg Pluronic® F108/mg microparticles (dilution level 6) to 2027.7 µg Pluronic® F108/mg microparticles (dilution level 15). Microparticles were aggregated at Pluronic® F108 concentrations less than 27.04 µg Pluronic® F108/mg microparticles, and at concentrations greater than 2027.7 µg Pluronic® F108/mg microparticles (most likely due to multi-layer stacking of the tri-block copolymers). Surface area calculations predicted that a theoretical monolayer of Pluronic® F108 would require at least 4.1 µg Pluronic® F108/mg microparticles, assuming an interfacial surface area of 20 nm$^2$ per Pluronic® F108 molecule, and a microparticle surface area of 38.38 cm$^2$/mg (based on a 1.03 µm, smooth surfaced, perfectly round sphere). It should be noted that the M1-070/40 microparticles were not uniform in size or smooth surfaced (heterogeneous size distribution), and contained a large population of fines less than 1.03 micron in diameter (based on microparticle size analysis using a Beckman Coulter LS13 320 laser diffraction particle sizer). Both microparticle fines and a rough microparticle surface would indicate that the M1-070/40 microparticles have a greater surface area per mg than calculated above. The hemacytometer results support this assumption since it required greater than 27 µg Pluronic® F108/mg microparticles for microparticle monodispersion. Results of this study indicated that Pluronic® F108 can result in microparticle monodispersion at concentrations from 27.04 to 2027.7 µg Pluronic® F108/mg microparticles (dilution levels 6 to 15).

The specific lots of microparticles (Dynal® DYNABEADS MyOne Tosylactivated, 1.0 micron diameter, Invitrogen Corporation) coated with biotin-BSA had surface areas from 74 to 84 cm$^2$/mg (provided on the certificate of analysis; Invitrogen Corporation). Based on these values, and the Pluronic® F108 hemacytometer studies above, it was calculated that a 0.4% (w/v) solution of Pluronic® F108 (or 4 mg/mL), containing 25 mg biotin-BSA microparticles per mL, would offer approximately 160 µg Pluronic® F108/mg microparticles. Since the 1.03 micron M1-070/40 microparticles (EMD Biosciences, Inc.) used in the Pluronic® F108 hemacytometer study had a surface area greater than 38.38 cm$^2$/mg, and were monodisperse at concentrations from 27.04 to 2027.7 µg Pluronic® F108/mg microparticles, a 0.4% (w/v) solution of Pluronic® F108, or 160 µg Pluronic® F108/mg microparticles, was used for initial dispersion studies to ensure sufficient quantity of Pluronic® F108 is present to promote biotin-BSA microparticle monodispersion.

Biotin-BSA-coated, SA-coated microparticles prepared by adding SA (25 to 50 µg SA/mg microparticles) to 25 mg/mL biotin-BSA microparticles dispersed in a PBS (20 mM sodium phosphate, 150 mM sodium chloride, pH 7.2) buffer containing 0.4% (w/v) Pluronic® F108 (Pluronic® F-108 NF Prill, BASF), or TBS (20 mM Tris, 150 mM sodium chloride, pH 7.2) buffer containing 0.4% (w/v) Pluronic® F108, were monodisperse after the addition of SA.

The microparticles remained monodisperse regardless of the order of addition of SA (i.e., biotin-BSA microparticles added drop-by-drop to SA, or SA added to biotin-BSA microparticles), as long as the biotin-BSA microparticles were dispersed in a solution containing 0.4% (w/v) Pluronic® F108 prior to their combination with SA. Unlike the use of sonication as stated above, the biotin-BSA-coated, SA-coated microparticles remained monodisperse if the biotin-BSA microparticles were dispersed in a buffer containing Pluronic® F108 prior to their combination with SA. Therefore, 0.4% (w/v) Pluronic® F108 successfully worked as a dispersion agent to promote biotin-BSA microparticle monodispersion both prior to, and after, biotin-BSA microparticle combination with SA by improving microparticle colloidal stability (decreased microparticle support surface hydrophobicity, increased microparticle support surface negative charge due to Pluronic® F108 pendant hydroxyl groups, and increased microparticle repulsion due to surface-to-surface negative charge repulsion), and by allowing the SA molecules to bind with all available (unbound and accessible) microparticle surface biotins before microparticle cross-linking could occur. Cross-linking can occur only if microparticle biotins are available, and if at least two of the four SA binding domains can bind with unbound and accessible biotins on two distinct microparticles.

It was empirically determined that Pluronic® F108 worked as a dispersion agent for microparticles coated with low input ratio biotinylated BSA at concentrations from 0.4% to 0.6% (w/v). Briefly, the combination of SA input ratio (10, 15, 25 and 35 µg SA/mg biotin-BSA microparticle), incubation times (30 and 60 minutes), and percent Pluronic® F108 (0.4 to 0.6% w/v) were evaluated to optimize the dispersion step. Results of assay performance testing (Access® Free T4 and Access® AccuTnI assays; Beckman Coulter, Inc.) and biotinylated IgG binding capacity testing indicated that the dispersion process is robust when 25 to 35 µg SA are added per mg biotin-BSA microparticles, at a microparticle concentration of 25 mg biotin-BSA microparticles/mL, in a TBS buffer (20 mM Tris, 150 mM sodium chloride, pH 7.2) containing 0.4% to 0.6% (w/v) Pluronic® F108, and incubated for 30 to 60 minutes.

Once the biotinylated microparticles were treated and dispersed in the 0.4% to 0.6% (w/v %) Pluronic® F108 solution, low levels or amounts of SA could be added to the biotinylated microparticles without the formation of microparticle aggregates or clumps. This process resulted in microparticle monodispersion after the coating of microparticles with SA. An illustration of the process is shown in FIG. 6, which shows SA treatment of coated microparticles in the absence of Pluronic® F108, and illustrates the monodispersion resulting from Pluronic® F108 treatment.

Example 4

Increased Signal-to-Noise Ratio Due to SA Non-Saturation and Orientation, Enhanced Surface Blocking, and Improved Binding Efficiency A comparison was made on two assay platforms between the signal-to-noise ratio of conventional microparticles and that of non-saturated microparticles of the invention which are characterized by SA non-saturation and orientation, enhanced surface blocking, and improved binding efficiency.

A binding surface directed against B-type natriuretic peptide or brain natriuretic peptide (BNP) was built on conventional microparticles (M1-070/40 microparticles, EMD Biosciences) by using a primary coating of GxBiotin (goat anti-biotin) antibody to the surface of a microparticle, followed by a secondary coating with a biotinylated OMNICLONAL® (Biosite, Inc.) Fab fragment directed against BNP. Briefly, the GxBiotin IgG primary coating was applied to the 10 mg/mL microparticles using carbodiimide chemistry by activating the microparticle surface carboxyl groups (70 to 100 mmols COOH/g) with approximately 6 to 10 mols EDC (1-ethyl-3-[3-dimethylaminopropyl]carbodiimide hydrochloride;

Pierce Biotechnology Inc./Thermo Scientific) and 6 to 10 mols sulfo-NHS (n-hydroxysulfosuccinimide; Pierce Biotechnology Inc./Thermo Scientific) per mol surface carboxyls in MES pH 5.5, incubating the microparticles with activation agents for 30 to 35 minutes, removing excess activation agents by washing the microparticles three times with MES pH 5.5, adding 40 micrograms of GxBiotin IgG per mg of activated microparticles, incubating the activated microparticles with GxBiotin IgG for 120 to 135 minutes, removing excess GxBiotin IgG and quenching residual activated carboxyl groups with a glycine-based buffer, stripping passively absorbed GxBiotin IgG using low (pH 2.5) and high (pH 8.0) pH buffers containing the surfactant TRITON® X-100 (polyethylene glycol p-(1,1,3,3-tetramethylbutyl)-phenyl ether), and blocking the microparticle surface with BSA.

The secondary coating was applied by washing the GxBiotin IgG primary coated microparticles into BNP assay-specific diluent, adding 10 micrograms of biotinylated BNP Fab per mg of GxBiotin microparticles, incubating the biotinylated BNP Fab with the microparticles for 90 to 135 minutes at room temperature, washing the microparticles to remove excess biotinylated BNP Fab, and diluting the BNP coated microparticles to 1.0 mg/mL with BNP assay-specific diluent.

Non-saturated microparticles in accordance with the invention were prepared by covalently attaching low input ratio biotinylated BSA to Dynal® AKT-100 tosyl-activated PMPs, where the BSA was biotinylated at a molar input ratio of 4 moles biotin to 1 mole BSA, followed by blocking the biotin-BSA microparticles with Pluronic® F108, dispersing the blocked biotin-BSA microparticles in Pluronic® F108, and finally coating the biotin-BSA microparticles with SA. The input ratio of biotinylated monoclonal antibody was the same for the conventional coated microparticles and the non-saturated microparticles. The biotinylated OMINCLONAL Fab was directed against BNP. The conventional coated microparticles and the non-saturated microparticles were evaluated at the same microparticle concentration (1.0 mg/mL), and were tested in identical Access® assay formats (Beckman Coulter, Inc.) with identical reagents, control samples, and patient samples. Results are shown in Table 5.

Signal-to-noise ratio was measured for the conventional and for the non-saturated microparticles on each of two assay platforms (Beckman Coulter, Inc.): the UniCel® Dxl 800 Access® Immunoassay System (relatively higher throughput system) and the Access® 2 Immunoassay System (relatively lower throughput system). Calibrator response was measured over a range of calibrator levels and for 13 separate patient samples. Results are shown for the conventional microparticles ("Control" in Table 5) and for the non-saturated microparticles ("Dev 3" in Table 5) in RLUs. Assay platform bias, expressed as "% Bias," was determined in the same manner for both control and non-saturated microparticles. The term "bias" refers to assay dose differences that can occur between any assay systems, including the Access® 2 Immunoassay System and the UniCel® Dxl 800 Access® Immunoassay System, due to hardware, design, and throughput differences (i.e., the Access® 2 Immunoassay System can complete 100 tests per hour, and the UniCel® Dxl 800 Access® Immunoassay System can complete 400 tests per hour), even though both platforms use identical reagents and supplies. Any bias may be attributed to differences in how each platform sonicates, mixes, washes, and incubates the microparticle reagent. Mean dose was calculated for the conventional microparticles and for the non-saturated microparticles.

As illustrated in Table 5, bias measurements for microparticles in accordance with the invention were better overall than for conventional microparticles. Table 5 also reveals that, for the non-saturated microparticles: (1) background was lower (compare S0 to S1-S5), (2) signal to background was more favorable over all calibrator levels and all patient samples, and, (3) sensitivity was higher for all calibrator levels and all patient samples. Thus, the non-saturated microparticles afforded an increase in assay signal (e.g., using the Dxl platform, $13 \times 10^6$ RLUs at S5 for conventional microparticles, compared with $23 \times 10^6$ RLUs at S5 for non-saturated microparticles of the invention), and a significant decrease in assay noise or background (e.g., using the Dxl platform, $10 \times 10^3$ RLUs at S0 for conventional microparticles, compared with $7 \times 10^3$ RLUs at S0 for non-saturated microparticles of the invention).

TABLE 5

INCREASED SIGNAL ASSAY DUE TO NON-SATURATED BIOTINYLATED ANTIBODY AND ORIENTATION ON A MICROPARTICLE BINDING SURFACE

| *SAMPLE PARAMETER | CONTROL | | | DEV 3 | | |
|---|---|---|---|---|---|---|
| | UNICEL® DXI | ACCESS® 2(A2) | % BIAS (DXI/A2) | UNICEL® DXI | ACCESS® 2 | % BIAS (DXI/A2) |
| MEAN CALIBRATOR RESPONSE (PICOGRAM/ML) | | | | | | |
| S0 = 0 | 10,778 | 10,166 | 106 | 7,554 | 6,535 | 116 |
| S1 = 29 | 63,634 | 46,350 | 137 | 143,801 | 106,980 | 134 |
| S2 = 113 | 268,760 | 186,100 | 144 | 665,839 | 493,437 | 135 |
| S3 = 525 | 1,310,426 | 953,801 | 137 | 3,195,942 | 2,538,410 | 126 |
| S4 = 2465 | 6,850,244 | 5,802,479 | 118 | 14,054,826 | 13,111,100 | 107 |
| S5 = 4841 | 13,366,055 | 12,411,410 | 108 | 23,141,201 | 23,554,060 | 98 |
| Mean Dose | | | | | | |
| QC 1 | 90.76 | 89.23 | 102 | 88.46 | 91.37 | 97 |
| QC 2 | 419.01 | 405.32 | 103 | 417.08 | 419.32 | 99 |
| QC 3 | 2,174.64 | 2,125.20 | 102 | 2,136.45 | 2,145,.01 | 100 |
| Patient 1 | 94.05 | 84.09 | 112 | 112.49 | 118.93 | 95 |
| Patient 2 | 72.46 | 62.89 | 115 | 90.44 | 94.43 | 96 |
| Patient 3 | 57.51 | 49.23 | 117 | 73.91 | 74.93 | 99 |

TABLE 5-continued

INCREASED SIGNAL ASSAY DUE TO NON-SATURATED BIOTINYLATED ANTIBODY AND ORIENTATION ON A MICROPARTICLE BINDING SURFACE

| | CONTROL | | | DEV 3 | | |
|---|---|---|---|---|---|---|
| *SAMPLE PARAMETER | UNICEL ® DXI | ACCESS ® 2(A2) | % BIAS (DXI/A2) | UNICEL ® DXI | ACCESS ® 2 | % BIAS (DXI/A2) |
| Patient 4 | 171.74 | 158.64 | 108 | 197.03 | 215.25 | 92 |
| Patient 5 | 417.49 | 369.84 | 113 | 589.08 | 578.74 | 102 |
| Patient 6 | 82.20 | 75.21 | 109 | 78.65 | 82.89 | 95 |
| Patient 7 | 131.27 | 119.80 | 110 | 168.63 | 171.98 | 98 |
| Patient 8 | 55.68 | 50.79 | 110 | 62.06 | 62.87 | 99 |
| Patient 9 | 66.79 | 61.65 | 108 | 91.96 | 91.62 | 100 |
| Patient 10 | 55.34 | 51.21 | 108 | 72.34 | 72.48 | 100 |
| Patient 11 | 51.59 | 45.63 | 113 | 53.19 | 53.15 | 100 |
| Patient 12 | 57.26 | 52.38 | 109 | 69.96 | 70.17 | 100 |
| Patient 13 | 105.51 | 93.47 | 113 | 143.18 | 142.86 | 100 |
| Average Dose | | | 110 | | | 98 |

*INST (N = 5 FOR EACH):

Another comparison of microparticles according to the invention and a commercially available binding microparticle was conducted (see Table 2 for a description of the microparticles). In this comparison, a commercially available Dynal® microparticle (Invitrogen Corporation), made by primary coating Dynal® AKT-100 tosylactivated PMPs with recombinant SA, was obtained. Performance of the commercially available SA-coated microparticle was compared with a microparticle according to the invention produced by coating Dynal® AKT-100 tosylactivated PMPs with low input ratio biotinylated BSA, blocking the biotin-BSA microparticles with Pluronic® F108, dispersing the blocked biotin-BSA microparticles in Pluronic® F108, and finally coating the biotin-BSA microparticles with SA. Both the commercially available microparticles and the non-saturated microparticles were used in a troponin I assay (Access® AccuTnI Assay; Beckman Coulter, Inc.) employing a biotinylated antibody against TnI as capture moiety. The commercially available microparticle and the non-saturated microparticle of the invention were both evaluated at the same microparticle concentration, and were tested in the identical assay format with identical reagents, control samples, and patient samples. Results are shown in Table 6.

TABLE 6

INCREASED ASSAY SIGNAL-TO-NOISE RATIO DUE TO SA NON-SATURATION AND ORIENTATION, AND SUBSEQUENT BIOTINYLATED ANTIBODY NON-SATURATION AND ORIENTATION ON A MICROPARTICLE SURFACE

| PARAMETER | DYNAL ® METHOD | BCI METHOD |
|---|---|---|
| CALIBRATOR RESPONSE (PICOGRAM/ML) | | |
| S0 = 0 | 13,023 | 8,116 |
| S1 = 29 | 49,030 | 54,986 |
| S2 = 113 | 149,472 | 194,922 |
| S3 = 525 | 587,250 | 779,833 |
| S4 = 2465 | 2,870,740 | 3,829,280 |
| S5 = 4841 | 9,611,635 | 12,422,050 |
| % CV CALIBRATOR RESPONSE | | |
| S0 = 0 | 1.9 | 4.3 |
| % CV CALIBRATOR DOSE | | |
| S1 = 29 | 1.0 | 1.8 |
| S2 = 113 | 1.8 | 0.7 |
| S3 = 525 | 3.6 | 0.4 |

TABLE 6-continued

INCREASED ASSAY SIGNAL-TO-NOISE RATIO DUE TO SA NON-SATURATION AND ORIENTATION, AND SUBSEQUENT BIOTINYLATED ANTIBODY NON-SATURATION AND ORIENTATION ON A MICROPARTICLE SURFACE

| PARAMETER | DYNAL ® METHOD | BCI METHOD |
|---|---|---|
| S4 = 2465 | 3.2 | 1.0 |
| S5 = 4841 | 4.6 | 1.7 |
| RATIOS | | |
| S1/S0 | 3.8 | 6.8 |
| S5/S0 | 738 | 1531 |

The non-saturated microparticles of the invention resulted in a significant increase in assay signal compared to the commercially available microparticles (e.g., S5 increased from $9.6 \times 10^6$ RLUs to $12.4 \times 10^6$ RLUs), and a significant decrease in assay noise or background (e.g., S0 decreased from $13 \times 10^3$ RLUs to $8 \times 10^3$ RLUs). Thus, the non-saturated microparticles of the invention displayed an increased assay signal-to-noise ratio due to the non-saturated nature and orientation of SA on the microparticle binding surface and its cumulative non-saturating and orientating effect on the subsequently added biotinylated antibody. Note, the above Dynal® Method and BCI Method comparisons used the optimized (commercialized product, Dynal® DYNABEADS MyOne Streptavidin T1; Invitrogen Corporation) Dynal® Method, but not the optimized BCI Method. Subsequent TnI testing (Access® AccuTnI Assay) of the non-saturated microparticles using the optimized BCI Method resulted in an even more significant increase in assay signal (i.e., S1=80,000 RLUs, S5=18,300,000 RLUs), similar assay noise or background (i.e., S0=8,500 RLUs), and increased curve ratios (i.e., S1/S0=9.4, S5/S0=2,130).

Example 5

Reduction in Non-Specific Binding

Studies were conducted that revealed reductions in non-specific binding using microparticles made in accordance with the invention, since nonspecific binding is an undesirable phenomenon in many assay formats. Nonspecific binding describes artifactual binding events in an immunoassay involving its components and/or support surfaces that yield undesirable byproducts which can adversely affect assay performance parameters including, as a non-limiting example, signal-to-noise ratio. Nonspecific binding may involve binding to the solid phase support surface itself, and/or to the ligand::support coupler complex coated on the support surface. The specific embodiment of a microparticle employing BSA as a support coupler was examined.

BSA is an albumin (bovine serum albumin), and albumins can bind thyroid hormones. BSA has been identified as a binding protein for the thyroid hormones T3 and T4. If a solid phase support surface is coated with BSA, the binding surface will capture or bind such thyroid hormones unless it is successfully blocked.

Since non-saturated SA microparticles are produced by coating microparticles with biotinylated BSA, blocking the surface with Pluronic® F108, and coating the biotin-BSA surface with SA, the non-saturated SA microparticles have the potential to bind thyroid hormones such as T3 and T4 unless their surface is sufficiently blocked. In particular, if non-saturated SA microparticles are incubated with T3 alkaline phosphatase conjugate, the microparticles may bind T3-conjugate and generate non-specific binding (NSB) signal in an assay unless the surface is blocked and nonspecific binding is mitigated or eliminated. In addition to increased background, elevated calibrator signal can result from non-specific binding of T3 conjugate. It was empirically determined that Pluronic® F108 blocked microparticles coated with low input ratio biotinylated BSA at concentrations from 0.4% to 0.6% (w/v).

Initial blocking studies evaluated 0.1% (w/v) BSA in 0.1M Tris pH 8.0, and 0.4% (w/v) Pluronic® F108 in 0.1M Tris pH 8.0, as blocking agents for tosylactivated paramagnetic microparticles coated with biotinylated BSA. Biotin-BSA microparticles were incubated with the 0.1% (w/v) BSA or 0.4% (w/v) Pluronic® F108 blocking buffers for 18 hours at 37° C., and coated with SA by slowly titrating the biotin-BSA microparticles into a molar excess of SA. The biotin-BSA microparticles were washed three times prior to blocking, and also after blocking, using one of the following buffers: PBS pH 7.4, PBS with 0.1% (w/v) TRITON X-100 pH 7.4, PBS with 0.4% (w/v) Pluronic® F108 pH 7.4, TBS pH 7.4, TBS with 0.1% (w/v) TRITON x-100 pH 7.4, or TBS with 0.4% (w/v) Pluronic® F108. Results of assay performance testing (Access® AccuTnI Assay; Beckman Coulter, Inc.) indicated that the 0.4% (w/v) Pluronic® F108 blocking buffer, and TBS pH 7.4 washes, S1 and S5 RLUs), greatest assay dynamic range, and highest signal-to-noise ratio.

Subsequent blocking optimization studies evaluated the performance of biotin-BSA microparticles prepared with BSA biotinylated with sulfo-NHS-LC-biotin, sulfo-HHS-LC-LC-biotin, or PFP biotin, washed three times with TBS pH 7.4, blocked with 0.1% (w/v) BSA or 0.4% (w/v) Pluronic® F108 blocking buffers for 4 hours at 37° C. or 18 hours at 37° C., washed three times with TBS pH 7.4, and coated with SA or neutravidin by slowly titrating the biotin-BSA microparticles into a molar excess of SA or neutravidin. Results of assay performance testing (Access® AccuTnI Assay; Beckman Coulter, Inc.) indicated that sulfo-NHS-LC-biotin BSA microparticles, and PFP-biotin BSA microparticles, blocked with 0.4% (w/v) Pluronic® F108 for 4 hours at 37° C., and coated with SA or neutravidin, resulted in the lowest background signal (S0), highest calibrator signal (S1 and S5), greatest assay dynamic range, and highest signal-to-noise ratio.

Final Pluronic® F108 blocking optimization studies used biotin-BSA microparticles prepared by coating low input ratio sulfo-NHS-LC-biotin conjugated BSA (40 micrograms biotin-BSA per mg microparticles) onto Dynal® MyOne tosylactivated microparticles (Dynal® DYNABEADS MyOne Tosylactivated, 1.0 micron diameter, Invitrogen Corporation) at 40° C. for 18 hours in 0.1M Borate pH 9.5. The biotin-BSA microparticles were washed three times with TBS pH 7.4, blocked with 0.2%, 0.4%, 0.6%, or 0.8% (w/v) Pluronic® F108 in TBS pH 7.4 for 2, 4, or 24 hours at 40° C., washed three times with TBS pH 7.4, and coated with SA by dispersing the biotin-BSA microparticles in TBS with 0.4% (w/v) Pluronic® F108 pH 7.4 and then adding 35 micrograms of SA per mg microparticles. Results of assay performance testing (Access® Free T4 and Access® AccuTnI assays; Beckman Coulter, Inc.), and biotinylated IgG binding capacity testing, indicated that the microparticles blocked for 4 hours with 0.4% to 0.6% (w/v) Pluronic® F108 resulted in the lowest background signal, highest calibrator signal, greatest assay dynamic range, highest signal-to-noise ratio, and reproducible biotinylated IgG binding capacity.

To assess the nonspecific binding of non-saturated SA-coated microparticles, a lot of non-saturated SA-coated microparticles was incubated at 4° C. or 37° C. for 3 days, and tested in a free T4 immunoassay using Access® Free T4 calibrator and Access® Free T4 Reagent Packs (Beckman Coulter, Inc.). The samples tested without biotinylated Free T4-specific antibody ("No AB") would assess the nonspecific binding of T3-conjugate to the microparticle surface. Results are shown in Table 7 for inventive microparticles having biotinylated BSA coated with SA, compared with signal generated from a commercially available microparticle assay (Access® Free T4) employing ovalbumin and a biotinylated antibody, and the Dynal® DYNABEADS M-280 Streptavidin microparticles from Invitrogen Corporation (2.8 micron microparticles).

TABLE 7

DECREASED OR MINIMIZED NONSPECIFIC BINDING OF A T3 ALKALINE PHOSPHATASE CONJUGATE TO A BIOTIN-BSA-SA SURFACE BLOCKED WITH Pluronic ® F108

| PARAMETER CALIBRATOR RESPONSE | COMMER-CIAL PACK | INVENTIVE MICROPARTICLES | | | |
|---|---|---|---|---|---|
| | | 4° C. | | 37° C. | |
| | | AB | NO AB | AB | NO AB |
| S0 | 1,480,850 | 1,516,620 | 7,704 | 1,566,340 | 8,477 |
| | 1,575,600 | 1,524,310 | 7,761 | 1,611,180 | 8,353 |
| | 1,551,460 | 1,488,090 | 7,601 | 1,567,280 | 8,132 |
| | 1,546,320 | 1,495,310 | 7,741 | 1,634,690 | 8,184 |
| Mean | 1,538,558 | 1,506,083 | 7,702 | 1,594,873 | 8,287 |

Mean % difference with Ab = 105.9%, without Ab = 107.6%
Access ® Instrument; Access ® Free T4 Reagent Pack Results indicate that conjugate nonspecific binding did not occur since the S0 assay signal was <8,500 RLUs in both the 4° C. and 37° C. non-saturated samples when biotinylated Free T4-specific antibody was removed from the reagent packs (No Ab). Assay signal should only be generated if nonspecific binding occurs, or if biotinylated Free T4-specific antibody is present in the assay since the SA surface will capture the biotinylated Free T4-specific antibody, and this captured Free T4-specific antibody did bind the T3-conjugate (i.e., S0>$1.5\times10^6$ RLUs). The commercially available microparticles employed SA microparticles with ovalbumin (not BSA), in order to reduce nonspecific binding. Even though the non-saturated microparticles employed low input ratio biotinylated BSA, they performed better. Overall, the results indicate that even at elevated temperature for an extended period (37° C. for 3 days), nonspecific binding was not observed, suggesting that Pluronic® F108 is not displaced from the non-saturated microparticles under these conditions. Accordingly, a biotin-BSA-coated, SA-coated binding surface blocked with Pluronic® F108 results in decreased or minimized nonspecific binding of a T3 alkaline phosphate conjugate, even over time at elevated temperature.

Example 6

Coating Process Reproducibility

Process validation for SA coating was carried out for non-saturated and orientated microparticles according to the invention. Results are shown in Table 8 and in FIG. 12 and FIG. 13. The microparticles for process validation were prepared in accordance with the invention. Briefly, Dynal® AKT-100 tosylactivated PMPs (Invitrogen Corporation) were coated with low input ratio biotinylated BSA, the biotin-BSA microparticles were blocked with Pluronic® F108, the blocked biotin-BSA microparticles were dispersed in Pluronic® F108, and the biotin-BSA microparticles were coated with SA.

Assays were conducted with various combinations of independently prepared SA coatings ("Process"), microparticle lots ("Tosylactivated PMP Lot"), low input ratio biotinylated BSA lots ("Low Input Ratio Biotinylated BSA Lot"), Pluronic® F108 lots (Block Copolymer Pluronic® F108 Lot"), and SA lots ("SA Lot"). In Table 8, the term "Process" refers to the coating of microparticles with low input ratio biotinylated BSA, blocking the microparticles with Pluronic® F108, dispersing the microparticles in Pluronic® F108, and coating SA on the biotin-BSA microparticles; "Operator" indicates that the SA coatings, or "Process", were performed by one of four different human operators.

TABLE 8

PROCESS REPRODUCIBILITY FOR MAKING MICROPARTICLES IN ACCORDANCE WITH THE INVENTION

| VALIDATION LOT | OPERATOR | SCALE (MG) | TOSYL-ACTIVATED PMP[1] LOT | LOW INPUT RATIO BIOTINYLATED BSA LOT | Pluronic ® F108 LOT | SA LOT |
|---|---|---|---|---|---|---|
| 1[2] | 1 | 10,000 | 1 | 1 | 1 | 1 |
| 2[3] | 1 | 50 | 1 | 1 | 1 | 1 |
| 3[3] | 1 | 50 | 1 | 1 | 1 | 1 |
| 4[3] | 1 | 250 | 1 | 1 | 1 | 1 |
| 5[2] | 2 | 10,000 | 1 | 1 | 1 | 1 |
| 6[4] | 1 | 2,500 | 1 | 1 | 2 | 1 |
| 7[4] | 1 | 2,500 | 1&2 (pool) | 1&2 (pool) | 2 | 1&2 (pool) |
| 8/Pilot 1[5] | 3 | 40,000 | 2 | 2 | 1 | 3 |
| 9/Pilot 2[5] | 3 | 40,000 | 3 | 3 | 1&2 (pool) | 3 |
| 10[3] | 1 | 50 | 1 | 1 | 1 | 1 |
| 11[4] | 4 | 250 | 1 | 2 | 1 | 3 |
| 12[4] | 4 | 250 | 1 | 3 | 1&2 (pool) | 3 |

Superscript 1: PMP denotes "paramagnetic microparticle"
Superscript 2 denotes one semi-automated synthesis of microparticles
Superscript 3 denotes manual synthesis of microparticles
Superscript 4 denotes a second semi-automated synthesis of microparticles
Superscript 5 denotes a third semi-automated synthesis of microparticles
Whether manual or semi-automatic, microparticles were prepared according to the steps of FIG. 1A and 1B.

Results of further validation studies employing a Free T4 assay (see FIG. 12) for 11 validation lots using five separate commercially available controls ("Bio-Rad Liquid 1," "Bio-Rad Liquid 2," "Bio-Rad 1," "Bio-Rad 2," and "Bio-Rad 3"; Bio-Rad Laboratories, Inc.) and two samples of pooled patients' sera ("Patient Pool 1" and "Patient Pool 2") and three individual samples ("Sample 1," "Sample 2," and "Sample 3") revealed good agreement, with a CV less than or equal to about 5%. In contrast, the conventionally prepared microparticles (for example, DYNABEADS M-280 SA microparticles) have a CV of at least around 10%.

Further validation studies (see FIG. 13) for 10 validation lots employing a BPH-A marker, using three sets of controls where antigen was spiked into serum (Control A, B, and C), and three patient serum controls (QC Patient 1, 2, and 3) resulted in similar findings.

Results of the SA coating process validation reveal that all validation specifications were met for all lots. Furthermore, the results indicate that the process of making microparticles in accordance with the invention is associated with a low degree of variance, is reproducible, and is reliable.

Example 7

Enhanced Stability of Non-Saturated Microparticles

Accelerated stability testing, as measured by recovery of T4 in a calibrator or sample, was conducted on multiple validation lots of non-saturated SA-coated microparticles bearing a biotinylated anti-T4 antibody using Access® Free T4 Calibrator in an Access® Free T4 assay (Beckman Coulter, Inc.) at 4° C. and at 37° C. for a period of four days, and at 4° C. and at 37° C. for a period of 127 days. Results are shown in Table 9 and FIGS. 14A and 14B.

TABLE 9

ACCELERATED STABILITY STUDIES OF MULTIPLE VALIDATION LOTS
4 DAYS AT 37° C.

| VALIDATION LOT | SCALE (mg) | *PROCESS | AVG FREE T4 CALIBRATOR RECOVERY (%) | AVG FREE T4 CONTROL DOSE RECOVERY (%) | AVG FREE T4 PATIENT DOSE RECOVERY (%) |
|---|---|---|---|---|---|
| 1 | 10,000 | Semi-Auto 2 | 102.1 | 100.5 | 102.9 |
| 2 | 50 | Manual | 99.1 | 100.5 | 100.7 |
| 3 | 50 | Manual | 104.1 | 100.5 | 102.6 |
| 4 | 250 | Manual | 101.9 | 100.6 | 97.3 |
| 5 | 10,000 | Semi-Auto 2 | 102.0 | 100.5 | 99.3 |
| 6 | 2,500 | Semi-Auto 1 | 106.2 | 97.2 | 99.3 |
| 7 | 2,500 | Semi-Auto 1 | 113.5 | 101.1 | 97.9 |
| 8/Pilot 1 | 40,000 | Semi-Auto 3 | 100.9 | 97.9 | 100.8 |
| 9/Pilot 2 | 40,000 | Semi-Auto 3 | 101.7 | 100.6 | 102.0 |
| 11 | 250 | Semi-Auto 1 | 103.2 | 99.2 | 101.3 |
| 12 | 250 | Semi-Auto 1 | 102.6 | 99.0 | 100.5 |

*Process refers to manually prepared microparticles, or microparticles prepared by three semi-automatic processes. Whether manual or semi-automatic, microparticles were prepared according to the steps of FIG. 1A and 1B.

Table 9 shows average calibrator, control dose, and patient dose recoveries for validation lots of non-saturated SA-coated microparticles incubated for 4 days at 37° C. as compared to 4 days at 4° C. As can be seen from Table 9, average recovery for all lots was at or near 100%.

In FIGS. 14A and 14B, recovery is expressed as percent of RLUs measured by assaying for FT4 after 127 days at 37° C. as compared to RLUs measured by assaying for FT4 after 127 days at 4° C. ("Recovery"). Calibrator levels were S0=0.0 ng/mL, S1=0.54 ng/mL, S2=1.01 ng/mL, S3=1.98 ng/mL, S4=3.00 ng/mL, and S5=6.11 ng/mL. Apart from calibrator, other samples assayed included Bio-Rad control 1=0.64 ng/mL, Bio-Rad control 2=2.18 ng/mL, and Bio-Rad control 3=4.19 ng/mL ("Bio-Rad lypho"), and five separate patient samples ("Patient #") with doses Patient 1=1.02 ng/mL, Patient 2=1.12 ng/mL, Patient 3=1.83 ng/mL, Patient 4=2.74 ng/mL, and Patient 5=3.80 ng/mL. Overall, recovery was at or near 100%, indicating that treatment for an extended period of time at elevated temperature does not adversely affect the performance of the non-saturated microparticles. For comparison purposes, specifications for a free T4 assay employing commercially available SA-coated microparticles (Access® Free T4 assay; Beckman Coulter, Inc.) are included in FIGS. 14A and 14B ("Current FT4 Assay Specifications"). The non-saturated microparticles fell within the specifications of the commercially available free T4 assay.

Overall, the accelerated stability testing confirmed that independently produced SA-coated microparticle lots are very stable. No significant difference was observed between validation lots incubated for 3 days at 4° C. or 3 days at 37° C. Calibrator signal was very similar (calibrator recovery from 99.1% to 113.5%), and the average Control and Patient dose recoveries were all from 97.2% to 102.9%.

No significant difference in performance was observed when a single lot was incubated for 127 days at 4° C. or 37° C. Calibrator signal was very similar (calibrator recovery from 95.1% to 109.6%), curve ratios were very similar (% Recovery from 91.3% to 105.1%), and the average Control and Patient dose recoveries were all from 93.7% to 107.6%.

Example 8

Sloughing Analysis of Non-Saturated Microparticles

Figure 15A:
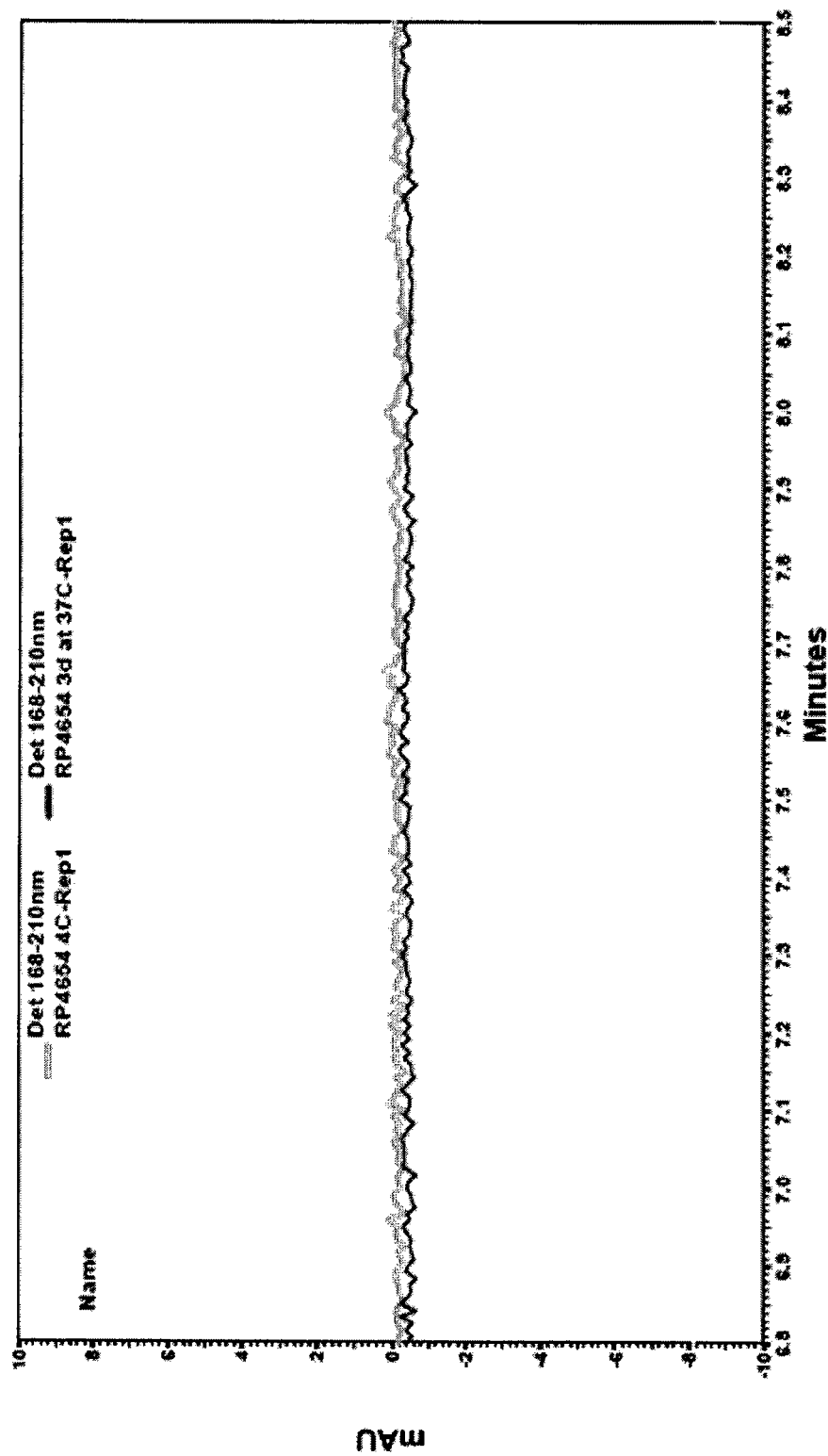
FIG. 15A illustrates the results of sloughing analysis.
Figure 15B:
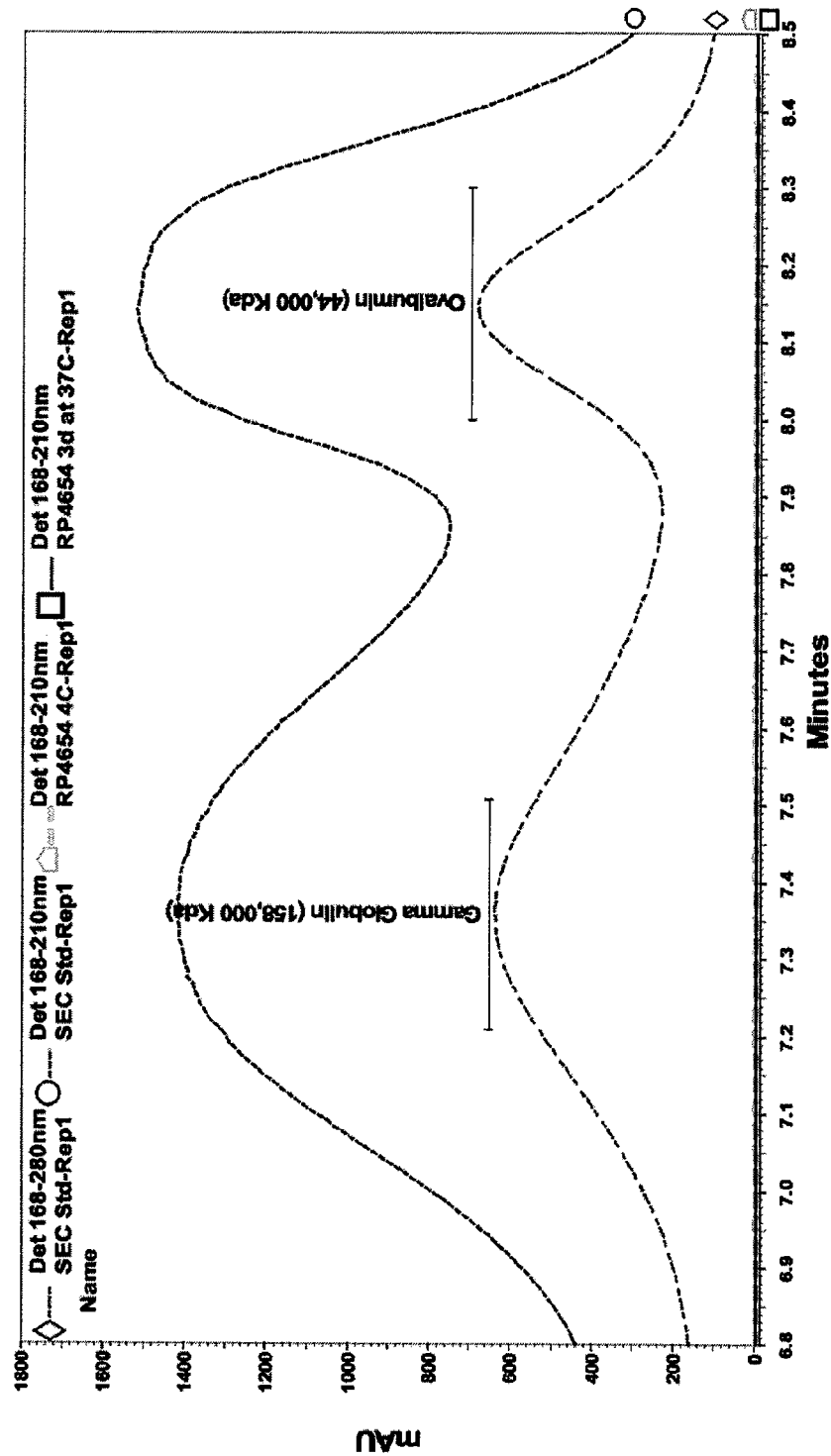
FIG. 15B is further illustration of the results of sloughing analysis.
Figure 17:
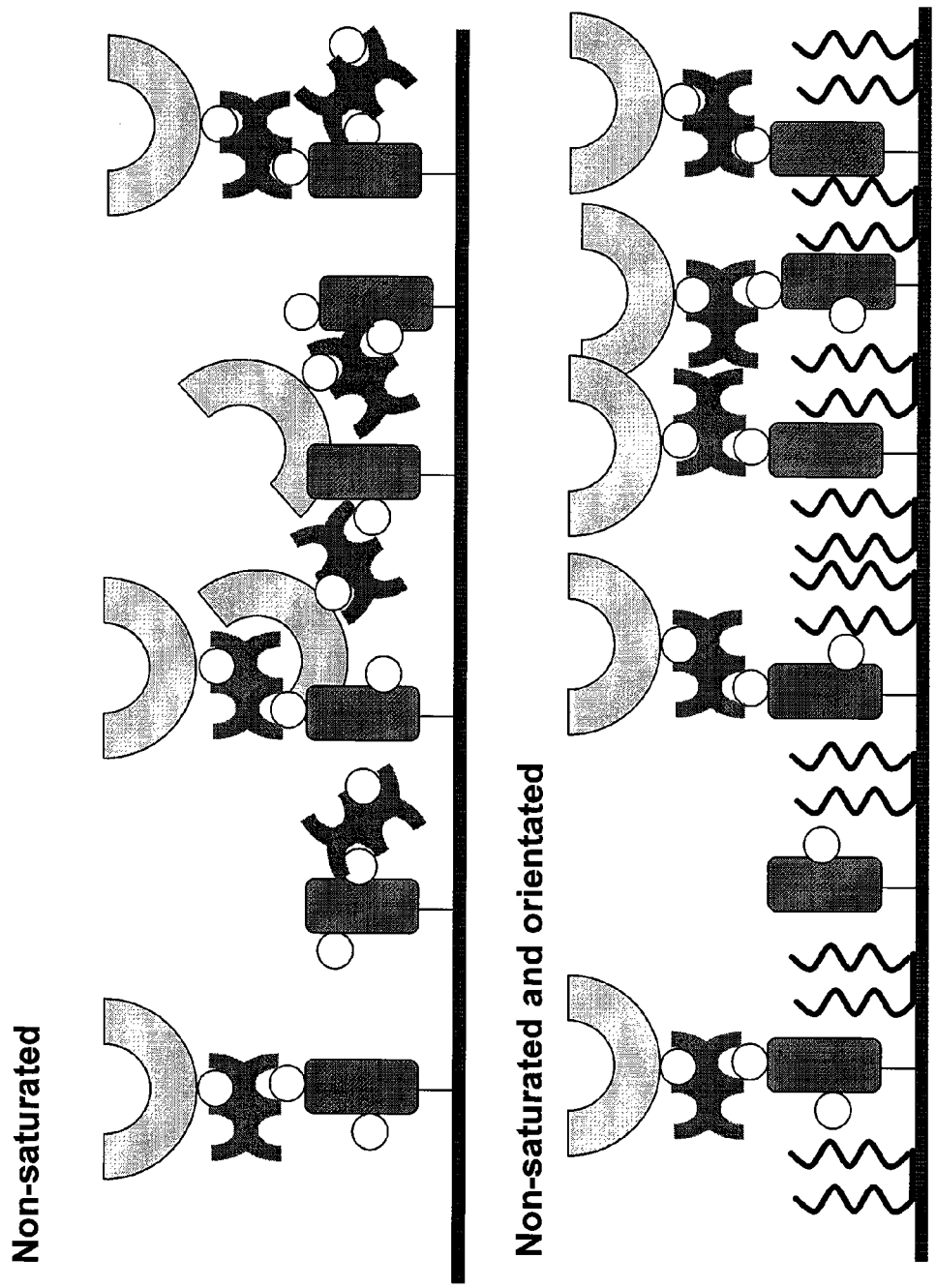
FIG. 17 is a schematic illustrating the difference between a non-saturated binding surface of the invention and a non-saturated and orientated binding surface of the invention.

A sloughing study of non-saturated microparticles made in accordance with the invention was carried out. There are approximately 8.7-14.0 µg biotin-BSA/mg PMP, and 5.6-7.8 µg SA/mg PMP in microparticles made in accordance with the invention that employ biotin-BSA and are coated with SA (see Example 11). If 1% of the protein were to slough from 10 mg total PMP, there would be approximately 0.7-1.0 µg of protein in solution. An analysis of sloughing was conducted for such SA-coated microparticles. Results of size exclusion chromatography on an HPLC (SEC-HPLC) indicate no detectable SA or BSA at 210 nm, or less than 1% slough. If SA and/or biotin-BSA are free in solution they are below the limit of detection of the SEC-HPLC method (see FIGS. 15A and 15B). In FIG. 15B, the Gamma Globulin and Ovalbumin SEC standard peaks (peak heights ~1,400 mAU) represent 83.5 µg total protein at 210 nm. A peak height of 5 mAU (milli-absorption units) would represent 0.3 µg of protein. Size exclusion HPLC analysis at 210 nm indicated that there is no detectable biotin-BSA or SA molecules in solution after stressing the microparticles for 3 days at 37° C. (e.g., no protein slough from the microparticle surface). Accordingly, sloughing does not present a problem with microparticles made according to the invention. Stability data presented above supports the results of the SEC-HPLC SA slough analysis, since assay signal, and presumably biotinylated IgG binding, were not affected by stressing the microparticles up to 127 days at 37° C. (FIGS. 14A-B).

Example 9

Low Input Ratio Biotinylation of Ovalbumin

Microparticles according to the invention were made with ovalbumin coupled with biotin instead of BSA coupled with biotin. Ovalbumin was biotinylated with sulfo-NHS-LC-biotin (sulfosuccinimidyl-6-[biotinamido]hexanoate, Pierce Biotechnology Inc./Thermo Scientific) at various molar input ratios of biotin to ovalbumin (see Table 10), as described for BSA in Example 1. Briefly, four separate biotinylation lots for biotinylating ovalbumin (20 mg in 1.253 mL) in borate buffer, pH 8.2 and DMF with sulfo-NHS-LC-biotin at various input ratios were prepared as shown in Table 10.

TABLE 10

BIOTINYLATION OF OVALBUMIN AT LOW INPUT RATIOS

| LOT | INPUT RATIO | OVALBUMIN (MG/ML) | (MG) | (ML) | (NMOL) | BIOTIN (NMOL) | (MG) | (µL) |
|---|---|---|---|---|---|---|---|---|
| 1 | 2 | 15.96 | 20 | 1.253 | 444 | 889 | 0.495 | 16.5 |
| 2 | 4 | 15.96 | 20 | 1.253 | 444 | 1778 | 0.989 | 33.0 |
| 3 | 6 | 15.96 | 20 | 1.253 | 444 | 2667 | 1.484 | 49.5 |
| 4 | 8 | 15.96 | 20 | 1.253 | 444 | 3556 | 1.979 | 66.0 |

Percent yield on biotinylation was 75.6% for input ratio of 2; 83.3% for input ratio of 4; 85.1% for input ratio of 6; and 79.1% for input ratio of 8. HABA (4'-hydroxyazobenzene-2-carboxylic acid) analysis was done for each input ratio. Results are shown in Table 11.

TABLE 11

RESULTS OF OVALBUMIN LOW INPUT RATIO BIOTINYLATION

| LOT | INPUT RATIO | *MEAN $OD_{500}$ | SD | % CV | CORRECTED OD | µM BIOTIN | µM PROTEIN | BIOT-PROT RATIO | % STABILITY |
|---|---|---|---|---|---|---|---|---|---|
| 1 | 2 | 0.8992 | 0.012 | 1.3 | 0.2768 | 163 | 141.0 | 1.2 | 97.3 |
| 2 | 4 | 0.6352 | 0.003 | 0.4 | 0.5407 | 318 | 141.0 | 2.2 | 95.3 |
| 3 | 6 | 0.5568 | 0.036 | 6.5 | 0.6191 | 364 | 118.2 | 3.1 | 86.5 |
| 3 | 6 | 0.8500 | 0.007 | 0.8 | 0.3260 | 384 | 118.2 | 3.2 | |
| 4 | 8 | 0.4457 | 0.006 | 1.4 | 0.7302 | 430 | 109.9 | 3.9 | 81.8 |
| 4 | 8 | 0.7417 | 0.006 | 0.9 | 0.4343 | 511 | 109.9 | 4.7 | |

Stability analysis of 4 independent biotinylation lots of biotinylated ovalbumin was completed by coating 25 mg/mL tosylactivated PMPs (Dynal® DYNABEADS MyOne Tosylactivated, 1.0 micron diameter, Invitrogen Corporation) with ovalbumin-biotin for 18-24 hours at 37° C. in 0.1 M borate buffer pH 9.5 (0.050 mg ovalbumin-biotin per mg PMP), washing the microparticles three times with TBS pH 7.4, blocking the ovalbumin-biotin coated microparticle surface with 0.4% (w/v) Pluronic® F108 in TBS pH 7.4 for 4 hours at 37° C., washing the microparticles three times with TBS pH 7.4, dispersing the ovalbumin-biotin microparticles in 0.4% (w/v) Pluronic® F108 in TBS pH 7.4, coating the ovalbumin-biotin microparticles with SA in TBS pH 7.4 for 30 minutes at room temperature (0.035 mg SA per mg ovalbumin-biotin PMP), washing the microparticles three times with TBS pH 7.4 with sodium azide (0.1% w/v), washing the microparticles three times with Access® Free T4 assay-specific microparticle buffer, diluting the microparticles from 25 mg/mL to 0.35 mg/mL with Access® Free T4 assay-specific microparticle buffer, incubating the ovalbumin-biotin-SA-coated microparticles at 4° C. or 37° C. for 3 days, and testing the ability of the ovalbumin-biotin-SA microparticles to bind biotinylated anti-Free T4 antibody in the Access® Free T4 Assay (Beckman Coulter, Inc.). Stability was determined by calculating the average of the individual free T4 calibrator RLU recoveries. The Access® Free T4 Assay uses six different calibrators (S0, S1, S2, S3, S4, and S5) with antigen levels from 0 ng/mL to 6 ng/mL (see Table 4). Recovery was calculated by dividing the 37° C. calibrator RLU response by the 4° C. calibrator RLU response, and multiplying the result by 100%. Stability was calculated by averaging the recovery for all six calibrators. Results are shown in Table 11.

Stability was indicative of the change in SA binding capacity after incubating the solid phase at 4° C. or 37° C. for 3 days. A decrease in stability is due to sloughing or dissociation of passively bound biotin or biotin reagent from ovalbumin-biotin conjugates, and the subsequent capture of the free biotin or biotin reagent by SA over time.

Table 11 establishes that proteins other than BSA, such as ovalbumin, can be effectively prepared using low input ratio biotinylation as described herein. Results of ovalbumin-biotin stability testing are very similar to the biotin-BSA stability results described earlier (see Table 1). Results indicated that ovalbumin-biotin prepared at high molar input ratios (i.e., 8:1) displays decreased stability. As the molar input ratio of biotin reagent to ovalbumin is decreased from 8:1 to 2:1, stability improved from 82% to 97% (see Table 11).

Example 10

Density of Biotin, SA, and Immunoglobulins on the Surface of Microparticles for Affinity Assays PMP according to the invention were made using BSA as a support coupler and biotin as a ligand. SA was used to bind a biotinylated IgG as capture moiety.

Briefly, Dynal® PMPs (Invitrogen Corporation) were made in accordance with the procedure of Example 1 (i.e., PMPs were coated with low input ratio biotin-BSA prepared according to the protocol of Example 1. Microparticles were prepared in accordance with the invention and coated with low input ratio biotin-BSA and then SA in accordance with the invention. Thereafter, the SA-coated PMPs were treated with biotinylated IgGs. The following IgGs were used: biotinylated M06 IgG, which is the McxAccess® AccuTnI monoclonal antibody used as the detector antibody (i.e., it is conjugated to alkaline phosphatase) in the Access® AccuTnI Assay (Beckman Coulter, Inc.), and biotinylated 399.4 IgG, which is the McxFPSA monoclonal antibody used as the capture antibody (i.e., it is coated onto a goat anti-biotin PMP) in the Access® Free PSA Assay (Beckman Coulter, Inc.). Various lots of the SA PMPs prepared in accordance with this invention, were coated with M06 IgG or 399.4 IgG to assess the biotinylated IgG binding capacity of the SA PMP lots using the $^{125}$I-labelled biotinylated IgG method as described earlier. A description of the microparticles and the results in terms of surface density of components of the surface are presented in Table 12.

TABLE 12

SURFACE AREA CALCULATIONS: MICROPARTICLES ACCORDING TO THE INVENTION

| LOT | §PMP DIAMETER (μm) | SURFACE AREA (M²/G) | COATING DENSITY (μG BIOTIN-BSA/MG PMP) | SA DENSITY (μG SA/MG PMP) | IGG DENSITY (μG BIOTIN-M06 IGG/MG PMP) | IGG DENSITY (μG BIOTIN-399.4 IGG/MG PMP) |
|---|---|---|---|---|---|---|
| A | 1.10 | 7.7 | 8.7 | 7.8 | 3.8-4.5 | 6.1 |
| B | 1.05 | 8.4 | nd* | nd | nd | nd |
| C | 1.07 | 7.4 | 14.0 | nd | 4.5 | 3.4 |

§PMP diameter is an estimate; populations of PMPs are to a certain extent polydisperse with respect to diameter.
*nd = not determined The data of Table 12 can be converted to molar values, which conversion reveals that there are about $2.46 \times 10^{-4}$ (μmol biotin)/(mg PMP) in the example shown (see A). For a microparticle of about a micron in diameter, with surface area of $7.7 \times 10^{-3}$ m²/(mg of PMP), there are about $3.19 \times 10^{-2}$ (μmol biotin)/(m² PMP).

In addition to the lots described above, biotinylated PMPs were made in accordance with the invention and found to have a density of 15.1 (μg biotin-BSA)/(mg PMP), for a 1.10 micron PMP having a surface area of 7.7 m²/g.

In addition to the lots described above, three further validation lots were prepared in the same manner. These further lots are described in Table 13.

TABLE 13

SURFACE AREA CALCULATIONS FOR VALIDATION LOTS OF MICROPARTICLES ACCORDING TO THE INVENTION

| LOT | §PMP DIAMETER (μM) | SURFACE AREA (M²/G) | SA DENSITY (μG SA/MG PMP) | MOLAR RATIO OF BIOTIN TO BSA VIA HABA ANALYSIS (MOLS BIOTIN/MOLES BSA) |
|---|---|---|---|---|
| D | 1.10 | 7.7 | 6.1 | 1.85 |
| E | 1.05 | 8.4 | 6.6 | 1.96 |
| F | 1.07 | 7.4 | 5.6 | 1.75 |

§PMP diameter is an estimate; populations of PMPs are to a certain extent polydisperse with respect to diameter.

Viewing the data of Table 13 in molar terms, given that there are about 6.1 (μg SA)/(mg PMP), and using a molecular weight of 56 kDa for SA, there are about $1.41 \times 10^{-2}$ (μmol SA)/(m² PMP). Thus, in comparison with the data in Table 12, there appears to be about half as much SA on the microparticle as biotin.

Example 11

Surface density calculations for BSA, biotin, SA, and IgG, for lots prepared in the Examples described above, were carried out. Low-input biotinylation lots of Table I that indicated good stability (13 lots) were used to generate surface density for microparticles. Actual surface density calculations for microparticles, and for non-particulate supports (based on microparticle data) are shown in FIGS. 16A and 16B and below in Table 14. Surface density calculations for microparticles, assuming a smooth surface, and for non-particulate supports (based on "smooth" microparticle data) are shown in FIGS. 16A, 16C, 16D, and in Table 15 below.

Surface density calculations were based on physical testing parameters. Briefly, the amount of BSA and SA coated on the surface during the coating steps was measured by supernatant fluid analysis following the coating steps, using the BCA method of protein concentration determination (BCA Protein Assay [bicinchoninic acid]; Pierce Biotechnology Inc./ Thermo Scientific) and/or absorbance at 280 nm (for BSA and SA). HABA analysis was used to quantitate the amount of biotin on BSA. $^{125}$I binding was used to assess the binding capacity of biotin-IgG. Briefly, microparticles in TBS were offered a known amount of BSA, incubated, and the microparticles were separated from supernatant fluid. Protein remaining in the supernatant fluid was measured, and subtracted from the amount of protein added. The microparticles were washed and the washes analyzed for protein content. TRIS-buffered saline, pH 7.4 was used for coupling as well as for binding of antibody to the microparticles. Calculations were done based on (a) actual measured surface area provided by the microparticle manufacturer and (b) calculated surface area based on microparticle diameter and an assumption of smoothness.

For the surface density measurements shown in Table 14, microparticle surface area (based on a calculation using dry solid weight) ranged from a minimum of 7.4 m²/g to a maximum of 8.4 m²/g, with a midrange of 7.7 m²/g.

TABLE 14

SURFACE DENSITY: NO SMOOTHNESS ASSUMPTION

| SUMMARY | BSA: 8.7-14.0 μG/MG SA: 5.6-7.8 μG/MG HABA: 1.3-2.3 MOL BIOTIN: MOL BSA S.A. ACTUAL: 0.0074-0.0084 M²/MG | | BSA: 8.7 μG/MG SA: 6.1 μG/MG HABA: 1.85 MOL BIOTIN: MOL BSA S.A. ACTUAL: 0.0077 M²/MG |
|---|---|---|---|
| μmol biotin/mg PMP | 1.6E-04 | 4.9E-04 | 2.4E-04 |
| μmol biotin/m²-actual | 1.9E-02 | 6.6E-02 | 3.2E-02 |
| μmol BSA/mg PMP | 1.3E-04 | 2.1E-04 | 1.3E-04 |
| μmol BSA/m²-actual | 1.6E-02 | 2.9E-02 | 1.7E-02 |
| μmol SA/mg PMP | 1.0E-04 | 1.4E-04 | 1.1E-04 |
| μmol SA/m²-actual | 1.2E-02 | 1.9E-02 | 1.4E-02 |
| μmol biotin-IgG/mg PMP | 2.1E-05 | 4.1E-05 | 2.1E-05 |
| μmol biotin-IgG/m²-actual | 2.5E-03 | 5.5E-03 | 2.8E-03 |

Molecular Weights: Biotin: 244 Da; BSA: 66,000 Da; SA: 56,000 Da; IgG: 150,000 Da As can be seen in Table 14, which is based on measurements of a commercially available microparticle (Dynal® DYNABEADS MyOne Tosylactivated, 1.0 micron diameter; Invitrogen Corporation), once the ligands (e.g., biotin) are non-saturated, subsequent layers of the binding surface will also be non-saturated. In a specific embodiment, a one micron microparticle having a surface area of about 0.0077 m²/mg and coated with the indicated amount of biotinylated BSA and SA bound $2.1 \times 10^{-5}$ μmol biotin-IgG per mg of PMP.

For the surface density measurements shown in Table 15, microparticle surface area (based on a smoothness assumption, microparticle diameter from 0.90 to 1.10 µm, and microparticle density from 1.4 to 1.8 g/cm$^3$) ranged from a minimum of 0.0030 m$^2$/mg to a maximum of 0.0048 m$^2$/mg.

TABLE 15

SURFACE DENSITY: SMOOTHNESS ASSUMPTION

| SUMMARY | BSA: 8.7-14.0 µG/MG<br>SA: 5.6-7.8 µG/MG<br>HABA: 1.3-2.3 MOL<br>BIOTIN: MOL BSA<br>S.A. SMOOTH:<br>0.0030-0.0048 M$^2$/MG<br>MICROPARTICLE<br>DENSITY:<br>1.4-1.8 G/CM$^3$ | | BSA: 8.7 µG/MG<br>SA: 6.1 µG/MG<br>HABA: 1.85 MOL<br>BIOTIN: MOL BSA<br>S.A. SMOOTH:<br>0.0030-0.0048 M$^2$/MG<br>MICROPARTICLE<br>DENSITY:<br>1.6 G/CM$^3$ | |
|---|---|---|---|---|
| µmol biotin/mg PMP | 1.6E−04 | 4.9E−04 | 2.4E−04 | |
| µmol biotin/m$^{2\text{-}smooth}$ | 3.3E−02 | 1.6E−01 | 5.1E−02 | 8.0E−02 |
| µmol BSA/mg PMP | 1.3E−04 | 2.1E−04 | 1.3E−04 | |
| µmol BSA/m$^{2\text{-}smooth}$ | 2.8E−02 | 7.0E−02 | 2.8E−02 | 4.4E−02 |
| µmol SA/mg PMP | 1.0E−04 | 1.4E−04 | 1.1E−04 | |
| µmol SA/m$^{2\text{-}smooth}$ | 2.1E−02 | 4.6E−02 | 2.3E−02 | 3.6E−02 |
| µmol biotin-IgG/mg$^{\text{-}smooth}$ | 2.1E−05 | 4.1E−05 | — | |
| µmol biotin-IgG/m$^{2\text{-}smooth}$ | 4.5E−03 | 1.3E−02 | — | |

Molecular Weights: Biotin: 244 Da; BSA: 66,000 Da; SA: 56,000 Da; IgG: 150,000 Da Table 15 assumes a smooth surface. Again, as can be seen in Table 15, once the ligands (e.g., biotin) are non-saturated, subsequent layers of the binding surface will also be non-saturated. However, due to the smoothness assumption, the surface density calculations result in greater µmmol of ligands (biotin) per meter squared, greater µmol of support couplers (BSA) per meter squared, greater µmmol of ligand binders (SA) per meter squared, and greater µmmol of capture moieties (biotin-IgG) per meter squared, compared to the surface density calculations without the smoothness assumption (see Table 14). The increase in surface density is due to the fact that the µmols/mg of biotin, BSA, SA, or biotin-IgG is constant, but the total surface area of the microparticle surface with smoothness assumption is less than the total surface area of the microparticle without smoothness correction. For example, if two microparticles have identical diameters and shape, but one microparticle is porous and the other microparticle is perfectly smooth, the porous microparticle will have greater available surface area per unit mass (m$^2$/mg) than the smooth microparticle. If both microparticles can bind ligand, and they are both offered the same amount of ligand, than the porous microparticle will bind less ligand per square meter than the smooth microparticle.

What is claimed is:

1. A blocked microparticulate binding surface for an affinity assay, comprising:
   a) a microparticle support surface;
   b) covalently coupled directly to the support surface, a plurality of support couplers, wherein less than a saturating amount of the support coupler is coupled with the support surface;
   c) a plurality of block copolymer molecules directly contacting the support surface, wherein the block copolymer molecules consist of a hydrophobic head group flanked by at least two hydrophilic tail groups having hydroxyl groups at the end of the tail, wherein the length of the two or more hydrophilic tails is independently about 2 to about 2.5 times the length of the hydrophobic head group, wherein the hydrophobic head group is adsorbed onto the surface of the support, and wherein the hydrophilic tail groups having hydroxyl groups that block passive protein absorption to the surface; and
   d) ligands coupled to the support coupler at a molar ratio of the ligand to the support coupler of not more than 5:1; wherein the support coupler is selected from the group consisting of BSA, ovalbumin, a fragment of BSA, a fragment of ovalbumin and a mixture thereof; and wherein the ligand is biotin.

2. The microparticulate binding surface of claim 1 wherein the microparticle support comprises an organic polymer or copolymer that is hydrophobic.

3. The blocked microparticulate binding surface of claim 1 wherein the microparticle support comprises a paramagnetic or superparamagnetic material.

4. The blocked microparticulate binding surface of claim 1 further comprising a ligand binder that is at least bivalent that is coupled with the ligand, wherein the ligand binder is selected from the group consisting of avidin, SA, neutravidin, a fragment of SA, a fragment of avidin, a fragment of neutravidin, and mixtures thereof.

5. The blocked microparticulate binding surface of claim 4 wherein the ligand binder is streptavidin.

6. The blocked microparticulate binding surface of claim 4 further comprising a capture moiety associated with the ligand binder, wherein the capture moiety is selected from the group consisting of an antibody, a binding fragment of an antibody, a receptor, a ligand of a receptor, a hormone, a receptor of a hormone, an enzyme, a substrate of an enzyme, a single stranded oligonucleotide, a single stranded polynucleotide, a double stranded oligonucleotide, a double stranded polynucleotide, an antigen, a peptide, and a protein.

7. The blocked microparticulate binding surface of claim 6 wherein the capture moiety is biotinylated.

8. The blocked microparticulate binding surface of claim 1 wherein the block copolymer molecules each comprise a polymer wherein the hydrophobic head group is a polypropylene oxide block and the hydrophilic tail groups are each polyethylene oxide blocks.

9. A microparticulate dispersion in an aqueous solution of a plurality of the blocked microparticulate of claim 1 and a block copolymer having a hydrophobic head group flanked by at least two hydrophilic tail groups having hydroxyl groups at the end of the tail.

10. The microparticulate dispersion of claim 9 wherein the microparticle support comprises an organic polymer or copolymer that is hydrophobic.

11. The microparticulate dispersion of claim 9 wherein the microparticle support comprises a paramagnetic or superparamagnetic material.

12. The microparticulate dispersion of claim 9 further comprising a ligand binder that is at least bivalent that is coupled with the ligand, wherein the ligand binder is selected from the group consisting of avidin, SA, neutravidin, a fragment of SA, a fragment of avidin, a fragment of neutravidin, and mixtures thereof.

13. The microparticulate dispersion of claim 12 wherein the ligand binder is streptavidin.

14. The microparticulate dispersion of claim 12 further comprising a capture moiety associated with the ligand binder, wherein the capture moiety is selected from the group consisting of an antibody, a binding fragment of an antibody, a receptor, a ligand of a receptor, a hormone, a receptor of a hormone, an enzyme, a substrate of an enzyme, a single stranded oligonucleotide, a single stranded polynucleotide, a double stranded oligonucleotide, a double stranded polynucleotide, an antigen, a peptide, and a protein.

15. The microparticulate dispersion of claim 14 wherein the capture moiety is biotinylated.

* * * * *